US009744152B2

(12) United States Patent
Miller et al.

(10) Patent No.: US 9,744,152 B2
(45) Date of Patent: Aug. 29, 2017

(54) VITAMINS C AND K FOR TREATING POLYCYSTIC DISEASES

(71) Applicants: IC-MedTech Corporation, Las Vegas, NV (US); Mayo Foundation for Medical Education and Research, Rochester, MN (US)

(72) Inventors: Thomas M. Miller, Las Vegas, NV (US); Tetyana V. Masyuk, Rochester, MN (US); Nicholas F. Larusso, Rochester, MN (US)

(73) Assignee: IC-MedTech Corporation, Las Vegas, NV (US)

( * ) Notice: Subject to any disclaimer, the term of this patent is extended or adjusted under 35 U.S.C. 154(b) by 0 days.

(21) Appl. No.: 15/197,560

(22) Filed: Jun. 29, 2016

(65) Prior Publication Data

US 2016/0303072 A1 Oct. 20, 2016

Related U.S. Application Data

(63) Continuation-in-part of application No. 14/681,869, filed on Apr. 8, 2015, now abandoned, which is a continuation of application No. 14/152,710, filed on Jan. 10, 2014, now abandoned, application No. 15/197,560, which is a continuation-in-part of application No. 14/985,989, filed on Dec. 31, 2015, now abandoned, which is a continuation of application No. 13/811,234, filed as application No. PCT/US2011/044443 on Jul. 19, 2011, now abandoned.

(60) Provisional application No. 61/751,702, filed on Jan. 11, 2013, provisional application No. 61/365,715, filed on Jul. 19, 2010.

(51) Int. Cl.
| | |
|---|---|
| A61K 31/375 | (2006.01) |
| A61K 31/122 | (2006.01) |
| A61K 9/48 | (2006.01) |
| A61K 31/185 | (2006.01) |
| A61K 9/20 | (2006.01) |
| A61K 9/00 | (2006.01) |

(52) U.S. Cl.
CPC .......... *A61K 31/375* (2013.01); *A61K 9/0019* (2013.01); *A61K 9/2054* (2013.01); *A61K 9/48* (2013.01); *A61K 31/122* (2013.01); *A61K 31/185* (2013.01); *A61K 9/0014* (2013.01)

(58) Field of Classification Search
None
See application file for complete search history.

(56) References Cited

U.S. PATENT DOCUMENTS

| | | |
|---|---|---|
| 6,468,414 B1 | 10/2002 | Mahdavi et al. |
| 7,091,241 B2 | 8/2006 | Gilloteaux et al. |
| 8,536,199 B2 | 9/2013 | Greenwald |
| 2003/0073738 A1 | 4/2003 | Gilloteaux et al. |
| 2007/0043110 A1 | 2/2007 | Gilloteaux et al. |
| 2010/0056625 A1 | 3/2010 | Miller et al. |
| 2011/0028436 A1 | 2/2011 | Greenwald |
| 2011/0160301 A1 | 6/2011 | Tsai et al. |
| 2012/0184609 A1* | 7/2012 | Jamison ............... A61K 9/0019 514/474 |
| 2013/0178522 A1 | 7/2013 | Jamison et al. |

FOREIGN PATENT DOCUMENTS

| | | |
|---|---|---|
| WO | WO 02/47493 | 6/2002 |
| WO | WO 2007/147128 | 12/2007 |
| WO | WO 2009/118726 | 10/2009 |
| WO | WO 2011/011317 | 10/2009 |

OTHER PUBLICATIONS

Abdul-Majeed et al., "Polycystic diseases in visceral organs," Obstet. Gynecol. Int., 2011, Epub 2011.
Aressy et al., "Cell cycle control by the CDC25 phosphatases," Anticancer Agents Med. Chem., 2008, 8, 818-824.
Baeuerle et al., "NF-kappa B: ten years after," Cell, 1996, 87, 13-20.
Baldwin, "The NF-kappa B and I kappa B proteins: new discoveries and insights," Annu. Rev. Immunol., 1996, 14, 649-683.
Banales et al., "The cAMP effectors Epac and protein kinase a (PKA) are involved in the hepatic cystogenesis of an animal model of autosomal recessive polycystic kidney disease (ARPKD)," Hepatology, 2009, 49, 160-174.
Beck et al., "Ascorbate/menadione-induced oxidative stress kills cancer cells that express normal or mutated forms of the oncogenic protein Bcr-Abl. An in vitro and in vivo mechanistic study," Invest. New Drugs, 2011, 29, 891-900.
Bijur et al., "Antimutagenic and promutagenic activity of ascorbic acid during oxidative stress," Environ. Mol. Mutagen., 1997, 30, 339-345.
Bijur et al., "Ascorbic acid dehydroascorbate induces cell cycle arrest at G2/M DNA damage checkpoint during oxidative stress," Environ. Mol. Mutagen., 1999, 33, 144-152.
Boutros et al., "The when and whores of CDC25 phosphatases," Curr. Opin. Cell. Biol., 2006,18, 185-191.

(Continued)

*Primary Examiner* — Bong-Sook Baek
(74) *Attorney, Agent, or Firm* — Jones Day

(57) ABSTRACT

Provided herein is a pharmaceutical composition comprising vitamin C and chromium-free vitamin K, and optionally one or more pharmaceutically acceptable excipient(s). Also provided herein is a chromium-free pharmaceutical composition comprising vitamin C and vitamin K, and optionally one or more pharmaceutically acceptable excipient(s). Further provided herein is a method of treating, preventing, or managing an NFκB-mediated condition, disorder, or disease, comprising administering to the subject a therapeutically effective amount of vitamin C and chromium-free vitamin K. Provided herein are methods for treating, preventing, or ameliorating one or more symptoms of a polycystic disease in a subject, comprising administering to the subject a therapeutically effective amount of vitamins C and K.

33 Claims, 7 Drawing Sheets

(56) References Cited

OTHER PUBLICATIONS

Buc Calderon et al., "Potential therapeutic application of the association of vitamins C and K3 in cancer treatment," Curr. Med. Chem., 2002, 9, 2269-2285.
Carcamo et al., "Vitamin C suppresses TNF alpha-induced NF kappa B activation by inhibiting I kappa B alpha phosphorylation," Biochemistry, 2002, 41, 12995-13002.
Carpenter et al.,., "Receptors for epidermal growth factor and other polypeptide mitogens," Ann. Rev. Biochem., 1987, 56, 881-914.
Chen et al., "Involvement of Rb family proteins, focal adhesion proteins and protein synthesis in senescent morphogenesis induced by hydrogen peroxide," J. Cell Sci., 2000, 113, 4087-4097.
Davila et al., "Mutations in SEC63 cause autosomal dominant polycystic liver disease," Nat. Genet., 2004, 36, 575-577.
De Laurenzi et al., "Cell death by oxidative stress and ascorbic acid regeneration in human neuroectodermal cell lines," Eur. J. Cancer, 1995, 31, 463-466.
Deep et al., "New combination therapies with cell-cycle agents," Curr. Opin. Investig. Drugs, 2008, 9, 591-604.
Difara, "The remarkable anticancer properties of vitamin K," LifeExtension Magazine, Nov. 2010.
Ducruet et al., "Dual specificity protein phosphatases: therapeutic targets for cancer and Alzheimer's disease," Annu. Rev. Phamacol. Toxicol., 2005, 45, 725-750.
Dypbukt et al., "Different prooxidant levels stimulate growth, trigger apoptosis, or produce necrosis of insulin-secreting RINm5F cells," J. Biol. Chem., 1994, 269, 30553-30560.
Everson et al., "Polycystic disease of the liver," Hepatology, 2004, 40, 774-782.
"Exploring Apatone®," SummaMagzine, Fall 2010, 6-12.
Faloon, "Protection against arterial calcification, bone loss, cancer, and aging," LifeExtension Magazine, 2009, 1-15.
Fedeles et al., "A genetic interaction network of five genes for human polycystic kidney and liver diseases defines polycystin-1 as the central determinant of cyst formation," Nat. Genet., 2011, 43, 639-647.
Gelvan et al., "Sites and mechanisms of low-level oxidative stress in cultured cells," Biochem. Biophys. Res. Commun., 1995, 206, 421-428.
Gilloteaux et al., "Cell damage and death by autoschizis in human bladder (RT4) carcinoma cells resulting from treatment with ascorbate and menadione," Untrastruct. Pathol., 2010, 34, 140-160.
Harris et al., "Polycystic kidney disease," Annu. Rev. Med., 2009, 60, 321-337.
Hoevenaren et al., "Polycystic liver: clinical characteristics of patients with isolated polycystic liver disease compared with patients with polycystic liver and autosomal dominant polycystic kidney disease," Liver Int., 2008, 28, 264-270.
Hughes et al., "The polycystic kidney disease 1 (PKD1) gene encodes a novel protein with multiple cell recognition domains," Nat. Genet., 1995, 10, 151-160.
Jamison et al., "Apatone® exhibits antitumor activity against prostate cancer," Summa Health System Research Forum, Sep. 25, 2009, p. 79.
Jamison et al., "Cell cycle arrest and autoschizis in a human bladder carcinoma cell line following vitamin C and vitamin K3 treatment," Biochem. Pharm., 2004, 67, 337-351.
Jamison et al., "Flow cytometric and ultrastructural aspects of the synergistic antitumor activity of vitamin C and vitamin K3 combinations against prostatic carcinoma cells," Tissue Cell, 1996, 28, 687-701.
Jamison et al., "Induction of cell cycle arrest and autoschizis in a human bladder carcinoma cell line by vitamins C and K3," Summa Health System Research Forum, Sep. 25, 2009, p. 80.
Jamison et al., "Liquid crystalline compounds as pharmaceuticals," Summa Health System Research Forum, Sep. 25, 2009, C3.
Jamison et al., "Redistribution of fibrillarin following treatment of human bladder carcinoma cells with Apatone®," Summa Health System Research Forum, Sep. 25, 2009, p. 78.
Jamison et al., "The in vitro and in vivo antitumor activity of vitamin C: K3 combinations against prostate cancer," Trends in Prostate Cancer Research, 2005, Editor: John Lucas, pp. 189-236.
Juan et al., "Vitamin K3 inhibits growth of human hepatoma HepG2 cells by decreasing activities of both p34CDC2 kinase and phosphatase," Biochem. Biophys. Res. Commun., 1993, 190, 907-913.
Kassouf et al., "Vitamins C and K3 sensitize human urothelial tumors to gemcitabine," J. Urol., 2006, 176, 1642-1647.
Koptides et al., "Autosomal dominant polycystic kidney disease: molecular genetics and molecular pathogenesis," Hunt Genet., 2000, 107, 115-126.
Lisanti et al., "Hydrogen peroxide fuels aging, inflammation, cancer metabolism and metastasis: the seed and soil also needs 'fertilizer'," Cell Cycle., 2011, 10, 2440-2449.
Masyuk et al., "Polycystic liver disease: new insights into disease pathogenesis.," Hepatology, 2006, 43, 906-908.
Masyuk et al., "Cholangiociliopathies: genetics, molecular mechanisms and potential therapies," Curr. Opin. Gastroenterol., 2009, 25:265-271.
Masyuk et al., "Inhibition of Cdc25A suppresses hepato-renal cystogenesis in rodent models of polycystic kidney and liver disease," Gastroenterology 2012, 142, 622-633.
McGuire et al., "Elucidating the pathway of Apatone® induced DNase II reactivation during autoschizic cell death," Summa Health System Research Forum, Sep. 25, 2009.
Mochizuki et al., "PKD2, a gene for polycystic kidney disease that encodes an integral membrane protein," Science, 1996, 272, 1339-1342.
Muller et al., "An interaction between human Sec63 and nucleoredoxin may provide the missing link between the SEC63 gene and polycystic liver disease," FEBS Lett., 2011, 585, 596-600.
Nagao et al., "Tumor invasion is inhibited by phosphorylated ascorbate via enrichment of intracellular vitamin C and decreasing of oxidative stress," J. Cancer Res. Clin. Oncol., 2000, 126, 511-518.
Noto et al., "Effects of sodium ascorbate (vitamin C) and 2-methyl-1,4-naphthoquinone (vitamin K3) trealmenton human humor cell growth in vitro," Cancer, 1989, 63, 901-906.
Osada et al., "The utility of vitamin K3 (menadione) against pancreatic cancer," Anticancer Res., 2008, 28, 45-50.
Ozaki et al., "Menatetrenone, a vitamin K2 analogue, inhibits hepatocellular carcinoma cell growth by suppressing cyclin D1 expression through inhibition of nuclear factor kappaB activation," Clin. Cancer Res. 2007, 13, 2236-2245.
Qian et al., "Clinical profile of autosomal dominant polycystic liver disease," Hepatology, 2003, 37, 164-171.
Qian, "Isolated polycystic liver disease," Adv. Chronic Kidney Dis., 2010, 17, 181-189.
Reces et al., "Autosomal dominant polycystic liver disease in a family without polycystic kidney disease associated with a novel missense protein kinase C substrate 80K-H mutation," World J. Gastroenterol., 2005, 11, 7690-7693.
Sanzen et al., "Polycystic kidney rat is a novel animal model of Caroli's disease associated with congenital hepatic fibrosis," Am. J. Pathol., 2001, 158, 1605-1612.
Sata et al., "Menadione induces both necrosis and apoptosis in rat pancreatic acinar AR4-2J cells," Free Radic. Biol. Med., 1997, 23, 844-850.
Stancovski et al., "NF-kappaB activation: the I kappaB kinase revealed?" Cell, 1997, 91, 299-302.
Taper and Roberfroid, "Cancer chemotherapy protentiation induced by combined vitamin C and K3 with ferrous sulfate pretreatment," Oncol. (Life Sci. Adv.), 1992, 11, 19-25.
Taper et al., "Inhibition of the development of metastases by dietary vitamin C:K3 combination," Life Sci., 2004, 75, 955-967.
Tareen et al, "A 12 week, open label, phase I/IIa study using apatone for the treatment of prostate cancer patients who have failed standard therapy," Int. J. Med. Sci., 2008, 5, 62-67.
Timofeev et al, "Human Cdc25A phosphatase has a non-redundant function in G2 phase by activating Cyclic A-dependent kinases," FEBS Lett., 2009, 583, 841-847.

(56) References Cited

OTHER PUBLICATIONS

Tsai et al., "Structure-activity relationship analysis of phenolic compounds with antioxidant, anti-inflammatory, and anticancer activities," Summa Health System Research Forum, Sep. 25, 2009, p. 76.
Venugopal et al., "Synergistic antitumor activity of vitamin C and K3 on human urologic tumor cell lines," Life Sci., 1996, 59, 1389-1400.
Venugopal et al., "Synergistic antitumor activity of vitamins C and K3 against human prostate carcinoma cell lines," Cell Biol. Int., 1996, 20, 787-797.
Verrax et al., "The association of vitamins C and K3 kills cancer cells mainly by autoschizis, a novel form of cell death. Basis for their potential use as coadjuvants in anticancer therapy," Eur. J. Med. Chem., 2003, 38, 451-457.
Vita et al., "Pankiller effect of prolonged exposure to menadione on glioma cells: potentiation by vitamin C," Invest. New Drugs, 2011, 29, 1314-1320.
Waanders et al., "Extensive mutational analysis of PRKCSH and SEC63 broadens the spectrum of polycystic liver disease," Hum. Mutat., 2006, 27, 830.
Wang et al., "Effects of vitamin C on androgen receptor mediated actions in human prostate adenocarcinoma cell line LAPC-4," Urology, 2003, 62, 167-171.
Ward et al., "The gene mutated in autosomal recessive polycystic kidney disease encodes a large, receptor-like protein," Nat. Genet., 2002, 30, 259-269.
Yamamoto et al., "Transcriptional roles of nuclear factor kappa B and nuclear factor-interleukin-6 in the tumor necrosis factor alpha-dependent induction of cyclooxygenase-2 in MC3T3-E1 cells," J. Biol. Chem., 1995, 270, 31315-31320.
Yang et al., "Inhibition of the DNA-binding activity of NF-kappa B by gold compounds in vitro," FEBS Lett., 1995, 36, 89-96.
Takiar et al., "Polycystic kidney disease: Pathogenesis and potential therapies," Biochim. Biophys. Acta, 2010, 1812, 1337-1343.
Bergmann et al., "PKHD1 Mutations in autosomal recessive polycystic kidney disease (ARPKD)," Human Mutation, 2004, 23, 453-463.
Gevers and Drenth, "Diagnosis and management of polycystic liver disease," Nat. Rev. Gastroenterol. Hepatol., 2013, 10, 101-108.
"Summa Health enters into co-development agreement with Mayo Clinic and IC-MedTech," ResearchViews, Sep. 2, 2011.

* cited by examiner

Non-treated  VC  VK3  Apatone (VC:VK3)

FIG. 6A  FIG. 6B  FIG. 6C  FIG. 6D
Non-treated  VC  VK3  Apatone (VC:VK3)
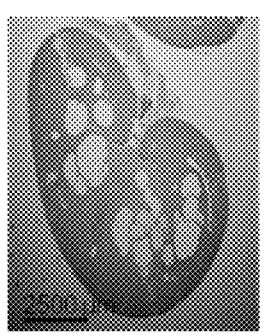 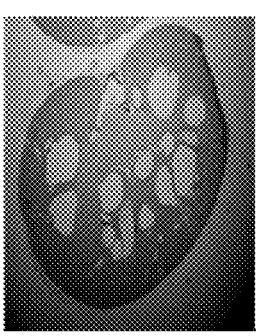 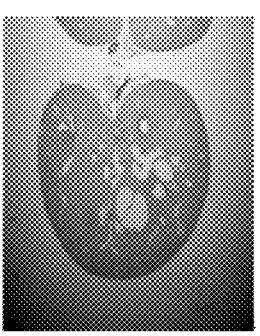 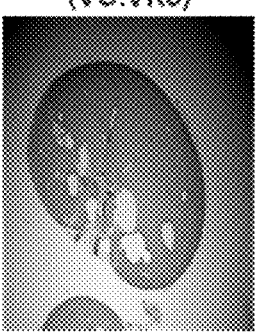
FIG. 6E  FIG. 6F
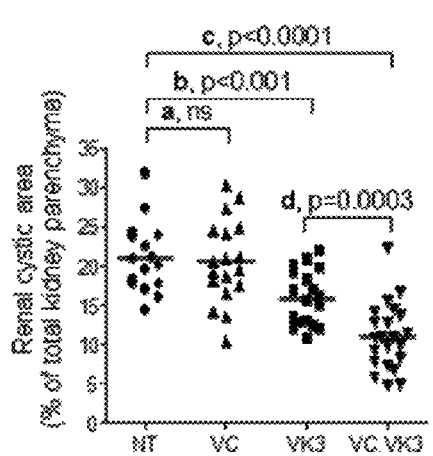 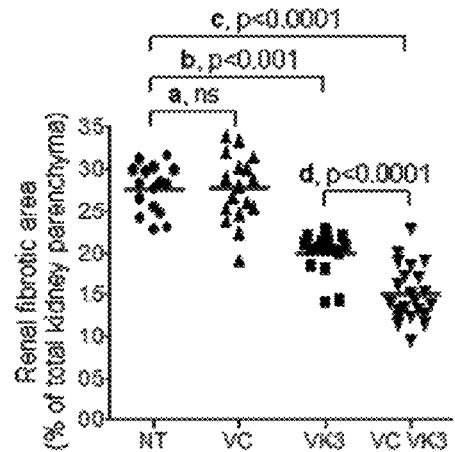

Non-treated    VC    VK3    Apatone (VC:VK3)

Non-treated  VC  VK3  Apatone (VC:VK3)

US 9,744,152 B2

VITAMINS C AND K FOR TREATING POLYCYSTIC DISEASES

CROSS REFERENCE TO RELATED APPLICATION

This application is a continuation-in-part of U.S. application Ser. No. 14/985,989, filed Dec. 31, 2015, which is a continuation of U.S. application Ser. No. 13/811,234, which is the National Stage of International Application No. PCT/US2011/044443, filed Jul. 19, 2011, which claims the benefit of U.S. Provisional Patent Application No. 61/365,715, filed Jul. 19, 2010; and a continuation-in-part of U.S. application Ser. No. 14/681,869, filed Apr. 8, 2015, which is a continuation of U.S. application Ser. No. 14/152,710, filed Jan. 10, 2014, which claims the benefit of U.S. Provisional Application No. 61/751,702, filed Jan. 11, 2013; the disclosure of each of which is incorporated herein by reference in its entirety.

FIELD

Provided herein is a pharmaceutical composition comprising vitamin C and chromium-free vitamin K, and optionally one or more pharmaceutically acceptable excipients. Also provided herein is a chromium-free pharmaceutical composition comprising vitamin C and vitamin K, and optionally one or more pharmaceutically acceptable excipients. Further provided herein is a method of treating, preventing, or managing an NFκB-mediated condition, disorder, or disease, comprising administering to the subject a therapeutically effective amount of vitamin C, and chromium-free vitamin K. Provided herein are methods for treating, preventing, or ameliorating one or more symptoms of a polycystic disease in a subject, comprising administering to the subject a therapeutically effective amount of vitamins C and K.

BACKGROUND

Nuclear factor kappa B (NFκB) is a family of inducible transcription factors found virtually ubiquitously in all cells. NFκB can be activated in response to a wide array of harmful cellular stimuli, including cytokines, bacterial lipopolysaccharide, viral infection, phorbol esters, ultraviolet radiation, and free radicals (Baldwin, *Ann. Rev. Immunol.* 1996, 14, 649-681). NFκB has been implicated in a variety of human diseases and disorders, including inflammation, asthma, atherosclerosis, viral infections, septic shock, arthritis, autoimmune diseases, and cancer (Baldwin, *Ann. Rev. Immunol.* 1996, 14, 649-681; Baeuerle et al., *Cell* 1996, 87, 13-20; Stancovski et al., *Cell,* 1997, 91, 299-302). For example, NFκB is activated in arthritic synovium (Yang et al., *FEBS Letts.* 1995, 361, 89-96; and Baldwin, *Ann. Rev. Immunol.* 1996, 14, 649-681). Cyclooxygenase-2, an inducible enzyme regulated by NFκB, is responsible for the increased production of prostaglandins and thromboxane in inflammatory disease (Yamamoto et al., *J. Biol. Chem.* 1995, 270, 31315-31350; Crofford et al., *J. Clin. Invest.* 1994, 93, 1095-1101). Therefore, there exists a need for therapies to modulate the cellular functions of NFκB.

Polycystic kidney disease (PKD) is the most common life-threatening genetic disease, affecting more than 600,000 Americans and an estimated 12.5 million people worldwide. PKD is characterized by the presence of fluid-filled cysts in the kidneys, often resulting in renal failure. About 50 percent of patients with PKD will have kidney failure by age 60 and about 60 percent will have kidney failure by age 70. Although kidneys usually are the most severely affected organs, PKD can cause cysts to develop in the liver and elsewhere in the body. Liver cystogenesis occurs in more that 95% of PKD patients.

Autosomal dominant PKD (ADPKD) and autosomal recessive PKD (ARPKD) are the most common forms of PKD. Harris et al., *Annu. Rev. Med.* 2009, 60, 321-337. ADPKD is passed from a parent to a child by an autosomal dominant type of inheritance. Thus, only one copy of the abnormal gene is needed to cause the disease. ADPKD is caused by mutations in PKD1 (encoding polycystin-1), PKD2 (encoding polycystin-2), and/or PKD3 (unmapped). Harris et al., *Annu. Rev. Med.* 2009, 60, 321-337; Hughes et al., *Nature Genetics* 1995, 10, 151-160; Mochizuki et al., *Science* 1996, 272, 1339-1342; Koptides et al., *Hum. Genet.* 2000, 107, 115-126. Polycystin-1 is a membrane receptor capable of binding and interacting with many proteins, carbohydrates, and lipids, and eliciting intracellular responses through phosphorylation pathways, whereas polycystin-2 is thought to act as a calcium-permeable channel. Polycystins regulate tubular and vascular development in the kidneys and in other organs, including the liver, brain, arterial blood vessels, and pancreas, causing extra-renal manifestations of the disease.

ARPKD is the most common genetic cystic renal disease occurring in infancy and childhood. ARPKD is passed by an autosomal recessive pattern of inheritance. Thus, both parents must carry the abnormal gene, and both must pass the gene to the child in order for the child to develop the disease. ARPKD is caused by mutations in PKHD1 (encoding fibrocystin). Harris et al., *Annu. Rev. Med.* 2009, 60, 321-337; Ward et al., *Nature Genetics.* 2002, 30, 259-269. Fibrocystin has been found in the same complex as polycystin-2. However, the precise function of fibrocystin is at present unknown, but it may mediate its activity through polycystin-2. Harris et al., *Annu. Rev. Med.* 2009, 60, 321-337.

Other polycystic diseases include polycystic liver disease (PLD), polycystic pancreas disease (PPD), and polycystic ovarian syndrome (PCOS). Abdul-Majeed et al., *Obstet. Gynecol. Int.* 2011, Epub 2011. PLD is characterized by the presence of multiple bile duct-derived epithelial cysts scattered in the liver parenchyma. PLD occurs isolated in the liver or in combination with PKD. Though cystic liver is one of the most common extrarenal manifestations observed in PKD, it also exists as an isolated inherited cystic disease without any kidney cysts. Qian, *Adv. Chronic Kidney Dis.* 2010, 17, 181-189. Isolated autosomal dominant polycystic liver disease (ADPLD) is genetically distinct from PLD associated with ADPKD, although it may have similar pathogenesis and clinical manifestations. Qian et al., *Hepatology* 2003, 37, 164-171; Reces et al., *World J. Gastroenterol.* 2005, 11, 7690-7693. PLD is genetically heterogeneous, all being transmitted autosomally in a dominant or recessive fashion. PLD is caused by mutations in PPRKCSH or SEC63. Davila et al., *Nature Genetics* 2004, 36, 575-577; Waanders et al., *Hum. Mutat.* 2006, 27, 830. PPRKCSH encodes the noncatalytic β-subunit of glucosidase II (GIIβ) involved in the folding of glycoproteins, whereas SEC63 encodes a protein involved in protein trafficking in the ER. Fedeles et al., *Nature Genetics* 2011, 43, 639-647; Muller et al., *FEBS Lett.* 2011, 585, 596-600; Qian, *Adv. Chronic Kidney Dis.* 2010, 17, 181-189.

Currently, there is no approved treatment for polycystic diseases to halt cyst growth. For example, the management for PKD and PLD is centered on palliating symptoms and treating complications. Qian, *Adv. Chronic Kidney Dis.*

2010, 17, 181-189. Therefore, there is a need for an effective method for the treatment of a polycystic disease.

SUMMARY OF THE DISCLOSURE

Provided herein is a pharmaceutical composition comprising (a) vitamin C, or a pharmaceutically acceptable salt, solvate, or hydrate thereof, and (b) vitamin K, or a single enantiomer, a mixture of enantiomers, or a mixture of diastereomers thereof, or a pharmaceutically acceptable salt, solvate, or hydrate thereof. In one embodiment, the pharmaceutical compositions provided herein further comprise a pharmaceutically acceptable vehicle, carrier, diluent, or excipient, or a mixture thereof.

Also provided herein is a chromium-free pharmaceutical composition comprising (a) vitamin C, or a pharmaceutically acceptable salt, solvate, or hydrate thereof, in combination with (b) vitamin K, or a single enantiomer, a mixture of enantiomers, or a mixture of diastereomers thereof, or a pharmaceutically acceptable salt, solvate, or hydrate thereof. In one embodiment, the pharmaceutical compositions provided herein further comprise a pharmaceutically acceptable vehicle, carrier, diluent, or excipient, or a mixture thereof.

Further provided herein is a method of treating, preventing, or managing an NFκB-mediated condition, disorder, or disease, comprising administering to the subject a therapeutically effective amount of vitamin C, or a pharmaceutically acceptable salt, solvate, or hydrate thereof, in combination with chromium-free vitamin K, or a single enantiomer, a mixture of enantiomers, or a mixture of diastereomers thereof, or a pharmaceutically acceptable salt, solvate, or hydrate thereof.

In one embodiment, the NFκB-mediated condition, disorder, or disease is one or more selected from aging, Alzheimer's disease, amyloidosis, angiitis, ankylosing spondylitis, arthrosclerosis, anti-adhesion (prevent surgical adhesions), arrhythmia, arterosclerosis, aseptic osteolysis, asthma, autoimmune diseases with inflammation, avascular necrosis, Bell's palsy, bursitis, cancers, carpal tunnel, celiac disease, chronic fatigue syndrome, colitis, common cold, congenital hip dysplasia, chronic obstructive pulmonary disease (COPD), Crohn's disease, cystic kidney disease, cystic liver disease, dermatitis, diabetes, diabetes type I and II, diverticulitis, endometriosis, exercise intolerance, fibromyalgia, frozen shoulder, gout, Grave's disease, gut diseases, headache, heart failure, hepatitis, herpes, HIV infections, HIV associated rheumatoid diseases, infectious arthritis, inflammation, inflammatory bowel, ischemia, lupus, Lyme disease, migraine treatment, multiple sclerosis, muscular dystrophy, nephritis, neuropathological diseases, neuropathy, osteolytic arthritis, organ/tissue transplant, osteolysis, osteopenia, osteoporosis, Paget's disease, Parkinson's disease, pelvic inflammatory disease, pigment diseases, polycystic kidney disease, polycystic liver disease, pseudotumors, psoriatic arthritis, pseudogout, rheumatoid arthritis, renal diseases, sarcodosis, scleraderma, scurvy, sepsis, skin diseases, sleep apnoea (or sleep apnea), space travel (bone density disorder), tendonitis, thyroid associated arthritis, transfection procedures, ulcerative colitis, ulcers, viral infection, warts, and wound healing.

Provided herein is a method of reducing NFκB production in a cell, comprising contacting the cell with an effective amount of vitamin C, or a pharmaceutically acceptable salt, solvate, or hydrate thereof, in combination with chromium-free vitamin K, or a single enantiomer, a mixture of enantiomers, or a mixture of diastereomers thereof, or a pharmaceutically acceptable salt, solvate, or hydrate thereof.

Provided herein is a method for treating, preventing, or ameliorating a polycystic disease in a subject, comprising administering to the subject a therapeutically effective amount of vitamin C, or a pharmaceutically acceptable salt, solvate, or hydrate thereof and vitamin K, or a single enantiomer, a mixture of enantiomers, or a mixture of diastereomers thereof, or a pharmaceutically acceptable salt, solvate, or hydrate thereof.

Also provided herein is a method for treating, preventing, or ameliorating a polycystic kidney disease in a subject, comprising administering to the subject a therapeutically effective amount of vitamin C, or a pharmaceutically acceptable salt, solvate, or hydrate thereof; and vitamin K, or a single enantiomer, a mixture of enantiomers, or a mixture of diastereomers thereof, or a pharmaceutically acceptable salt, solvate, or hydrate thereof.

Furthermore, provided herein is a method for treating, preventing, or ameliorating a polycystic liver disease in a subject, comprising administering to the subject a therapeutically effective amount of vitamin C, or a pharmaceutically acceptable salt, solvate, or hydrate thereof; and vitamin K, or a single enantiomer, a mixture of enantiomers, or a mixture of diastereomers thereof, or a pharmaceutically acceptable salt, solvate, or hydrate thereof.

Provided herein is a method for inhibiting cystogenesis in an organ, comprising contacting the organ with an effective amount of vitamin C, or a pharmaceutically acceptable salt, solvate, or hydrate thereof and vitamin K, or a single enantiomer, a mixture of enantiomers, or a mixture of diastereomers thereof, or a pharmaceutically acceptable salt, solvate, or hydrate thereof.

Provided herein is a method for inhibiting cystogenesis in a kidney, comprising contacting the kidney with an effective amount of vitamin C, or a pharmaceutically acceptable salt, solvate, or hydrate thereof; and vitamin K, or a single enantiomer, a mixture of enantiomers, or a mixture of diastereomers thereof, or a pharmaceutically acceptable salt, solvate, or hydrate thereof.

Provided herein is a method for inhibiting cystogenesis in a liver, comprising contacting the liver with an effective amount of vitamin C, or a pharmaceutically acceptable salt, solvate, or hydrate thereof; and vitamin K, or a single enantiomer, a mixture of enantiomers, or a mixture of diastereomers thereof, or a pharmaceutically acceptable salt, solvate, or hydrate thereof.

BRIEF DESCRIPTION OF THE DRAWINGS

FIGS. 6A to 6D show images of picrosirius red-stained kidney sections of PCK rats untreated or treated with vitamin C, vitamin $K_3$, or APATONE®.

FIGS. 6E and 6F show effects of vitamin C, vitamin $K_3$, and APATONE® on renal cystogenesis in PCK rats. NT: non-treated; VC: vitamin C-treated; VK3: vitamin $K_3$-treated; and VC:CK3: APATONE®-treated.

DETAILED DESCRIPTION

Figure 1A:
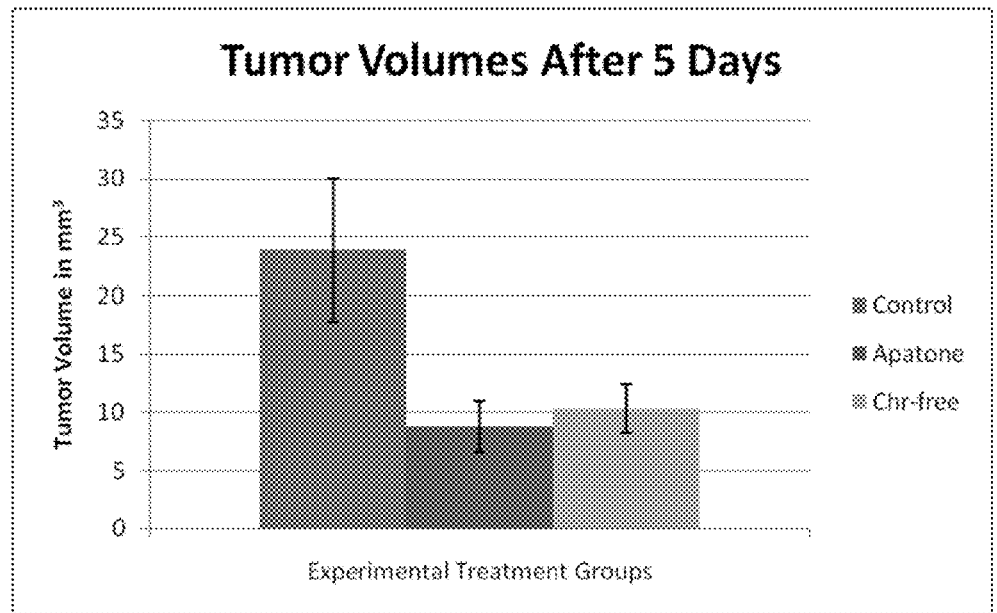
FIGS. 1A and 1B provide tumor volumes at Day 5 and Day 7 in mice with K562 human leukemia cells, respectively, showing a comparison between control animals, animals treated chromium-containing $CK_3$, and animals treated with chromium-free $CK_3$ (from left to right).

To facilitate understanding of the disclosure set forth herein, a number of terms are defined below.

Generally, the nomenclature used herein and the laboratory procedures in organic chemistry, medicinal chemistry, biochemistry, biology, pharmacology, and others described herein are those well known and commonly employed in the art. Unless defined otherwise, all technical and scientific terms used herein generally have the same meaning as commonly understood by one of ordinary skill in the art to which this disclosure belongs.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" refers to a material that is not found in nature or that has been structurally modified or synthesized by man.

The terms "nuclear factor kappa B" and "NFκB" are used interchangeably herein and refer to a member of the Rel family of transcription factors that contain the Rel homology (RH) domain, or variant thereof, as described, for example, in Carpenter et al., *Ann. Rev. Biochem.* 1987, 56, 881-914. Examples of NFκB include, but are not limited to, RelA (p65), c-Rel, p50, p52, and the *Drosophila* dorsal and Dif gene products. NFκB variants include proteins substantially homologous to a native NFκB, i.e., proteins having one or more naturally or non-naturally occurring amino acid deletions, insertions, or substitutions (e.g., NFκB derivatives, homologs, and fragments), as compared to the amino acid sequence of a native NFκB. The amino acid sequence of a NFκB variant is at least about 80% identical, at least about 90% identical, or at least about 95% identical to a native NFκB. In certain embodiments, the NFκB is p65 or a variant thereof.

The terms "NFκB-mediated condition, disorder, or disease" and "a condition, disorder, or disease mediated by NFκB" refer to a condition, disorder, or disease characterized by inappropriate, e.g., less than or greater than normal, NFκB activity. Inappropriate NFκB functional activity might arise as the result of NFκB expression in cells which normally do not express NFκB, increased NFκB expression or degree of intracellular activation, leading to, e.g., inflammatory and immune-related disorders or diseases; or decreased NFκB expression. An NFκB-mediated condition, disorder, or disease may be completely or partially mediated by inappropriate NFκB activity. In certain embodiments, an NFκB-mediated condition, disorder, or disease is one in which modulation of the NFκB activity results in some effect on the underlying condition or disorder, e.g., a NFκB antagonist or agonist results in some improvement in at least some of patients being treated.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The terms "manage," "managing," and "management" refer to preventing or slowing the progression, spread, or worsening of a condition, disorder, or disease, or of one or more symptoms (e.g., pain) thereof. Sometimes, the beneficial effects that a subject derives from a prophylactic or therapeutic agent do not result in a cure of the condition, disorder, or disease. In one embodiment, the term management refers to preventing or slowing the progression, spread, or worsening of the pain of osteolysis.

The term "contacting" or "contact" is meant to refer to bringing together of a therapeutic agent and cell or tissue such that a physiological and/or chemical effect takes place as a result of such contact. Contacting can take place in vitro, ex vivo, or in vivo. In one embodiment, a therapeutic agent is contacted with a cell in cell culture (in vitro) to determine the effect of the therapeutic agent on the cell. In another embodiment, the contacting of a therapeutic agent with a cell or tissue includes the administration of a therapeutic agent to a subject having the cell or tissue to be contacted.

The terms "therapeutically effective amount" and "effective amount" are meant to include the amount of a compound or combination of compounds that, when administered, is sufficient to prevent development of, or alleviate to some extent, one or more of the symptoms of the disorder, disease, or condition being treated. The term "therapeutically effective amount" or "effective amount" also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically acceptable material, composition, or vehicle, such as a liquid or solid filler, diluent, solvent, or encapsulating material. In one embodiment, each component is "pharmaceutically acceptable" in the sense of being compatible with other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st ed.; Lippincott Williams & Wilkins: Philadelphia, Pa., 2005; *Handbook of Pharmaceutical Excipients,* 6th ed.; Rowe et al., Eds.; The Pharmaceutical Press and the American Pharmaceutical Association: 2009; *Handbook of Pharmaceutical Additives,* 3rd ed.; Ash and Ash Eds.; Gower Publishing Company: 2007; *Pharmaceutical Preformulation and Formulation,* 2nd ed.; Gibson Ed.; CRC Press LLC: Boca Raton, Fla., 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease.

As used herein, unless otherwise specified, the term "APATONE®" refers to a pharmaceutical composition which comprises L-ascorbate and chromium-free 1,2,3,4-tetrahydro-2-methyl-1,4-dioxo-2-naphthalenesulfonate. In certain embodiments, the term "APATONE®" refers to a pharmaceutical composition, wherein the weight ratio of L-ascorbate to chromium-free 1,2,3,4-tetrahydro-2-methyl-1,4-dioxo-2-naphthalenesulfonate is 100 to 200.

The term "alkyl" refers to a linear or branched saturated monovalent hydrocarbon radical, wherein the alkyl may optionally be substituted with one or more substituents Q as described herein. For example, $C_{1-6}$ alkyl refers to a linear saturated monovalent hydrocarbon radical of 1 to 6 carbon atoms or a branched saturated monovalent hydrocarbon radical of 3 to 6 carbon atoms. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms, e.g., n-propyl and isopropyl), butyl (including all isomeric forms, e.g., n-butyl, isobutyl, sec-butyl, and t-butyl), pentyl (including all isomeric forms), and hexyl (including all isomeric forms).

The term "alkenyl" refers to a linear or branched monovalent hydrocarbon radical, which contains one or more, in one embodiment, one to five, in another embodiment, one, carbon-carbon double bond(s). The alkenyl may be optionally substituted with one or more substituents Q as described herein. The term "alkenyl" embraces radicals having a "cis" or "trans" configuration or a mixture thereof, or alternatively, a "Z" or "E" configuration or a mixture thereof, as appreciated by those of ordinary skill in the art. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

The term "alkynyl" refers to a linear or branched monovalent hydrocarbon radical, which contains one or more, in one embodiment, one to five, in another embodiment, one, carbon-carbon triple bond(s). The alkynyl may be optionally substituted with one or more substituents Q as described herein. For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms. In certain embodiments, the alkynyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynyl groups include, but are not limited to, ethynyl (—C≡CH), propynyl (including all isomeric forms, e.g., 1-propynyl (—C≡CCH$_3$) and propargyl (—CH$_2$C≡CH)), butynyl (including all isomeric forms, e.g., 1-butyn-1-yl and 2-butyn-1-yl), pentynyl (including all isomeric forms, e.g., 1-pentyn-1-yl and 1-methyl-2-butyn-1-yl), and hexynyl (including all isomeric forms, e.g., 1-hexyn-1-yl).

The term "cycloalkyl" refers to a cyclic saturated or non-aromatic unsaturated, bridged or non-bridged monovalent hydrocarbon radical, which is optionally substituted with one or more substituents Q as described herein. In certain embodiments, the cycloalkyl is a cyclic saturated bridged or non-bridged monovalent hydrocarbon radical, which is optionally substituted with one or more substituents Q as described herein. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclohexyl, cycloheptyl, bicyclo[2.1.1]hexyl, bicyclo[2.2.1]heptyl, decalinyl, and adamantyl.

The term "aryl" refers to a monocyclic aromatic group and/or multicyclic monovalent aromatic group that contain at least one aromatic hydrocarbon ring. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. In certain embodiments, the term "aryl" refers to a bicyclic or tricyclic carbon ring, where one of the rings is aromatic and the others of which may be saturated, partially unsaturated, or aromatic, for example, dihydronaphthyl, indenyl, indanyl, or tetrahydronaphthyl (tetralinyl). In certain embodiments, the aryl is optionally substituted with one or more substituents Q as described herein.

The term "aralkyl" or "arylalkyl" refers to a monovalent alkyl group substituted with one or more aryl groups. In certain embodiments, the aralkyl has from 7 to 30 ($C_{7-30}$), from 7 to 20 ($C_{7-20}$), or from 7 to 16 ($C_{7-16}$) carbon atoms. Examples of aralkyl groups include, but are not limited to, benzyl, 1-phenylethyl, 2-phenylethyl, and 3-phenylpropyl. In certain embodiments, the aralkyl is optionally substituted with one or more substituents Q as described herein.

The term "heteroaryl" refers to a monovalent monocyclic aromatic group or monovalent polycyclic aromatic group that contain at least one aromatic ring, wherein at least one aromatic ring contains one or more heteroatoms, each of which is independently selected from O, S, N, and P, in the ring. A heteroaryl group is bonded to the rest of a molecule through its aromatic ring. Each ring of a heteroaryl group can contain one or two O atoms, one or two S atoms, one to four N atoms, and/or one or two P atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, the heteroaryl is optionally substituted with one or more substituents Q as described herein.

The term "heterocyclyl" or "heterocyclic" refers to a monovalent monocyclic non-aromatic ring system or monovalent polycyclic ring system that contains at least one non-aromatic ring, wherein one or more of the non-aromatic ring atoms are heteroatoms, each of which is independently selected from O, S, N, and P; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. A heterocyclyl group is bonded to the rest of a molecule through its non-aromatic ring. In certain embodiments, the heterocyclyl is a monocyclic, bicyclic, tricyclic, or tetracyclic ring system, which may be spiro, fused, or bridged, and in which nitrogen or sulfur atoms may be optionally oxidized, nitrogen atoms may be optionally quaternized, and some rings may be partially or fully saturated, or aromatic. The heterocyclyl may be attached to the main structure at any heteroatom or carbon atom which results in the creation of a stable compound. Examples of heterocyclic groups include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, the heterocyclyl is optionally substituted with one or more substituents Q as described herein.

The term "halogen", "halide" or "halo" refers to fluorine, chlorine, bromine, and/or iodine.

The term "optionally substituted" is intended to mean that a group or substituent, such as an alkyl, alkylene, heteroalkylene, alkenyl, alkenylene, heteroalkenylene, alkynyl, alkynylene, cycloalkyl, cycloalkylene, aryl, arylene, aralkyl, heteroaryl, heteroarylene, heterocyclyl, or heterocyclylene group, may be substituted with one or more substituents Q, each of which is independently selected from, e.g., (a) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl, each of which is further optionally substituted with one or more, in one embodiment, one, two, three, or four, substituents $Q^a$; and (b) oxo (=O), halo, cyano (—CN), nitro (—NO$_2$), —C(O)$R^a$, —C(O)O$R^a$, —C(O)N$R^bR^c$, —C(N$R^a$)N$R^bR^c$, —O$R^a$, —OC(O)$R^a$, —OC(O)O$R^a$, —OC(O)N$R^bR^c$, —OC(=N$R^a$)N$R^bR^c$, —OS(O)$R^a$, —OS(O)$_2R^a$, —OS(O)N$R^bR^c$, —OS(O)$_2$N$R^bR^c$, —N$R^bR^c$, —N$R^a$C(O)$R^d$, —N$R^a$C(O)O$R^d$, —N$R^a$C(O)N$R^bR^c$, —N$R^a$C(=N$R^d$)N$R^bR^c$, —N$R^a$S(O)$R^d$, —N$R^a$S(O)$_2R^d$, —N$R^a$S(O)N$R^bR^c$, —N$R^a$S(O)$_2$N$R^bR^c$, —S$R^a$, —S(O)$R^a$, —S(O)$_2R^a$, —S(O)N$R^bR^c$, and —S(O)$_2$N$R^bR^c$, wherein each $R^a$, $R^b$, $R^c$, and $R^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl, each optionally substituted with one or more, in one embodiment, one, two, three, or four, substituents $Q^a$; or (iii) $R^b$ and $R^c$ together with the N atom to which they are attached form heteroaryl or heterocyclyl, optionally substituted with one or more, in one embodiment, one, two, three, or four, substituents $Q^a$. As used herein, all groups that can be substituted are "optionally substituted," unless otherwise specified.

In one embodiment, each $Q^a$ is independently selected from the group consisting of (a) oxo, cyano, halo, and nitro; and (b) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, and heterocyclyl; and (c) —C(O)$R^e$, —C(O)O$R^e$, —C(O)N$R^fR^g$, —C(N$R^e$)N$R^fR^g$, —OC(O)$R^e$, —OC(O)O$R^e$, —OC(O)N$R^fR^g$, —OC(=N$R^e$)N$R^fR^g$, —OS(O)$R^e$, —OS(O)$_2R^e$, —OS(O)N$R^fR^g$, —OS(O)$_2$N$R^fR^g$, —N$R^fR^g$, —N$R^e$C(O)$R^h$, —N$R^e$C(O)O$R^h$, —N$R^e$C(O)N$R^fR^g$, —N$R^e$C(=N$R^h$)N$R^fR^g$, —N$R^e$S(O)$R^h$, —N$R^e$S(O)$_2R^h$, —N$R^e$S(O)N$R^fR^g$, —N$R^e$S(O)$_2$N$R^fR^g$, —S$R^e$, —S(O)$R^e$, —S(O)$_2R^e$, —S(O)N$R^fR^g$, and —S(O)$_2$N$R^fR^g$; wherein each $R^e$, $R^f$, $R^g$, and $R^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, $C_{7-15}$ aralkyl, heteroaryl, or heterocyclyl; or (iii) $R^f$ and $R^g$ together with the N atom to which they are attached form heteroaryl or heterocyclyl.

In certain embodiments, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of one enantiomer and about 5% or less of the other enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The term "solvate" refers to a complex or aggregate formed by one or more molecules of a solute, e.g., a compound provided herein, and one or more molecules of a solvent, which present in a stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The term "chromium-free" refers to a chemical (e.g., a compound or composition) that contains no more than 100 ppm, 50 ppm, 20 ppm, 10 ppm, 5 ppm, 2 ppm, 1 ppm, 0.1 ppm, 10 ppb, or 1 ppb of chromium. In one embodiment, the term "chromium-free" refers to a chemical that contains no more than 10 ppm of chromium. In another embodiment, the term "chromium-free" refers to a chemical that contains no more than 5 ppm of chromium. In yet another embodiment, the term "chromium-free" refers to a chemical that contains no more than 2 ppm of chromium. In yet another embodiment, the term "chromium-free" refers to a chemical that contains no more than 1 ppm of chromium. In still another embodiment, the term "chromium-free" refers to a chemical that contains no more than 1 ppm of chromium. The chromium content can be determined using a conventional technique well known to one of ordinary skill in the art, e.g., inductively coupled plasma (ICP) technique.

The phrase "a single enantiomer, a mixture of enantiomers, or a mixture of diastereomers thereof, or a pharmaceutically acceptable salt, solvate, or hydrate thereof" has the same meaning as the phrase "(i) a single enantiomer, a mixture of enantiomers, or a mixture of diastereomers of the compound referenced therein; (ii) a pharmaceutically acceptable salt, solvate, or hydrate of the compound referenced therein; or (iii) a pharmaceutically acceptable salt, solvate, or hydrate of a single enantiomer, a mixture of enantiomers, or a mixture of diastereomers of the compound referenced therein."

Vitamin C

As used herein, the term "vitamin C" refers to L-ascorbic acid or a pharmaceutically acceptable salt thereof; or a pharmaceutically acceptable solvate or hydrate thereof. Vitamin C is also known as L-xyloascorbic acid, 3-oxo-L-gulofuranolactone (enol form), L-3-ketothreohexuronic acid lactone, antiscorbutic vitamin, cevitamic acid, adenex, allercorb, ascorin, ascorteal, ascorvit, cantan, cantaxin, catavin C, cebicure, cebion, cecon, cegiolan, celaskon, celin, cenetone, cereon, cergona, cescorbat, cetamid, cetabe, cetemican, cevalin, cevatine, cevex, cevimin, ce-vi-sol, cevitan, cevitex, cewin, ciamin, cipca, concemin, C-vin, daviamon C, duoscorb, hybrin, laroscorbine, lemascorb, planavit C, proscorbin, redoxon, ribena, scorbacid, scorbu-C, testascorbic, vicelat, vitacee, vitacimin, vitacin, vitascorbol, and xitix.

In one embodiment, vitamin C provided herein is L-ascorbic acid. In another embodiment, vitamin C provided herein is a pharmaceutically acceptable salt of L-ascorbic acid, or a pharmaceutically acceptable solvate or hydrate thereof.

Suitable bases for use in the preparation of pharmaceutically acceptable salts, include, but are not limited to, inorganic bases, such as magnesium hydroxide, calcium hydroxide, potassium hydroxide, zinc hydroxide, and sodium hydroxide; and organic bases, such as primary, secondary, tertiary, and quaternary, aliphatic and aromatic amines, including, but not limited to, L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

In one embodiment, vitamin C provided herein is an alkali or alkaline earth metal salt of L-ascorbic acid, or a pharmaceutically acceptable solvate or hydrate thereof. In another embodiment, vitamin C provided herein is sodium, potassium, calcium, or magnesium L-ascorbate, or a pharmaceutically acceptable solvate or hydrate thereof. In yet another embodiment, vitamin C provided herein is sodium L-ascorbate, or a pharmaceutically acceptable solvate or hydrate thereof. In yet another embodiment, vitamin C provided herein is sodium L-ascorbate, which is also known as vitamin C sodium, ascorbin, sodascorbate, natrascorb, cenolate, ascorbicin, or cebitate. In yet another embodiment, vitamin C provided herein is potassium L-ascorbate, or a pharmaceutically acceptable solvate or hydrate thereof. In yet another embodiment, vitamin C provided herein is magnesium L-ascorbate, or a pharmaceutically acceptable solvate or hydrate thereof. In still another embodiment, vitamin C provided herein is magnesium L-ascorbate.

In certain embodiments, the vitamin C provided herein is D-ascorbic acid or a pharmaceutically acceptable salt, or a pharmaceutically acceptable solvate or hydrate thereof.

In certain embodiments, the vitamin C provided herein is chromium-free. In certain embodiments, the chromium-free vitamin C provided herein contains no more than 100 ppm, 50 ppm, 20 ppm, 10 ppm, 5 ppm, 2 ppm, 1 ppm, 0.1 ppm, 10 ppb, or 1 ppb of chromium. In certain embodiments, the chromium-free vitamin C provided herein contains no greater than 10 ppm of chromium. In certain embodiments, the chromium-free vitamin C provided herein contains no greater than 5 ppm of chromium. In certain embodiments, the chromium-free vitamin C provided herein contains no greater than 2 ppm of chromium. In certain embodiments, the chromium-free vitamin C provided herein contains no greater than 1 ppm of chromium.

Vitamin K

As used herein, the term "vitamin K" refers to a 2-methyl-1,4-naphthoquinone derivative of Formula I or II:

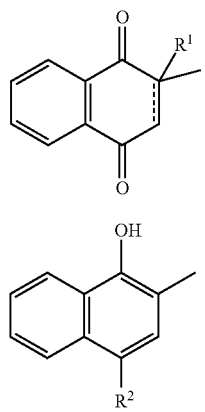

or an enantiomer, a mixture of enantiomers, or a mixture of two or more diastereomers thereof; or a pharmaceutically acceptable salt, solvate, or hydrate thereof; wherein $R^1$ is $C_{1-20}$ alkyl, $C_{2-20}$ alkenyl, $C_{2-20}$ alkynyl, or —$SO_3H$; and $R^2$ is hydroxyl or amino.

In certain embodiments, the vitamin K provided herein is vitamin $K_1$, vitamin $K_2$, vitamin $K_3$, vitamin $K_4$, or vitamin $K_5$, or a mixture of two or more thereof.

In one embodiment, the vitamin K provided herein is vitamin $K_1$, or a pharmaceutically acceptable salt, solvate, or hydrate thereof. Vitamin $K_1$ is also known as phylloquinone, [R—[R*,R*-(E)]]-2-methyl-3-(3,7,11,15-tetramethyl-2-hexadecenyl)-1,4-naphthalenedione, 2-methyl-3-phytyl-1,4-naphthoquinone, 3-phytylmenadione, phytomenadione, phytonadione, aqua-merphyton, konakion, mephyton, mono-day, veda-$K_1$, and veta-$K_1$.

In another embodiment, the vitamin K provided herein is vitamin $K_2$, or a pharmaceutically acceptable salt, solvate, or hydrate thereof. Vitamin $K_2$ is also known as menaquinones, and 2-methyl-3-all-trans-polyprenyl-1,4-naphthoquinones. Some non-limiting examples of vitamin $K_2$ include menaquinone 4, which is also known as vitamin $K_{2(20)}$; menaquinone 6, which is also known as vitamin $K_{2(30)}$; and menaquinone 7, which is also known as vitamin $K_{2(35)}$.

In yet another embodiment, the vitamin K provided herein is vitamin $K_3$, or a pharmaceutically acceptable salt, solvate, or hydrate thereof. Vitamin $K_3$ is also known as menadione, 2-methyl-1,4-naphthalenedione, 2-methyl-1,4-naphthoquinone, menaphthone, vitamin $K_{2(0)}$, kanone, kappaxin, kayklot, kayquinone, klottone, kolklot, thyloquinone, 1,2,3,4-tetrahydro-2-methyl-1,4-dioxo-2-naphthalenesulfonic acid, and sodium 1,2,3,4-tetrahydro-2-methyl-1,4-dioxo-2-naphthalenesulfonate.

In one embodiment, the vitamin K provided herein is 1,2,3,4-tetrahydro-2-methyl-1,4-dioxo-2-naphthalenesulfonic acid, or a pharmaceutically acceptable salt, solvate, or hydrate thereof. In another embodiment, the vitamin K provided herein is 1,2,3,4-tetrahydro-2-methyl-1,4-dioxo-2-naphthalenesulfonate (also known as menadione bisulfate), or a pharmaceutically acceptable solvate or hydrate thereof.

Suitable bases for use in the preparation of pharmaceutically acceptable salts, include, but are not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including, but not limited to, L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

In one embodiment, vitamin $K_3$ provided herein is an alkali or alkaline earth metal salt of 1,2,3,4-tetrahydro-2-methyl-1,4-dioxo-2-naphthalenesulfonic acid, or a pharmaceutically acceptable solvate or hydrate thereof. In another embodiment, vitamin $K_3$ provided herein is sodium, potassium, calcium, or magnesium 1,2,3,4-tetrahydro-2-methyl-1,4-dioxo-2-naphthalenesulfonate, or a pharmaceutically acceptable solvate or hydrate thereof. In yet another embodiment, vitamin $K_3$ provided herein is sodium 1,2,3,4-tetrahydro-2-methyl-1,4-dioxo-2-naphthalenesulfonate, or a pharmaceutically acceptable solvate or hydrate thereof. In yet another embodiment, vitamin $K_3$ provided herein is potassium 1,2,3,4-tetrahydro-2-methyl-1,4-dioxo-2-naphthalenesulfonate, or a pharmaceutically acceptable solvate or hydrate thereof. In yet another embodiment, vitamin $K_3$ provided herein is magnesium 1,2,3,4-tetrahydro-2-methyl-1,4-dioxo-2-naphthalenesulfonate, or a pharmaceutically acceptable solvate or hydrate thereof. In yet another embodiment, vitamin $K_3$ provided herein is sodium 1,2,3,4-tetrahydro-2-methyl-1,4-dioxo-2-naphthalenesulfonate. In yet another embodiment, vitamin $K_3$ provided herein is anhydrous sodium 1,2,3,4-tetrahydro-2-methyl-1,4-dioxo-2-naphthalenesulfonate. In yet another embodiment, vitamin $K_3$ provided herein is sodium 1,2,3,4-tetrahydro-2-methyl-1,4-dioxo-2-naphthalenesulfonate hydrate. In still another embodiment, vitamin $K_3$ provided herein is sodium 1,2,3,4-tetrahydro-2-methyl-1,4-dioxo-2-naphthalenesulfonate trihydrate.

In certain embodiments, the vitamin K provided herein is vitamin $K_4$, or a pharmaceutically acceptable salt, solvate, or hydrate thereof. Vitamin $K_4$ is also known as menadiol, 2-methyl-1,4-naphthalenediol, 2-methyl-1,4-naphthohydroquinone, 2-methyl-1,4-naphthoquinol, and dihydrovitamin $K_3$.

In certain embodiments, the vitamin K provided herein comprises vitamin $K_3$ and vitamin $K_4$, or pharmaceutically acceptable salts, solvates, or hydrates thereof.

In certain embodiments, the vitamin K provided herein is vitamin $K_5$, or a pharmaceutically acceptable salt, solvate, or hydrate thereof. Vitamin $K_5$ is also known as 4-amino-2-methyl-1-naphthalenol, 4-amino-2-methyl-1-naphthol, 1-hydroxy-2-methyl-4-aminonaphalene, 2-methyl-4-amino-1-hydroxynaphthalene, 2-methyl-4-amino-1-naphthol, 3-methyl-4-hydroxy-1-naphthylamine, and synkamin.

In certain embodiments, the vitamin K provided herein is chromium-free. In certain embodiments, the chromium-free vitamin K provided herein contains no more than 100 ppm, 50 ppm, 20 ppm, 10 ppm, 5 ppm, 2 ppm, 1 ppm, 0.1 ppm, 10 ppb, or 1 ppb of chromium. In certain embodiments, the chromium-free vitamin K provided herein contains no greater than 10 ppm of chromium. In certain embodiments, the chromium-free vitamin K provided herein contains no greater than 5 ppm of chromium. In certain embodiments, the chromium-free vitamin K provided herein contains no greater than 2 ppm of chromium. In certain embodiments, the chromium-free vitamin K provided herein contains no greater than 1 ppm of chromium.

In certain embodiments, the vitamin K provided herein is chromium-free vitamin $K_3$. In certain embodiments, the chromium-free vitamin $K_3$ provided herein contains no more than 100 ppm, 50 ppm, 20 ppm, 10 ppm, 5 ppm, 2 ppm, 1 ppm, 0.1 ppm, 10 ppb, or 1 ppb of chromium. In certain embodiments, the chromium-free vitamin $K_3$ provided herein contains no greater than 10 ppm of chromium. In certain embodiments, the chromium-free vitamin $K_3$ provided herein contains no greater than 5 ppm of chromium. In certain embodiments, the chromium-free vitamin $K_3$ provided herein contains no greater than 2 ppm of chromium. In certain embodiments, the chromium-free vitamin $K_3$ provided herein contains no greater than 1 ppm of chromium.

In certain embodiments, the vitamin K provided herein is chromium-free sodium 1,2,3,4-tetrahydro-2-methyl-1,4-dioxo-2-naphthalenesulfonate. In certain embodiments, the chromium-free sodium 1,2,3,4-tetrahydro-2-methyl-1,4-dioxo-2-naphthalenesulfonate contains no more than 100 ppm, 50 ppm, 20 ppm, 10 ppm, 5 ppm, 2 ppm, 1 ppm, 0.1 ppm, 10 ppb, or 1 ppb of chromium. In certain embodiments, the chromium-free sodium 1,2,3,4-tetrahydro-2-methyl-1,4-dioxo-2-naphthalenesulfonate contains no greater than 10 ppm of chromium. In certain embodiments, the chromium-free sodium 1,2,3,4-tetrahydro-2-methyl-1,4-dioxo-2-naphthalenesulfonate contains no greater than 5 ppm of chromium. In certain embodiments, the chromium-free sodium 1,2,3,4-tetrahydro-2-methyl-1,4-dioxo-2-naphthalenesulfonate contains no greater than 2 ppm of chromium. In certain embodiments, the chromium-free sodium 1,2,3,4-tetrahydro-2-methyl-1,4-dioxo-2-naphthalenesulfonate contains no greater than 1 ppm of chromium.

In certain embodiments, the chromium-free vitamin $K_3$ provided herein is made via a cerium mediated electrochemical technology (CETECH™) as described in U.S. Pat. No. 6,468,414, the disclosure of which is incorporated herein by reference in its entirety. Alternatively, chromium-free vitamin $K_3$ is available from commercial sources, such as PRO-K™ (Lonza Group Ltd, Switzerland).

Pharmaceutical Compositions: a Combination of Vitamins C and K

In one embodiment, provided herein are pharmaceutical compositions comprising (a) vitamin C, or a pharmaceutically acceptable salt, solvate, or hydrate thereof, in combination with (b) vitamin K, or a single enantiomer, a mixture of enantiomers, or a mixture of diastereomers thereof, or a pharmaceutically acceptable salt, solvate, or hydrate thereof. In another embodiment, the pharmaceutical compositions provided herein further comprise a pharmaceutically acceptable vehicle, carrier, diluent, or excipient, or a mixture of two or more thereof.

In another embodiment, provided herein are pharmaceutical compositions comprising (a) vitamin C, or a pharmaceutically acceptable salt, solvate, or hydrate thereof, in combination with (b) chromium-free vitamin K, or a single enantiomer, a mixture of enantiomers, or a mixture of diastereomers thereof, or a pharmaceutically acceptable salt, solvate, or hydrate thereof. In another embodiment, the pharmaceutical compositions provided herein further comprise a pharmaceutically acceptable vehicle, carrier, diluent, or excipient, or a mixture of two or more thereof.

In yet another embodiment, provided herein are pharmaceutical compositions comprising (a) chromium-free vitamin C, or a pharmaceutically acceptable salt, solvate, or hydrate thereof, in combination with (b) chromium-free vitamin K, or a single enantiomer, a mixture of enantiomers, or a mixture of diastereomers thereof, or a pharmaceutically acceptable salt, solvate, or hydrate thereof. In another embodiment, the pharmaceutical compositions provided herein further comprise a pharmaceutically acceptable vehicle, carrier, diluent, or excipient, or a mixture of two or more thereof.

In still another embodiment, provided herein is a chromium-free pharmaceutical composition comprising (a) vitamin C, or a pharmaceutically acceptable salt, solvate, or hydrate thereof, in combination with (b) vitamin K, or a single enantiomer, a mixture of enantiomers, or a mixture of diastereomers thereof, or a pharmaceutically acceptable salt, solvate, or hydrate thereof. In another embodiment, the pharmaceutical compositions provided herein further comprise a pharmaceutically acceptable vehicle, carrier, diluent, or excipient, or a mixture of two or more thereof.

In certain embodiments, the pharmaceutical compositions provided herein are chromium-free. In certain embodiments, the pharmaceutical compositions provided herein contain no more than 100 ppm, 50 ppm, 20 ppm, 10 ppm, 5 ppm, 2 ppm, 1 ppm, 0.1 ppm, 10 ppb, or 1 ppb of chromium. In certain embodiments, the pharmaceutical compositions provided herein contain no greater than 10 ppm of chromium. In certain embodiments, the pharmaceutical compositions provided herein contain no greater than 5 ppm of chromium. In certain embodiments, the pharmaceutical compositions provided herein contain no greater than 2 ppm of chromium. In certain embodiments, the pharmaceutical compositions provided herein contain no greater than 1 ppm of chromium.

In one embodiment, the weight ratio of vitamin C to vitamin K in the pharmaceutical compositions provided herein is ranging from about 4 to about 500, from about 10 to about 500, from about 50 to about 500, from about 25 to about 250, from about 50 to about 200, from about 50 to about 150, or from about 80 to about 120. In another embodiment, the weight ratio of vitamin C to vitamin K in the pharmaceutical compositions provided herein is about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, or about 250. In yet another embodiment, the weight ratio of vitamin C to vitamin K in the pharmaceutical compositions provided herein is about 100. In still another embodiment, the weight ratio of vitamin C to vitamin K in the pharmaceutical compositions provided herein is about 200.

In one embodiment, the molar ratio of vitamin C to vitamin K in the pharmaceutical compositions provided herein is ranging from about 10 to about 500, from about 25 to about 250, from about 50 to about 200, from about 50 to about 150, or from about 80 to about 120. In another embodiment, the molar ratio of vitamin C to vitamin K in the pharmaceutical compositions provided herein is about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, or about 250. In yet another embodiment, the molar ratio of vitamin C to vitamin K in the pharmaceutical compositions provided herein is about 100. In still another embodiment, the molar ratio of vitamin C to vitamin K in the pharmaceutical compositions provided herein is about 200.

The pharmaceutical compositions provided herein may be formulated in various dosage forms for oral, parenteral, and topical administration. The pharmaceutical compositions may also be formulated as modified release dosage forms, including delayed-, extended-, prolonged-, sustained-, pulsatile-, controlled-, accelerated-, fast-, targeted-, and programmed-release; and gastric retention dosage forms. These dosage forms can be prepared according to conventional methods and techniques known to those skilled in the art (See, e.g., *Remington: The Science and Practice of Pharmacy*, supra; *Modified-Release Drug Delivery Technology*, Rathbone et al., Eds., Drugs and the Pharmaceutical Science, Marcel Dekker, Inc.: New York, N.Y., 2003; Vol. 126).

In one embodiment, the pharmaceutical compositions provided herein are formulated in a dosage form for oral administration. In another embodiment, the pharmaceutical compositions provided herein are formulated in a dosage form for parenteral administration. In yet another embodiment, the pharmaceutical compositions provided herein are formulated in a dosage form for intravenous administration. In yet another embodiment, the pharmaceutical compositions provided herein are formulated in a dosage form for topical administration. In still another embodiment, the pharmaceutical compositions provided herein are formulated in a dosage form for local injection.

In one embodiment, the pharmaceutical compositions provided herein are formulated as a capsule. In one embodiment, the capsule comprises (i) from about 10 mg to about 1,000 mg, from about 25 mg to about 900 mg, from about 50 mg to about 800 mg, from about 100 mg to about 700 mg, from about 200 mg to about 600 mg, from about 300 mg to about 600 mg, or from about 400 mg to about 600 mg of vitamin C, or a pharmaceutically acceptable salt, solvate, or hydrate thereof and (ii) from about 0.1 mg to about 10 mg, from about 1 mg to about 9 mg, from about 2 mg to about 8 mg, from about 3 mg to about 7 mg, or from about 4 mg to about 6 mg of vitamin K, or a single enantiomer, a mixture of enantiomers, or a mixture of diastereomers thereof, or a pharmaceutically acceptable salt, solvate, or hydrate thereof. In another embodiment, the capsule comprises (i) from about 400 mg to about 600 mg of vitamin C, or a pharmaceutically acceptable salt, solvate, or hydrate thereof; and (ii) from about 4 mg to about 6 mg of vitamin K, or a single enantiomer, a mixture of enantiomers, or a mixture of diastereomers thereof, or a pharmaceutically acceptable salt, solvate, or hydrate thereof. In yet another embodiment, the capsule comprises (i) about 200 mg, about 300 mg, about 400, about 500, about 600 mg, about 700 mg, about 800 mg, or about 900 mg of vitamin C, or a pharmaceutically acceptable salt, solvate, or hydrate thereof; and (ii) about 1 mg, about 2 mg, about 3 mg, about 4 mg, about 5 mg, about 6 mg, about 7 mg, about 8 mg, about 9 mg, or about 10 mg of vitamin K, or a single enantiomer, a mixture of enantiomers, or a mixture of diastereomers thereof, or a pharmaceutically acceptable salt, solvate, or hydrate thereof. In still another embodiment, the capsule comprises (i) about 500 mg of vitamin C, or a pharmaceutically acceptable salt, solvate, or hydrate thereof and (ii) about 5 mg of vitamin K, or a single enantiomer, a mixture of enantiomers, or a mixture of diastereomers thereof, or a pharmaceutically acceptable salt, solvate, or hydrate thereof. In certain embodiments, the capsule consists essentially of vitamin C, or a pharmaceutically acceptable salt, solvate, or hydrate thereof and vitamin K, or a single enantiomer, a mixture of enantiomers, or a mixture of diastereomers thereof, or a pharmaceutically acceptable salt, solvate, or hydrate thereof. In certain embodiments, the capsule contains vitamin C, or a pharmaceutically acceptable salt, solvate, or hydrate thereof and vitamin K, or a single enantiomer, a mixture of enantiomers, or a mixture of diastereomers thereof, or a pharmaceutically acceptable salt, solvate, or hydrate thereof.

In one embodiment, vitamin C in the pharmaceutical compositions provided herein is L-ascorbic acid or a pharmaceutically acceptable salt thereof, or a pharmaceutically acceptable solvate or hydrate thereof. In another embodiment, vitamin C in the pharmaceutical compositions provided herein is an alkali or alkaline earth metal salt of L-ascorbic acid, or a pharmaceutically acceptable solvate or hydrate thereof. In yet another embodiment, vitamin C in the pharmaceutical compositions provided herein is sodium, potassium, calcium, or magnesium salt of L-ascorbic acid, or a pharmaceutically acceptable solvate or hydrate thereof. In yet another embodiment, vitamin C in the pharmaceutical compositions provided herein is sodium L-ascorbate. In still another embodiment, vitamin C in the pharmaceutical compositions provided herein is magnesium L-ascorbate.

In one embodiment, vitamin K in the pharmaceutical compositions provided herein is vitamin $K_3$, or a pharmaceutically acceptable salt, solvate, or hydrate thereof. In another embodiment, vitamin K in the pharmaceutical compositions provided herein is 1,2,3,4-tetrahydro-2-methyl-1,4-dioxo-2-naphthalenesulfonic acid, or a pharmaceutically acceptable salt, solvate, or hydrate thereof. In yet another embodiment, vitamin K in the pharmaceutical compositions provided herein is an alkali or alkaline earth metal salt of 1,2,3,4-tetrahydro-2-methyl-1,4-dioxo-2-naphthalenesulfonic acid, or a pharmaceutically acceptable solvate or hydrate thereof. In yet another embodiment, vitamin K in the pharmaceutical compositions provided herein is sodium, potassium, calcium, or magnesium 1,2,3,4-tetrahydro-2-methyl-1,4-dioxo-2-naphthalenesulfonate, or a pharmaceutically acceptable solvate or hydrate thereof. In yet another embodiment, vitamin K in the pharmaceutical compositions provided herein is sodium 1,2,3,4-tetrahydro-2-methyl-1,4-dioxo-2-naphthalenesulfonate, or a pharmaceutically acceptable solvate or hydrate thereof. In yet another embodiment, vitamin K in the pharmaceutical compositions provided herein is potassium 1,2,3,4-tetrahydro-2-methyl-1,4-dioxo-2-naphthalenesulfonate, or a pharmaceutically acceptable solvate or hydrate thereof. In yet another embodiment, vitamin K in the pharmaceutical compositions provided herein is magnesium 1,2,3,4-tetrahydro-2-methyl-1,4-dioxo-2-naphthalenesulfonate, or a pharmaceutically acceptable solvate or hydrate thereof. In yet another embodiment, vitamin K in the pharmaceutical compositions provided herein is sodium 1,2,3,4-tetrahydro-2-methyl-1,4-dioxo-2-naphthalenesulfonate. In yet another embodiment, vitamin K in the pharmaceutical compositions provided herein is anhydrous sodium 1,2,3,4-tetrahydro-2-methyl-1,4-dioxo-2-naphthalenesulfonate. In yet another embodiment, vitamin K in the pharmaceutical compositions provided herein is sodium 1,2,3,4-tetrahydro-2-methyl-1,4-dioxo-2-naphthalenesulfonate hydrate. In still another embodiment, vitamin K in the pharmaceutical compositions provided herein is sodium 1,2,3,4-tetrahydro-2-methyl-1,4-dioxo-2-naphthalenesulfonate trihydrate.

In one embodiment, the capsule contains about 500 mg of sodium L-ascorbate, and about 5 mg of sodium 1,2,3,4-tetrahydro-2-methyl-1,4-dioxo-2-naphthalenesulfonate or a hydrate thereof. In another embodiment, the capsule contains about 500 mg of magnesium L-ascorbate, and about 5 mg of sodium 1,2,3,4-tetrahydro-2-methyl-1,4-dioxo-2-naphthalenesulfonate or hydrate thereof. In yet another embodiment, the capsule contains about 500 mg of sodium L-ascorbate and about 5 mg of anhydrous sodium 1,2,3,4-tetrahydro-2-methyl-1,4-dioxo-2-naphthalenesulfonate. In yet another embodiment, the capsule contains about 500 mg of sodium L-ascorbate and about 5 mg of sodium 1,2,3,4-tetrahydro-2-methyl-1,4-dioxo-2-naphthalenesulfonate trihydrate. In yet another embodiment, the capsule contains about 500 mg of magnesium L-ascorbate and about 5 mg of anhydrous sodium 1,2,3,4-tetrahydro-2-methyl-1,4-dioxo-2-naphthalenesulfonate. In still another embodiment, the capsule contains about 500 mg of magnesium L-ascorbate and about 5 mg of sodium 1,2,3,4-tetrahydro-2-methyl-1,4-dioxo-2-naphthalenesulfonate trihydrate. In another embodiment, the capsules provided herein further comprise a pharmaceutically acceptable vehicle, carrier, diluent, or excipient, or a mixture of two or more thereof.

In one embodiment, the capsule consists essentially of vitamin C, or a pharmaceutically acceptable salt, solvate, or hydrate thereof, in combination with vitamin K, or a single enantiomer, a mixture of enantiomers, or a mixture of diastereomers thereof, or a pharmaceutically acceptable salt, solvate, or hydrate thereof. In certain embodiments, the capsule consists essentially of vitamin C, or a pharmaceutically acceptable salt, solvate, or hydrate thereof, in combination with vitamin $K_3$, or a pharmaceutically acceptable salt, solvate, or hydrate thereof. In one embodiment, the capsule consists essentially of sodium L-ascorbate, and sodium 1,2,3,4-tetrahydro-2-methyl-1,4-dioxo-2-naphthalenesulfonate or a hydrate thereof. In another embodiment, the capsule consists essentially of magnesium L-ascorbate, and sodium 1,2,3,4-tetrahydro-2-methyl-1,4-dioxo-2-naphthalenesulfonate or hydrate thereof. In yet another embodiment, the capsule consists essentially of sodium L-ascorbate and anhydrous sodium 1,2,3,4-tetrahydro-2-methyl-1,4-dioxo-2-naphthalenesulfonate. In yet another embodiment, the capsule consists essentially of sodium L-ascorbate and sodium 1,2,3,4-tetrahydro-2-methyl-1,4-dioxo-2-naphthalenesulfonate trihydrate. In yet another embodiment, the capsule consists essentially of magnesium L-ascorbate and anhydrous sodium 1,2,3,4-tetrahydro-2-methyl-1,4-dioxo-2-naphthalenesulfonate. In still another embodiment, the capsule consists essentially of magnesium L-ascorbate and sodium 1,2,3,4-tetrahydro-2-methyl-1,4-dioxo-2-naphthalenesulfonate trihydrate.

The pharmaceutical compositions provided herein can also be formulated as known to those skilled in the art. Some examples of vitamins C and K containing pharmaceutical compositions are described in U.S. Pat. No. 7,091,241, the disclosure of which is incorporated herein by reference in its entirety.

The pharmaceutical compositions provided herein may be provided in a unit-dosage or multiple-dosage form. A unit-dosage form, as used herein, refers to a physically discrete unit suitable for administration to a subject, e.g., a human and animal subject, and packaged individually as is known in the art. Each unit-dose contains a predetermined quantity of one or more active ingredient(s) sufficient to produce the desired therapeutic effect, optionally in association with one or more pharmaceutical carrier(s) or excipient(s). Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

A. Oral Administration

The pharmaceutical compositions provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gums, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carrier(s) or excipient(s), including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginate, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), and hydroxypropyl methyl cellulose (HPMC); microcrystalline celluloses, such as AVICEL-PH-101, AVICEL-PH-103, AVICEL RC-581, and AVICEL-PH-105 (FMC Corp., Marcus Hook, Pa.); and mixtures of two or more thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures of two or more thereof. The amount of a binder or filler in the pharmaceutical compositions provided herein varies upon the type of formulation, and is readily discernible to those of ordinary skill in the art. The binder or filler may be present from about 50% to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures of two or more thereof. The amount of a disintegrant in the pharmaceutical compositions provided herein varies upon the type of formulation, and is readily discernible to those of ordinary skill in the art. The pharmaceutical compositions provided herein may contain from about 0.5% to about 15% or from about 1% to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures of two or more thereof. The pharmaceutical compositions provided herein may contain from about 0.1% to about 5% by weight of a lubricant.

Suitable glidants include, but are not limited to, colloidal silicon dioxide, CAB-O-SIL® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures of two or more thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic acid, sodium benzoate, and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve several functions, even within the same formulation.

The pharmaceutical compositions provided herein for oral administration can be provided as compressed tablets, tablet triturates, chewable lozenges, rapidly dissolving tablets, multiple compressed tablets, enteric-coated tablets, or sugar-coated or film-coated tablets. In one embodiment, enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of, e.g., a water-soluble material. Film coatings include, but are not limited to, hydroxyethylcellulose, sodium carboxymethylcellulose, polyethylene glycol 4000, and cellulose acetate phthalate. In one embodiment, film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carrier(s) or excipient(s) described herein, including binders, disintegrants, controlled-release polymers, lubricants, diluents, and/or colorants. Flavoring and sweetening agents are useful in the formation of chewable tablets and lozenges.

The pharmaceutical compositions provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including, but not limited to, methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545, each of which is incorporated by reference herein in its entirety. The capsules may also be coated as known by those of skill in the art in order to modify or sustain dissolution of the active ingredient.

The pharmaceutical compositions provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, and polyethylene glycol-750-dimethyl ether, wherein 350, 550, and 750 refer to the approximate average molecular weight of the polyethylene glycol. These formulations can further comprise one or more antioxidants, such as, e.g., butylated hydroxytoluene (BHT), butylated hydroxyanisole (BHA), propyl gallate, vitamin E, hydroquinone, hydroxycoumarins, ethanolamine, lecithin, cephalin, malic acid, sorbitol, phosphoric acid, bisulfite, sodium metabisulfite, thiodipropionic acid and its esters, and dithiocarbamates.

The pharmaceutical compositions provided herein for oral administration can also be provided in the forms of liposomes, micelles, microspheres, or nanosystems. Micellar dosage forms can be prepared as described in U.S. Pat. No. 6,350,458, which is incorporated herein by reference in its entirety.

The pharmaceutical compositions provided herein for oral administration can be provided as non-effervescent or effervescent, granules or powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein for oral administration can be formulated as immediate- or modified-release dosage forms, including delayed-, sustained-, pulsed-, controlled-, targeted-, and programmed-release forms.

B. Parenteral Administration

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, e.g., *Remington: The Science and Practice of Pharmacy*, supra).

The pharmaceutical compositions intended for parenteral administration can include one or more pharmaceutically acceptable carrier(s) and excipient(s), including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including, but not limited to, bisulfite and sodium metabisulfite. Suitable local anesthetics include, but are not limited to, procaine hydrochloride. Suitable suspending and dispersing agents are those as described herein, including, but not limited to, sodium carboxymethylcelluose, hydroxypropyl methylcellulose, and polyvinylpyrrolidone. Suitable emulsifying agents are those described herein, including, but not limited to, polyoxyethylene sorbitan monolaurate, polyoxyethylene sorbitan monooleate 80, and triethanolamine oleate. Suitable sequestering or chelating agents include, but are not limited to, EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

When the pharmaceutical compositions provided herein are formulated for multiple dosage administration, the multiple dosage parenteral formulations contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including, e.g., lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate- or modified-release dosage forms, including, e.g., delayed-, sustained-, pulsed-, controlled-, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include, but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein can be formulated in any dosage forms that are suitable for topical administration for local or systemic effect, including, e.g., emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the pharmaceutical compositions provided herein can also comprise liposomes, micelles, microspheres, nanosystems, and mixtures of two or more thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions can also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein can be provided in the forms of ointments, creams, and gels. Suitable ointment vehicles include, e.g., oleaginous or hydrocarbon vehicles, including lard, benzoinated lard, olive oil, cottonseed oil, and other oils; white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; and emulsion vehicles, either water-in-oil (W/O) emulsions or oil-in-water (O/W) emulsions, including cetyl alcohol, glyceryl monostearate, lanolin, and stearic acid (see, e.g., *Remington: The Science and Practice of Pharmacy*, supra). These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in, e.g., *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including, e.g., bisulfate and sodium metabisulfite. Suitable vehicles include, but are not limited to, cocoa butter (theobroma oil), glycerin-gelatin, carbowax (polyoxyethylene glycol), spermaceti, paraffin, white and yellow wax, appropriate mixtures of mono-, di- and tri-glycerides of fatty acids, and hydrogels, such as polyvinyl alcohol, hydroxyethyl methacrylate, and polyacrylic acid. Combinations of the various vehicles can also be used. Rectal and vaginal suppositories may be prepared by compressing or molding. The typical weight of a rectal and vaginal suppository is about 2 g to about 3 g.

The pharmaceutical compositions provided herein can be administered ophthalmically in the forms of solutions, suspensions, ointments, emulsions, gel-forming solutions, powders for solutions, gels, ocular inserts, and implants.

The pharmaceutical compositions provided herein can be administered intranasally or by inhalation to the respiratory tract. The pharmaceutical compositions can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions can also be provided as a dry powder for insufflation, alone or in combination with an inert carrier such as lactose or phospholipids; and nasal drops. For intranasal use, the powder can comprise a bioadhesive agent, including, e.g., chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein; a propellant as solvent; and/or a surfactant, such as sorbitan trioleate, oleic acid, or an oligolactic acid.

The pharmaceutical compositions provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator can be formulated to contain a powder mix of the pharmaceutical compositions provided herein; a suitable powder base, such as lactose or starch; and a performance modifier, such as L-leucine, mannitol, or magnesium stearate. The lactose may be anhydrous or in the form of a monohydrate. Other suitable excipients or carriers include, but are not limited to, dextran, glucose, maltose, sorbitol, xylitol, fructose, sucrose, and trehalose. The pharmaceutical compositions provided herein for inhaled/intranasal administration can further comprise a suitable flavor, such as menthol and/or levomenthol; and/or sweeteners, such as saccharin and/or saccharin sodium.

The pharmaceutical compositions provided herein for topical administration can be formulated to be immediate-release or modified-release, including delayed-, sustained-, pulsed-, controlled-, targeted-, and programmed-release.

D. Modified Release

The pharmaceutical compositions provided herein can be formulated as a modified release dosage form. As used herein, the term "modified release" refers to a dosage form in which the rate or place of release of the active ingredient(s) is different from that of an immediate-release dosage form when administered by the same route. Modified release dosage forms include, but are not limited to, delayed-, extended-, prolonged-, sustained-, pulsatile-, controlled-, accelerated- or fast-, targeted-, and programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and/or polymorphism of the active ingredient(s).

Examples of modified release include, but are not limited to, those described in U.S. Pat. Nos.: 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500; the contents of which are incorporated by reference herein in their entireties.

1. Matrix Controlled Release Devices

The pharmaceutical compositions provided herein in a modified release dosage form can be fabricated using a matrix controlled release device known to those skilled in the art (see, e.g., Takada et al. in "Encyclopedia of Controlled Drug Delivery," Vol. 2, Mathiowitz Ed., Wiley, 1999).

In certain embodiments, the pharmaceutical compositions provided herein in a modified release dosage form is formulated using an erodible matrix device, which is water-swellable, erodible, or soluble polymers, including, but not limited to, synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethyl hydroxyethyl cellulose (EHEC); polyvinyl pyrrolidone; polyvinyl alcohol; polyvinyl acetate; glycerol fatty acid esters; polyacrylamide;

polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methyl methacrylate, ethyl methacrylate, ethylacrylate, (2-dimethylaminoethyl)methacrylate, and (trimethylaminoethyl)methacrylate chloride.

In certain embodiments, the pharmaceutical compositions provided herein are formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, ethylene/vinyloxyethanol copolymer, polyvinyl chloride, plasticized nylon, plasticized polyethylene terephthalate, natural rubber, silicone rubbers, polydimethylsiloxanes, and silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form can be prepared by methods known to those skilled in the art, including direct compression, dry or wet granulation followed by compression, and melt-granulation followed by compression.

2. Osmotic Controlled Release Devices

The pharmaceutical compositions provided herein in a modified release dosage form can be fabricated using an osmotic controlled release device, including, but not limited to, one-chamber system, two-chamber system, asymmetric membrane technology (AMT), and extruding core system (ECS). In general, such devices have at least two components: (a) a core which contains an active ingredient; and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents is water-swellable hydrophilic polymers, which are also referred to as "osmopolymers" and "hydrogels." Suitable water-swellable hydrophilic polymers as osmotic agents include, but are not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures of two or more thereof.

Osmotic agents of different dissolution rates can be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119, incorporated by reference herein. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220, each of which is incorporated herein by reference.

The total amount of the active ingredient(s) released and the release rate can substantially be modulated via the thickness and porosity of the semipermeable membrane, the composition of the core, and the number, size, and position of the delivery ports.

The pharmaceutical compositions in an osmotic controlled-release dosage form can further comprise additional conventional excipient(s) or carrier(s) as described herein to promote performance or processing of the formulation.

The osmotic controlled-release dosage forms can be prepared according to conventional methods and techniques known to those skilled in the art (see, e.g., *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipient(s) or carrier(s). See, e.g., U.S. Pat. No. 5,612,059 and WO 2002/17918, each of which is incorporated herein by reference. The AMT controlled-release dosage forms can be prepared according to conventional methods and techniques known to those skilled in the art, including, e.g., direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxylethyl cellulose, and other pharmaceutically acceptable excipient(s) or carrier(s).

3. Multiparticulate Controlled Release Devices

The pharmaceutical compositions provided herein in a modified release dosage form can be fabricated as a multiparticulate controlled release device, which comprises a multiplicity of particles, granules, or pellets, ranging from about 10 μm to about 3 mm, from about 50 μm to about 2.5 mm, or from about 100 μm to about 1 mm in diameter. Such multiparticulates can be made by the processes known to those skilled in the art, including, e.g., wet- and dry-granulation, extrusion/spheronization, roller-compaction, and melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein can be blended with the pharmaceutical compositions to aid in processing and forming the multiparticulates. The resulting particles can themselves constitute the multiparticulate device or can be coated by various film-forming materials, such as, enteric polymers, water-swellable, and water-soluble polymers. The multiparticulates can be further processed as a capsule or a tablet.

4. Targeted Delivery

The pharmaceutical compositions provided herein can also be formulated to be targeted to a particular tissue, receptor, or other area of the body of the subject to be treated, including, e.g., liposome-, resealed erythrocyte-, and antibody-based delivery systems. Examples include, but are not limited to, those disclosed in U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874, the contents of which are incorporated by reference herein.

Methods of Use

In one embodiment, provided herein is a method of treating, preventing, or managing an NFκB-mediated condition, disorder, or disease, comprising administering to a subject a therapeutically effective amount of vitamin C, or a pharmaceutically acceptable salt, solvate, or hydrate thereof, in combination with chromium-free vitamin K, or a single enantiomer, a mixture of enantiomers, or a mixture of diastereomers thereof, or a pharmaceutically acceptable salt, solvate, or hydrate thereof.

In another embodiment, provided herein is a method of treating or preventing one or more symptoms of an NFκB-mediated condition, disorder, or disease, comprising administering to a subject a therapeutically effective amount of vitamin C, or a pharmaceutically acceptable salt, solvate, or hydrate thereof, in combination with chromium-free vitamin K, or a single enantiomer, a mixture of enantiomers, or a mixture of diastereomers thereof, or a pharmaceutically acceptable salt, solvate, or hydrate thereof.

In certain embodiments, the methods provided herein provide unexpected and improved results over prior methods. For example, certain commercially available vitamin K (e.g., vitamin $K_3$) contains chromium, in part, due to the methods by which the material is produced (e.g., chromium-containing reagents used in the preparation of vitamin $K_3$). It has been suggested that chromium, not vitamin C and/or vitamin K, in a composition comprising chromium-containing vitamin K, may be responsible for certain therapeutic effects (e.g., anticancer effects). The methods disclosed herein (see, e.g., Example 15, infra) provide that a composition comprising vitamin C and chromium-free vitamin K (e.g., chromium-free vitamin $K_3$) exhibits beneficial therapeutic effects (e.g., an anticancer effect), which could not have been predicted based on the prior art at the time. Moreover, chromium in a composition for use in treating, preventing, or managing a condition, disorder, or disease in a subject may cause toxicity and mutations in the treated subject. Thus, the methods provided herein also provide better safety over prior methods.

In certain embodiments, provided herein is a method of chronic administration of a chromium-free composition of vitamins C and K provided herein to treat a subject (e.g., a subject having an NFκB-mediated condition, disorder, or disease provided herein) over long periods of time.

In one embodiment, the NFκB-mediated condition, disorder, or disease is a proliferative disease.

In certain embodiments, the proliferative disease is cancer, including, but not limited to, head and neck cancer (e.g., originating from lip, oral cavity, oropharynx, hypopharynx, larynx, nasopharynx, nasal cavity, paranasal sinuses, or salivary glands), lung cancer (including small cell lung cancer and non-small cell lung cancer), gastrointestinal tract cancer (including esophageal cancer), gastric cancer, colorectal cancer, anal cancer, pancreatic cancer, liver cancer, gallbladder cancer, extrahepatic bile duct cancer, cancer of the ampulla of vater, breast cancer, gynecologic cancer (including cancer of uterine cervix, cancer of the uterine body, vaginal cancer, vulvar cancer, ovarian cancer, and gestational trophoblastic cancer neoplasia), testicular cancer, urinary tract cancer (including renal cancer), urinary blader cancer, prostate cancer, penile cancer, urethral cancer, neurologic tumors, endocrine neoplasms (including carcinoid and islet cell tumors), pheochromocytoma, adrenal cortical carcinoma, parathyroid carcinoma and metastases to endocrine glands, lymphomas, Burkitt lymphoma, and Zollinger-Ellision syndrome. In certain embodiments, the proliferative disease is a solid tumor. In certain embodiments, the proliferative disease is a blood-borne tumor. In certain embodiments, the proliferative disease is a leukemia. In one embodiment, the leukemia is acute lymphoblastic leukemia (ALL), acute myelogenous leukemia (AML), chronic lymphocytic leukemia (CLL), or chronic myelogenous leukemia (CML). In certain embodiments, the leukemia is related to K562 cell line.

In certain embodiments, the proliferative disease is an inflammatory disease, including, but not limited to, systemic anaphylaxis, hypersensitivity disorders, hypersensitivity lung diseases, cystic fibrosis, atopic dermatitis, urticaria, drug allergies, insect sting allergies, food allergies, celiac disease, mastocytosis, vasculitis, Behcet's syndrome, psoriasis, inflammatory dermatoses, dermatitis, eczema, atopic dermatitis, allergic contact dermatitis, urticaria, autoimmune diseases, tissue transplant rejection, graft rejection, graft-versus-host disease, wound healing, kidney disease, myasthenia gravis, multiple sclerosis, Graves' disease, glomerulonephritis, thyroiditis, diabetes, sarcoidosis, allergic rhinitis, otitis media, allergic conjunctivitis, inflammatory bowel diseases, Crohn's disease, ulcerative colitis (UC), ileitis, enteritis gastritis, helicobacter polori-associated gastritis, systemic lupus erythematosis (SLE), arthritis, rheumatoid arthritis, psoriatic arthritis, rheumatoid arthritis, osteoporosis, asthma, respiratory allergic disease, aseptic osteolysis, systematic informatory response syndrome, chronic obstructive pulmonary disease (COPD), fever, headache, inflammation of the plural cavities, perotonitis, and pleuricy.

In certain embodiments, the NFκB-mediated condition, disorder, or disease is a blood clotting disorder (e.g., sickle cell anemia and hemophilia), acromegaly, adenine nucleotide translocator (ANT) deficiency, age-related macular degeneration (AMD), wet AMD, Alpers syndrome, amenorrhea, amyotrophic lateral sclerosis (ALS), an eating disorder (e.g., obesity, anorexia, and bulimia), ataxia, complex I deficiency, complex II (SDH) deficiency, complex III deficiency, cytochrome c oxidase (COX, complex IV) deficiency, complex V deficiency, Cushing's disease, dwarfism, dysplasia, ectodermal dysplasia, erectile dysfunction, epilepsy, Friedreich's ataxia, flushing, galactorrhea, hot flashes in menopausal and post-menopausal woman, hypogonadism, hyperthyroidism, impotence, gigantism, infertility, muscular degeneration, motor neuron disease, multiple mitochondrial DNA deletion syndrome, MtDNA depletion syndrome, pituitary adenomas, pyruvate dehydrogenase (PDH) deficiency, scoliosis, spina bifida, stress, sudden infant death syndrome, thalassemia, Tourette syndrome, ethylmalonic aciduria with lactic acidemia, 3-methyl glutaconic aciduria with lactic acidemia, refractory epilepsy with declines during infection, Asperger syndrome with declines during infection, autism with declines during infection, attention deficit hyperactivity disorder (ADHD), cerebral palsy with declines during infection, dyslexia with declines during infection, materially inherited thrombocytopenia and leukemia syndrome, Mariah's syndrome (mitrochondrial ataxia, recurrent infections, aphasia, hypouricemia/hypomyelination, seizures, and dicarboxylic aciduria), ND6 dystonia, cyclic vomiting syndrome with declines during infection, 3-hydroxy isobutryic aciduria with lactic acidemia, diabetes mellitus with lactic acidemia, uridine responsive neurologic syndrome (URNS), dilated cardiomyopathy, splenic lymphoma, a bladder disease, a uterine disease, a lymph node disease, or renal tubular acidosis/diabetes/ataxis syndrome.

In certain embodiments, the proliferative disease is an infectious disease, including, but not limited to, bacterial infections, bubonic plague, cerebral palsy, clostridium difficile infections (C-DIF), fungal infections, HIV infection, microbial infections, parasitic diseases, urinary tract infections, viral infections, Arboral virus diseases, food-borne diseases, influenza, measles, mononucleosis, methicillin resistant staphylococcus aureus infections (MRSA), community-acquired-MRSA infections, healthcare-associated-MRSA infections, Leprosy or Hansens disease, mumps, mycotic diseases, papillomavirus infection, pertussis, pneumonia, polio, RLV infection, rubella, SARS, small pox, sepsis, tetanus, vancomycin-resistant enterococci (VRE), and tuberculosis. In certain embodiments, the infectious disease is a microbial infection. In certain embodiments, the infectious disease is a bacterial infection. In certain embodiments, the infectious disease is a viral infection. In certain embodiments, the infectious disease is a fungal infection. In certain embodiments, the infectious disease is a prion disease, including, but not limited to, GSS (Gerstmann-Straussler-Scheinker syndrome), FFI (fatal familial insomnia), Kuru, Alpers syndrome, TME (transmissible mink encephalopathy), and CWD (chronic wasting disease). In certain embodiments, the infectious disease is a sanitation- or hygiene-related disease or recreational water related illnesses.

In another embodiment, the NFκB-mediated condition, disorder, or disease is a sleep disorder, including, but not limited to, sleep apnoea (or sleep apnea), insomnia, narcolepsy, sleep apnea syndrome, and Pickwick Syndrome.

In yet another embodiment, the NFκB-mediated condition, disorder, or disease is a renal disease.

In yet another embodiment, the NFκB-mediated condition, disorder, or disease is a cardiovascular disorder, including, but not limited to, acute heart failure, hypotension, hypertension, angina pectoris, myocardial infarction, cardiomyopathy, heart failure, cardiac hypertrophy, congestive heart failure, atherosclerosis, coronary artery disease, restenosis, and vascular stenosis; or wherein the NFκB-mediated condition, disorder, or disease (e.g., a cardiovascular disorder) is associated with a device, graft, pharmacological, or surgical intervention.

In yet another embodiment, the NFκB-mediated condition, disorder, or disease is a cerebrovascular disorder, including, but not limited to, traumatic brain injury, stroke, ischemia, reperfusion, and ischemic reperfusion injury and aneurysm.

In still another embodiment, the NFκB-mediated condition, disorder, or disease is a gastrointestinal disorder, including, but not limited to, gastritis, ulcers, nausea, pancreatitis, and vomiting.

In certain embodiments, the NFκB-mediated condition, disorder, or disease is a mitochondrial-associated disease, including, but not limited to, AD (Alzheimer's disease), ADPD (Alzheimer's disease and Parkinson's disease), AMDF (ataxia, myoclonus and deafness), auto-immune disease, cancer, CIPO (chronic intestinal pseudoobstruction with myopathy and ophthalmoplegia), congenital muscular dystrophy, CPEO (chronic progressive external ophthalmoplegia), DEAF (maternally inherited deafness or aminoglycoside-induced deafness), DEMCHO (dementia and chorea), diabetes mellitus (type I or type II), DIDMOAD (diabetes insipidus, diabetes mellitus, optic atrophy, deafness), DMDF (diabetes mellitus and deafness), dystonia, exercise intolerance, ESOC (epilepsy, strokes, optic atrophy, and cognitive decline), FBSN (familial bilateral striatal necrosis), FICP (fatal infantile cardiomyopathy plus, a MELAS-associated cardiomyopathy), GER (gastrointestinal reflux), HD (Huntington's disease), KSS (Kearns Sayre syndrome), "later-onset" myopathy, LDYT (Leber's hereditary optic neuropathy and dystonia), Leigh's syndrome, LHON (Leber's hereditary optic neuropathy), LIMM (lethal infantile mitochondrial myopathy), MDM (myopathy and diabetes mellitus), MELAS (mitochondrial encephalomyopathy, lactic acidosis, and stroke-like episodes), MEPR (myoclonic epilepsy and psychomotor regression), MERME (MERRF/MELAS overlap disease), MERRF (myoclonic epilepsy and ragged red muscle fibers), MHCM (maternally inherited hypertrophic cardiomyopathy), MICM (maternally inherited cardiomyopathy), MILS (maternally inherited Leigh's syndrome), mitochondrial encephalocardiomyopathy, mitochondrial encephalomyopathy, MM (mitochondrial myopathy), MMC (maternal myopathy and cardiomyopathy), MNGIE (myopathy and external ophthalmoplegia, neuropathy, gastrointestinal, encephalopathy), multisystem mitochondrial disorder (myopathy, encephalopathy, blindness, hearing loss, peripheral neuropathy), NARP (neurogenic muscle weakness, ataxia, and retinitis pigmentosa), PD (Parkinson's disease), Pearson's syndrome, PEM (progressive encephalopathy), PEO (progressive external ophthalmoplegia), PME (progressive myoclonus epilepsy), PMPS (Pearson marrow-pancreas syndrome), psoriasis, RTT (Rett syndrome), schizophrenia, SIDS (sudden infant death syndrome), SNHL (sensorineural hearing loss), varied familial presentation (clinical manifestations range from spastic paraparesis to multisystem progressive disorder & fatal cardiomyopathy to truncal ataxia, dysarthria, severe hearing loss, mental regression, ptosis, ophthalmoparesis, distal cyclones, and diabetes mellitus), and Wolfram syndrome.

In certain embodiments, the NFκB-mediated condition, disorder, or disease is a neurodegenerative disorder, including, but not limited to, diffuse Lewy body disease, choreaacanthocytosis, primary lateral sclerosis, ocular diseases, ocular neuritis, chemotherapy-induced neuropathies (e.g., vincristine-, paclitaxel-, bortezomib-induced), diabetes-induced neuropathies, Friedreich's ataxia, neuronal loss Creutzfeldt-Jakob disease, BSE (mad cow disease), Scrapie disease, feline spongiform encephalopathy (FSE), Tay-Sachs disease, Sandhoff disease, amniotropic lateral sclerosis (Lou Gehrig's disease), Creutzfeld-Jakob disease, Guillain Barre syndrome and subtypes, and peripheral nervous system neoplasms.

In certain embodiments, the NFκB-mediated condition, disorder, or disease is a cardiovascular disease, including, but not limited to, cardiomyopathy, myocarditis, idiopathic cardiomyopathy, metabolic cardiomyopathy, alcoholic cardiomyopathy, drug-induced cardiomyopathy, ischemic cardiomyopathy, hypertensive cardiomyopathy, and disorders relating to an abnormal level of high density and low density cholesterol (e.g., restenosis).

In certain embodiments, the NFκB-mediated condition, disorder, or disease is an atheromatous disorder of the major blood vessels (macrovascular disease), including, but not limited to, the aorta, the coronary arteries, the carotid arteries, the cerebrovascular arteries, the renal arteries, the iliac arteries, the femoral arteries, and the popliteal arteries; or wherein the NFκB-mediated condition, disorder, or disease (e.g., an atheromatous disorder of the major blood vessels) is associated with a device, graft, pharmacological, or surgical intervention.

In certain embodiments, the NFκB-mediated condition, disorder, or disease is a vascular disease, including, but not limited to, those related to platelet aggregation, the retinal arterioles, the glomerular arterioles, the vasa nervorum, cardiac arterioles, and associated capillary beds of the eye, the kidney, the heart, and the central and peripheral nervous systems.

In certain embodiments, the NFκB-mediated condition, disorder, or disease is a skin disease, including, but not limited to, aging skin (e.g., developing wrinkles or loss of elasticity), dermatitis, contact dermatitis, irritant contact dermatitis, allergic contact dermatitis, atopic dermatitis, allergic eczema, actinic keratosis, keratinization disorders, eczema, epidermolysis bullosa diseases, pemphigus, exfoliative dermatitis, seborrheic dermatitis, erythemas, erythema multiforme, erythema nodosum, damage caused by the sun or other light sources, discoid lupus erythematosus, dermatomyositis, psoriasis, skin cancer, wounds, burns (first-, second-, and third-degree burns, and a thermal, chemical, and electrical burns), alopecia, damages to the skin due to UV light, atrophy of the skin, cellulitis, lichen planus, chronic mucocutaneous disease, and gangrene.

In certain embodiments, the NFκB-mediated condition, disorder, or disease is an eye disease, including, but not limited to, retinitis pigmentosa cataract, graft rejections, ocular disorders, and damage to the optic nerve and retinal, glaucoma, penetrating keratoplasty, acute angle closure glaucoma, chronic angle closure glaucoma, chronic open angle glaucoma, angle recession glaucoma, aphakic glaucoma, pseudophakic glaucoma, drug-induced glaucoma, hyphema, intraocular tumors, juvenile glaucoma, lens-particle glaucoma, low tension glaucoma, malignant glaucoma, neovascular glaucoma, phacolytic glaucoma, phacomorphic glaucoma, pigmentary glaucoma, plateau iris glaucoma, primary congenital glaucoma, primary open angle glaucoma, pseudoexfoliation glaucoma, secondary congenital glaucoma, adult suspect glaucoma, unilateral adult suspect glaucoma, uveitic adult suspect glaucoma, ocular hypertension, ocular hypotony, and Posner-Schlossman syndrome.

In certain embodiments, the NFκB-mediated condition, disorder, or disease is a liver disease, including, but not limited to, acute liver failure, alcoholic liver disease, cystic liver disease, fulminant hepatitis, liver cancer, liver disease in α1-antitrypsin deficiency, and polycystic liver disease.

In certain embodiments, the NFκB-mediated condition, disorder, or disease is a fever, including, but not limited to, puerperal fever, scarlet fever, typhoid fever, rheumatic fever, malaria, March fever, viral hemorrhagic fevers, Ebola fever, dengue fever, yellow fever, drug-induced fever, hyperthermia, east coast fever, malignant catarrhal fever, rift valley fever, classical and African swine fevers, and milk fever.

In certain embodiments, the NFκB-mediated condition, disorder, or disease is a diabetic neuropathy, including, but not limited to, diabetic microvascular injuries, third nerve palsy, mononeuropathy, mononeuritis multiplex, diabetic amyotrophy, painful polyneuropathy, autonomic neuropathy, and thoracoabdominal neuropathy.

In certain embodiments, the NFκB-mediated condition, disorder, or disease is a Charcot Joint or a dental disease, including, but not limited to, Charcot-Marie-tooth disease, gingivitis, periodontitis, gum diseases, thrush, pharyngitis, and sore throat.

In certain embodiments, the NFκB-mediated condition, disorder, or disease is an autoimmune disease, including, but not limited to, organ-tissue autoimmune diseases, Raynaud's syndrome, scleroderma, myasthenia gravis, transplant rejection, endotoxin shock, sepsis, psoriasis, eczema, dermatitis, multiple sclerosis, autoimmune thyroiditis, uveitis, systemic lupus erythematosis, Addison's disease, autoimmune polyglandular disease, autoimmune polyglandular syndrome, and Grave's disease.

In certain embodiments, the NFκB-mediated condition, disorder, or disease is a mitochondrial disorder arising from, for example, but not limited to, post-traumatic head injury and cerebral edema, stroke, Lewy body dementia, hepatorenal syndrome, acute liver failure, NASH (non-alcoholic steatohepatitis), anti-metastasis/pro-differentiation therapy of cancer, idiopathic congestive heart failure, atrial fibrilation (non-valvular), Wolff-Parkinson-White syndrome, idiopathic heart block, prevention of reperfusion injury in acute myocardial infarctions, familial migraines, irritable bowel syndrome, secondary prevention of non-Q wave myocardial infarctions, premenstrual syndrome, prevention of renal failure in hepatorenal syndrome, anti-phospholipid antibody syndrome, eclampsia/pre-eclampsia, oopause infertility, ischemic heart disease/angina, and Shy-Drager and unclassified dysautonomia syndromes.

In certain embodiments, the NFκB-mediated condition, disorder, or disease is a mitochondrial myopathy, including, but not limited to, established syndromes affecting muscle including progressive external ophthalmoplegia, the Kearns-Sayre syndrome (e.g., with ophthalmoplegia, pigmentary retinopathy, cardiac conduction defects, cerebellar ataxia, and sensorineural deafness), the MELAS syndrome (e.g., mitochondrial encephalomyopathy, lactic acidosis, and stroke-like episodes), the MERFF syndrome (e.g., myoclonic epilepsy and ragged red fibers), limb-girdle distribution weakness, and infantile myopathy (e.g., benign, or severe and fatal).

In certain embodiments, the NFκB-mediated condition, disorder, or disease is a muscle disease, including, but not limited to, established syndromes affecting muscle including progressive external ophthalmoplegia, the Kearns-Sayre syndrome (e.g., with ophthalmoplegia, pigmentary retinopathy, cardiac conduction defects, cerebellar ataxia, and sensorineural deafness), the MELAS syndrome (e.g., mitochondrial encephalomyopathy, lactic acidosis, and stroke-like episodes), the MERFF syndrome (e.g., myoclonic epilepsy and ragged red fibers), limb-girdle distribution weakness, and infantile myopathy (e.g., benign, or severe and fatal).

In certain embodiments, the NFκB-mediated condition, disorder, or disease is a lysosomal storage disease, including, but not limited to, neuronal lipidosis, leukodystrophy, mucopolysaccharidosis, storage histiocytosis, GM1 gangliosidosis, GM2 gangliosidosis (Tay-Sachs disease), Niemann-Pick Disease, globoid cell leukodystrophy, Krabbe disease, metachromatic leukodystrophy, Gaucher disease, glycoproteinosis, glycogenosis type II, Pompe disease, and neuronal ceroid lipofuscinosis.

In certain embodiments, the NFκB-mediated condition, disorder, or disease is an ER disease, including, but not limited to, Fabry's disease, cystic fibrosis and associated diseases, A11-antitrypsin deficiency without liver disease, congenital hypothyroidism, thyroglobulin deficiency, thyroid peroxidase deficiency, thyroxin binding globulin deficiency, protein C deficiency, disorders of lipid metabolism, LDL receptor defect, lipoprotein lipase deficiency, lipoprotein(a) deficiency, hereditary hypoparathyroidism, nephrogenic diabetes insipidus due to mutations in AVP receptor 2 or aquaporin-2, growth hormone receptor deficiency, osteogenesis imperfecta, procollagen type I, II, IV deficiency, albinism/tyrosinase deficiency, obesity/elevated prohormone levels: prohormone, convertase 1 deficiency, autosomal dominant neurohypophyseal diabetes insipidus, liver disease in α1-antitrypsin deficiency, Creutzfeldt-Jakob disease, retinitis pigmentosa, combined coagulation factor V and VIII deficiency, ERGIC-53 mutation, and abetalipoproteinemia/deficiency of microsomal triglyceride.

In certain embodiments, the NFκB-mediated condition, disorder, or disease is an inflammatory lung disease, including, but not limited to, pneumoconiosis, anthracosis, coal-worker's pneumoconiosis, black lung, asbestosis, silicosis, grinder's disease, bauxite fibrosis, berylliosis, siderosis, byssinosis, silicosiderosis, and Labrador lung.

In certain embodiments, the NFκB-mediated condition, disorder, or disease is a stomach disease, including, but not limited to, bleeding in the digestive tract, cyclic vomiting syndrome, gastritis, *H. pylori* y Ulcera Peptica (*H. pylori* and peptic ulcer), indigestion, lower GI disease, Menetrier disease, NSAIDs and peptic unlcers, rapid gastric emptying, upper endoscopy, and peptic unlcers.

In certain embodiments, the NFκB-mediated condition, disorder, or disease is a pseudotumor, including, but not limited to, a polycystic disease, a polycystic kidney disease, a polycystic liver disease, and aseptic osteolysis. In some embodiments, the osteolysis is caused by a prosthetic implant in the subject. In some embodiments, the osteolysis is caused by particulate debris from the prosthetic implant in the subject. In some embodiment, the osteolysis is caused by inflammation. In some embodiments, the inflammation is associated with particulate debris from a prosthetic implant in the subject. In some embodiments, the inflammation is associated with a device, graft, pharmacological, or surgical intervention (such as, e.g., following a treatment or intervention involving a stent).

In one embodiment, the NFκB-mediated condition, disorder, or disease is one or more selected from aging, Alzheimer's disease, amyloidosis, angiitis, ankylosing spondylitis, arthrosclerosis, anti-adhesion (prevent surgical adhesions), arrhythmia, arterosclerosis, aseptic osteolysis, asthma, autoimmune diseases with inflammation, avascular necrosis, Bell's palsy, bursitis, cancers, carpal tunnel, celiac disease, chronic fatigue syndrome, colitis, common cold, congenital hip dysplasia, chronic obstructive pulmonary disease (COPD), Crohn's disease, cystic kidney disease, cystic liver disease, dermatitis, diabetes, diabetes type I and II, diverticulitis, endometriosis, exercise intolerance, fibromyalgia, frozen shoulder, gout, Grave's disease, gut diseases, headache, heart failure, hepatitis, herpes, HIV, HIV infections, HIV-associated rheumatoid diseases, infectious arthritis, inflammation, inflammatory bowel, ischemia, lupus, Lyme disease, migraine treatment, multiple sclerosis, muscular dystrophy, nephritis, neuropathological diseases, neuropathy, ocular diseases, osteolytic arthritis, organ/tissue transplant, osteolysis, osteopenia, osteoporosis, Paget's disease, Parkinson's disease, pelvic inflammatory disease, pigment diseases, polycystic kidney disease, polycystic liver disease, pseudotumors, psoriatic arthritis, pseudogout, rheumatoid arthritis, renal diseases, sarcodosis, scleraderma, scurvy, sepsis, skin diseases, sleep apnoea (or sleep apnea), space travel (e.g., bone density disorder), tendonitis, thyroid associated arthritis, transfection procedures, ulcerative colitis, ulcers, viral infection, warts, and wound healing.

In certain embodiments, the NFκB-mediated condition, disorder, or disease is aging. In certain embodiments, the NFκB-mediated condition, disorder, or disease is Alzheimer's disease. In certain embodiments, the NFκB-mediated condition, disorder, or disease is amyloidosis. In certain embodiments, the NFκB-mediated condition, disorder, or disease is angiitis. In certain embodiments, the NFκB-mediated condition, disorder, or disease is ankylosing spondylitis. In certain embodiments, the NFκB-mediated condition, disorder, or disease is anthrosclerosis. In certain embodiments, the NFκB-mediated condition, disorder, or disease is adhesion or anti-adhesion (e.g., prevent surgical adhesions). In certain embodiments, the NFκB-mediated condition, disorder, or disease is arrhythmia. In certain embodiments, the NFκB-mediated condition, disorder, or disease is aseptic osteolysis. In certain embodiments, the NFκB-mediated condition, disorder, or disease is asthma. In certain embodiments, the NFκB-mediated condition, disorder, or disease is an autoimmune disease. In certain embodiments, the NFκB-mediated condition, disorder, or disease is avascular necrosis. In certain embodiments, the NFκB-mediated condition, disorder, or disease is Bell's palsy. In certain embodiments, the NFκB-mediated condition, disorder, or disease is bursitis. In certain embodiments, the NFκB-mediated condition, disorder, or disease is cancer. In certain embodiments, the NFκB-mediated condition, disorder, or disease is carpal tunnel. In certain embodiments, the NFκB-mediated condition, disorder, or disease is a celiac disease. In certain embodiments, the NFκB-mediated condition, disorder, or disease is chronic fatigue syndrome. In certain embodiments, the NFκB-mediated condition, disorder, or disease is colitis. In certain embodiments, the NFκB-mediated condition, disorder, or disease is common cold. In certain embodiments, the NFκB-mediated condition, disorder, or disease is congenital hip dysplasia. In certain embodiments, the NFκB-mediated condition, disorder, or disease is chronic obstructive pulmonary disease (COPD). In certain embodiments, the NFκB-mediated condition, disorder, or disease is Crohn's disease. In certain embodiments, the NFκB-mediated condition, disorder, or disease is a liver disease. In certain embodiments, the NFκB-mediated condition, disorder, or disease is a kidney disease. In certain embodiments, the kidney disease is polycystic kidney disease. In certain embodiments, the NFκB-mediated condition, disorder, or disease is cystic kidney disease. In certain embodiments, the NFκB-mediated condition, disorder, or disease is cystic liver disease. In certain embodiments, the liver disease is polycystic liver disease. In certain embodiments, the NFκB-mediated condition, disorder, or disease is dermatitis. In certain embodiments, the NFκB-mediated condition, disorder, or disease is diabetes. In certain embodiments, the NFκB-mediated condition, disorder, or disease is diabetes type I. In certain embodiments, the NFκB-mediated condition, disorder, or disease is diabetes type II. In certain embodiments, the NFκB-mediated condition, disorder, or disease is diverticulitis. In certain embodiments, the NFκB-mediated condition, disorder, or disease is endometriosis. In certain embodiments, the NFκB-mediated condition, disorder, or disease is exercise intolerance. In certain embodiments, the NFκB-mediated condition, disorder, or disease is fibromyalgia. In certain embodiments, the NFκB-mediated condition, disorder, or disease is frozen shoulder. In certain embodiments, the NFκB-mediated condition, disorder, or disease is gout. In certain embodiments, the NFκB-mediated condition, disorder, or disease is Grave's disease. In certain embodiments, the NFκB-mediated condition, disorder, or disease is a gut disease. In certain embodiments, the NFκB-mediated condition, disorder, or disease is headache. In certain embodiments, the NFκB-mediated condition, disorder, or disease is heart failure. In certain embodiments, the NFκB-mediated condition, disorder, or disease is hepatitis. In certain embodiments, the NFκB-mediated condition, disorder, or disease is herpes. In certain embodiments, the NFκB-mediated condition, disorder, or disease is HIV. In certain embodiments, the NFκB-mediated condition, disorder, or disease is HIV-associated rheumatoid disease. In certain embodiments, the NFκB-mediated condition, disorder, or disease is infectious arthritis. In certain embodiments, the NFκB-mediated condition, disorder, or disease is inflammation. In certain embodiments, the NFκB-mediated condition, disorder, or disease is inflammatory bowel. In certain embodiments, the NFκB-mediated condition, disorder, or disease is ischemia. In certain embodiments, the NFκB-mediated condition, disorder, or disease is lupus. In certain embodiments, the NFκB-mediated condition, disorder, or disease is Lyme disease. In certain embodiments, the NFκB-mediated condition, disorder, or disease is migraine (e.g., migraine treatment). In certain embodiments, the NFκB-mediated condition, disorder, or disease is multiple sclerosis. In certain embodiments, the NFκB-mediated condition, disorder, or disease is muscular dystrophy. In certain embodiments, the NFκB-mediated condition, disorder, or disease is nephritis. In certain embodiments, the NFκB-mediated condition, disorder, or disease is a neuropathological disease. In certain embodiments, the NFκB-mediated condition, disorder, or disease is neuropathy. In certain embodiments, the NFκB-mediated condition, disorder, or disease is ocular disease. In certain embodiments, the NFκB-mediated condition, disorder, or disease is osteolytic arthritis. In certain embodiments, the NFκB-mediated condition, disorder, or disease is organ/tissue transplant. In certain embodiments, the NFκB-mediated condition, disorder, or disease is osteolysis. In certain embodiments, the NFκB-mediated condition, disorder, or disease is osteopenia. In certain embodiments, the NFκB-mediated condition, disorder, or disease is osteoporosis. In certain embodiments, the NFκB-mediated condition, disorder, or disease is Paget's disease. In certain embodiments, the NFκB-mediated condition, disorder, or disease is Parkinson's disease. In certain embodiments, the NFκB-mediated condition, disorder, or disease is pelvic inflammatory disease. In certain embodiments, the NFκB-mediated condition, disorder, or disease is a pigment disease. In certain embodiments, the NFκB-mediated condition, disorder, or disease is a polycystic disease. In certain embodiments, the polycystic disease is polycystic kidney disease. In certain embodiments, the polycystic disease is polycystic liver disease. In certain embodiments, the NFκB-mediated condition, disorder, or disease is pseudotumor. In certain embodiments, the pseudotumor is aseptic osteolysis. In certain embodiments, the pseudotumor is polycystic kidney disease. In certain embodiments, the pseudotumor is polycystic liver disease. In certain embodiments, the pseudotumor is aseptic osteolysis. In certain embodiments, the NFκB-mediated condition, disorder, or disease is psoriatic arthritis. In certain embodiments, the NFκB-mediated condition, disorder, or disease is pseudogout. In certain embodiments, the NFκB-mediated condition, disorder, or disease is rheumatoid arthritis. In certain embodiments, the NFκB-mediated condition, disorder, or disease is a renal disease. In certain embodiments, the NFκB-mediated condition, disorder, or disease is sarcodosis. In certain embodiments, the NFκB-mediated condition, disorder, or disease is scleraderma. In certain embodiments, the NFκB-mediated condition, disorder, or disease is scurvy. In certain embodiments, the NFκB-mediated condition, disorder, or disease is sepsis. In certain embodiments, the NFκB-mediated condition, disorder, or disease is a skin disease. In certain embodiments, the NFκB-mediated condition, disorder, or disease is sleep apnoea (or sleep apnea). In certain embodiments, the NFκB-mediated condition, disorder, or disease is space travel (e.g., bone density disorder). In certain embodiments, the NFκB-mediated condition, disorder, or disease is tendonitis. In certain embodiments, the NFκB-mediated condition, disorder, or disease is thyroid associated arthritis. In certain embodiments, the NFκB-mediated condition, disorder, or disease is a transfection procedure. In certain embodiments, the NFκB-mediated condition, disorder, or disease is ulcerative colitis. In certain embodiments, the NFκB-mediated condition, disorder, or disease is ulcer. In certain embodiments, the NFκB-mediated condition, disorder, or disease is viral infection. In certain embodiments, the NFκB-mediated condition, disorder, or disease is a wart. In certain embodiments, the NFκB-mediated condition, disorder, or disease is wound healing.

In one embodiment, the NFκB-mediated condition, disorder, or disease is osteolysis. In one embodiment, the osteolysis is aseptic osteolysis. In another embodiment, the osteolysis is caused by inflammation. In yet another embodiment, the osteolysis is caused by a prosthetic implant in the subject. In yet another embodiment, the osteolysis is caused by particulate debris from the prosthetic implant in the subject.

In certain embodiments, the combination of vitamins C and K has a synergetic effect in treating, preventing, or managing an NFκB-mediated condition, disorder, or disease, when compared to the administration of vitamin C or K alone. In certain embodiments, the combination of vitamin C (in one embodiment, sodium or magnesium L-ascorbate) and vitamin $K_3$ (in one embodiment, sodium 1,2,3,4-tetrahydro-2-methyl-1,4-dioxo-2-naphthalenesulfonate) has a synergetic effect in treating, preventing, or managing an NFκB-mediated condition, disorder, or disease when compared to the administration of vitamin C or $K_3$ alone.

Without being limited by any theory, a synergistic effect of the combination of vitamins C and K permits the use of lower dosages of vitamin C and/or K, and/or less frequent administration of the combination to a subject with a condition, disorder, or disease. The ability to utilize lower dosages of the combination (e.g., a prophylactic or therapeutic agent) and/or to administer the combination less frequently reduces the toxicity associated with the administration of the combination to a subject without reducing the efficacy of the combination in the prevention or treatment of a condition, disorder, or disease. In addition, a synergistic effect can result in improved efficacy of vitamin C and/or K in the prevention or treatment of a condition, disorder, or disease. Furthermore, a synergistic effect of the combination may avoid or reduce adverse or unwanted side effects associated with the use of either vitamin C or K alone.

In another embodiment, the NFκB-mediated condition, disorder, or disease is inflammation. In one embodiment, the inflammation is associated with particulate debris from the prosthetic implant in the subject. In certain embodiments, the combination of vitamins C and K has a synergetic effect in treating, preventing, or managing inflammation associated with the prosthetic implant when compared to the administration of vitamin C or K alone. In certain embodiments, the combination of vitamin C (in one embodiment, sodium or magnesium L-ascorbate) and vitamin $K_3$ (in one embodiment, sodium 1,2,3,4-tetrahydro-2-methyl-1,4-dioxo-2-naphthalenesulfonate) has a synergetic effect in treating, preventing, or managing inflammation associated with a prosthetic implant when compared to the administration of vitamin C or $K_3$ alone.

In yet another embodiment, provided herein is a method of treating hip or joint disorder in a subject, which comprises surgically replacing the hip or joint of the subject, and chronically administering to the subject a therapeutically effective amount of vitamin C, or a pharmaceutically acceptable salt, solvate, or hydrate thereof, in combination with chromium-free vitamin K, or a single enantiomer, a mixture of enantiomers, or a mixture of diastereomers thereof, or a pharmaceutically acceptable salt, solvate, or hydrate thereof.

In yet another embodiment, provided herein is a method of treating, preventing, or managing inflammation caused by a prosthetic implant in a subject, comprising administering to the subject a therapeutically effective amount of vitamin C, or a pharmaceutically acceptable salt, solvate, or hydrate thereof, in combination with chromium-free vitamin K, or a single enantiomer, a mixture of enantiomers, or a mixture of diastereomers thereof, or a pharmaceutically acceptable salt, solvate, or hydrate thereof. In one embodiment, the inflammation is caused by particulate debris from the prosthetic implant in the subject. In certain embodiments, the combination of vitamins C and K has a synergetic effect in treating, preventing, or managing inflammation caused by the prosthetic implant when compared to the administration of vitamin C or K alone. In certain embodiments, the combination of vitamin C (in one embodiment, sodium or magnesium L-ascorbate) and vitamin $K_3$ (in one embodiment, sodium 1,2,3,4-tetrahydro-2-methyl-1,4-dioxo-2-naphthalenesulfonate) has a synergetic effect in treating, preventing, or managing inflammation caused by a prosthetic implant when compared to the administration of vitamin C or $K_3$ alone.

In yet another embodiment, provided herein is a method of increasing the functional life of a prosthetic implant in a subject, comprising administering to the subject a therapeutically effective amount of vitamin C, or a pharmaceutically acceptable salt, solvate, or hydrate thereof, in combination with chromium-free vitamin K, or a single enantiomer, a mixture of enantiomers, or a mixture of diastereomers thereof, or a pharmaceutically acceptable salt, solvate, or hydrate thereof. In certain embodiments, the combination of vitamins C and K has a synergetic effect in increasing the functional life of the prosthetic implant when compared to the administration of vitamin C or K alone. In certain embodiments, the combination of vitamin C (in one embodiment, sodium or magnesium L-ascorbate) and vitamin $K_3$ (in one embodiment, sodium 1,2,3,4-tetrahydro-2-methyl-1,4-dioxo-2-naphthalenesulfonate) has a synergetic effect in increasing the functional life of the prosthetic implant when compared to the administration of vitamin C or K₃ alone.

In still another embodiment, provided herein is a method of treating, preventing, or managing NFκB-mediated condition, disorder, or disease caused by a prosthetic implant in a subject, comprising administering to the subject a therapeutically effective amount of vitamin C, or a pharmaceutically acceptable salt, solvate, or hydrate thereof, in combination with vitamin K, or a single enantiomer, a mixture of enantiomers, or a mixture of diastereomers thereof, or a pharmaceutically acceptable salt, solvate, or hydrate thereof. In certain embodiments, the method of treating, preventing, or managing NFκB-mediated condition, disorder, or disease is caused by particulate debris from a prosthetic implant in the subject. In certain embodiments, the combination of vitamins C and K has a synergetic effect in treating, preventing, or managing NFκB-mediated condition, disorder, or disease in a subject when compared to the administration of vitamin C or K alone. In certain embodiments, the combination of vitamin C (in one embodiment, sodium or magnesium L-ascorbate) and vitamin K₃ (in one embodiment, sodium 1,2,3,4-tetrahydro-2-methyl-1,4-dioxo-2-naphthalenesulfonate) has a synergetic effect in treating, preventing, or managing NFκB-mediated condition, disorder, or disease in a subject when compared to the administration of vitamin C or K₃ alone.

In one embodiment, provided herein is a method for treating, preventing, or ameliorating a polycystic disease in a subject, comprising administering to the subject vitamin C, or a pharmaceutically acceptable salt, solvate, or hydrate thereof and vitamin K, or a single enantiomer, a mixture of enantiomers, or a mixture of diastereomers thereof, or a pharmaceutically acceptable salt, solvate, or hydrate thereof.

In certain embodiments, the polycystic disease is a polycystic kidney disease, a polycystic liver disease, a polycystic pancreas disease, a polycystic ovarian syndrome, or a combination thereof.

In certain embodiments, the polycystic disease is a polycystic kidney disease. In certain embodiments, the polycystic kidney disease is an autosomal dominant polycystic kidney disease (ADPKD) or an autosomal recessive polycystic kidney disease (ARPKD).

In certain embodiments, the polycystic kidney disease is ADPKD. In certain embodiments, ADPKD is caused by one or more mutations in PKD1, PKD2, and/or PKD3. In certain embodiments, ADPKD is caused by a mutation in PKD1. In certain embodiments, ADPKD is caused by a mutation in PKD2. In certain embodiments, ADPKD is caused by a mutation in PKD3.

In certain embodiments, the polycystic kidney disease is ARPKD. In certain embodiments, ARPKD is caused by one or more mutations in PKHD1. In certain embodiments, ARPKD is caused by a mutation in PKHD1.

In certain embodiments, the polycystic disease is a polycystic liver disease (PLD). In certain embodiments, the PLD is an isolated PLD. In certain embodiments, the PLD is an autosomal dominant polycystic liver disease (ADPLD). In certain embodiments, the PLD is an isolated ADPLD. In certain embodiments, the PLD is caused by one or more mutations in PPRKCSH and/or SEC63. In certain embodiments, the PLD is caused by a mutation in PPRKCSH. In certain embodiments, the PLD is caused by a mutation in SEC63. In certain embodiments, the PLD is associated with ARPKD. In certain embodiments, the PLD is associated with ADPKD.

In certain embodiments, the polycystic disease is a polycystic kidney disease and a polycystic liver disease.

In certain embodiments, the polycystic disease is a polycystic pancreas disease. In certain embodiments, the polycystic disease is a polycystic ovarian syndrome.

In another embodiment, provided herein is a method for treating, preventing, or ameliorating a polycystic kidney disease in a subject, comprising administering to the subject vitamin C, or a pharmaceutically acceptable salt, solvate, or hydrate thereof; and vitamin K, or a single enantiomer, a mixture of enantiomers, or a mixture of diastereomers thereof, or a pharmaceutically acceptable salt, solvate, or hydrate thereof.

In yet another embodiment, provided herein is a method for treating, preventing, or ameliorating a polycystic liver disease in a subject, comprising administering to the subject vitamin C, or a pharmaceutically acceptable salt, solvate, or hydrate thereof; and vitamin K, or a single enantiomer, a mixture of enantiomers, or a mixture of diastereomers thereof, or a pharmaceutically acceptable salt, solvate, or hydrate thereof.

In certain embodiments, the combination of vitamins C and K has a synergetic effect in treating, preventing, or ameliorating one or more symptoms of a polycystic disease as compared to the administration of either compound alone. In certain embodiments, the combination of sodium or magnesium L-ascorbate and sodium 1,2,3,4-tetrahydro-2-methyl-1,4-dioxo-2-naphthalenesulfonate has a synergetic effect in treating, preventing, or ameliorating one or more symptoms of a polycystic disease as compared to the administration of either compound alone.

Without being limited by any theory, a synergistic effect of the combination of vitamins C and K permits the use of lower dosages of vitamin C and/or K, and/or less frequent administration of the combination to a subject having a polycystic disease. The ability to utilize lower dosages of the combination and/or to administer the combination less frequently reduces the toxicity associated with the administration of the combination to a subject without reducing the efficacy of the combination in treating, preventing, or ameliorating one or more symptoms of a polycystic disease. In addition, a synergistic effect can result in improved efficacy of vitamin C and/or K in treating, preventing, or ameliorating one or more symptoms of a polycystic disease. Furthermore, a synergistic effect of the combination may avoid or reduce adverse or unwanted side effects associated with the use of either vitamin C or K alone.

Vitamin C and/or vitamin K as used in the methods provided herein can be delivered as a single dose such as, e.g., as a single bolus injection, or as a single oral tablet or pill.

In one embodiment, vitamins C and K as used in the methods provided herein are formulated in a single unit dosage form. In one embodiment, vitamins C and K as used in the methods provided herein are formulated together in a tablet. In one embodiment, vitamins C and K as used in the methods provided herein are formulated together in a capsule. In one embodiment, vitamins C and K as used in the methods provided herein are formulated together as an oral, parenteral, or intravenous dosage form. In another embodiment, vitamins C and K are each formulated separately in its own single unit dosage form. In one embodiment, vitamins C and K are formulated in a pharmaceutical composition as discussed herein.

In certain embodiments, a capsule as used in the methods provided herein contains about 500 mg of vitamin C, or a pharmaceutically acceptable salt, solvate, or hydrate thereof; and about 5 mg of chromium-free vitamin K, or a single enantiomer, a mixture of enantiomers, or a mixture of diastereomers thereof, or a pharmaceutically acceptable salt, solvate, or hydrate thereof. In certain embodiments, a capsule as used in the methods provided herein consists essentially of vitamin C, or a pharmaceutically acceptable salt, solvate, or hydrate thereof, in combination with chromium-free vitamin K, or a single enantiomer, a mixture of enantiomers, or a mixture of diastereomers thereof, or a pharmaceutically acceptable salt, solvate, or hydrate thereof.

In certain embodiments, vitamin K as used in the methods provided herein is chromium-free vitamin K. In certain embodiments, the chromium-free vitamin K as used in the methods provided herein is chromium-free vitamin $K_3$. In certain embodiments, the chromium-free vitamin $K_3$ as used in the methods provided herein is 1,2,3,4-tetrahydro-2-methyl-1,4-dioxo-2-naphthalenesulfonic acid or a pharmaceutically acceptable salt thereof; or a pharmaceutically acceptable solvate or hydrate thereof. In certain embodiments, the chromium-free vitamin $K_3$ as used in the methods provided herein is an alkali or alkaline earth metal salt of 1,2,3,4-tetrahydro-2-methyl-1,4-dioxo-2-naphthalenesulfonic acid, or a pharmaceutically acceptable solvate or hydrate thereof. In certain embodiments, the chromium-free vitamin $K_3$ as used in the methods provided herein is sodium or magnesium 1,2,3,4-tetrahydro-2-methyl-1,4-dioxo-2-naphthalenesulfonate, or a pharmaceutically acceptable solvate or hydrate thereof. In certain embodiments, the chromium-free vitamin $K_3$ as used in the methods provided herein is anhydrous sodium 1,2,3,4-tetrahydro-2-methyl-1,4-dioxo-2-naphthalenesulfonate.

In certain embodiments, vitamin C as used in the methods provided herein is L-ascorbic acid or a pharmaceutically acceptable salt thereof, or a pharmaceutically acceptable solvate or hydrate thereof. In certain embodiments, the vitamin C as used in the methods provided herein is an alkali or alkaline earth metal salt of L-ascorbic acid, or a pharmaceutically acceptable solvate or hydrate thereof. In certain embodiments, the vitamin C as used in the methods provided herein is sodium L-ascorbate, or a pharmaceutically acceptable solvate or hydrate thereof. In certain embodiments, the vitamin C as used in the methods provided herein is magnesium L-ascorbate, or a pharmaceutically acceptable solvate or hydrate thereof.

In certain embodiments, the molar ratio of vitamin C to vitamin K as used in the methods provided herein is ranging from about 50 to about 500. In certain embodiments, the molar ratio of vitamin C to chromium-free vitamin K as used in the methods provided herein is ranging from about 50 to about 500.

In certain embodiments, the molar ratio of vitamin C to vitamin K as used in the methods provided herein is about 100. In certain embodiments, the molar ratio of vitamin C to chromium-free vitamin K as used in the methods provided herein is about 100.

In certain embodiments, vitamin C and/or vitamin K as used in the methods provided herein can be administered over time, such as, e.g., continuous infusion over time or divided bolus doses over time.

In one embodiment, vitamin C and/or vitamin K as used in the methods provided herein can be administered once daily (QD), or divided into multiple daily doses such as twice daily (BID), three times daily (TID), four times daily (QID), five times daily, six times daily, seven times daily, eight times daily, nine times daily, or ten times daily. In one embodiment, vitamin C as used in the methods provided herein can be administered once daily (QD), or divided into multiple daily doses such as twice daily (BID), three times daily (TID), four times daily (QID), five times daily, six times daily, seven times daily, eight times daily, nine times daily, or ten times daily. In one embodiment, vitamin K as used in the methods provided herein can be administered once daily (QD), or divided into multiple daily doses such as twice daily (BID), three times daily (TID), four times daily (QID), five times daily, six times daily, seven times daily, eight times daily, nine times daily, or ten times daily. In some embodiments, vitamin C and/or vitamin K as used in the methods provided herein is(are) administered twice a day. In addition, the administration can be continuous, i.e., every day, or intermittently. The term "intermittent" or "intermittently" as used herein is intended to mean stopping and starting at either regular or irregular intervals. For example, intermittent administration of the compound provided herein is administration for one to six days per week, administration in cycles (e.g., daily administration for two to eight consecutive weeks, then a rest period with no administration for up to, e.g., one week), or administration on alternate days.

In certain embodiments, vitamin C and/or vitamin K as used in the methods provided herein is(are) administered from about 1 to about 20 times a day, from about 1 to about 15 times a day, from about 1 to about 10 times a day, or from about 1 to about 5 times a day. In certain embodiments, vitamin C and/or vitamin K as used in the methods provided herein is(are) administered every 1 to 10 hour(s), every 2 to 8 hours, every 3 to 7 hours, every 4 to 6 hours, or every 5 to 6 hours. In certain embodiments, vitamin C and/or vitamin K as used in the methods provided herein is(are) administered every hour, every 2 hours, every 3 hours, every 4 hours, every 5 hours, every 6 hours, every 7 hours, every 8 hours, every 9 hours, or every 10 hours. In certain embodiments, vitamin C and/or vitamin K as used in the methods provided herein is(are) administered once a day. In certain embodiments, vitamin C and/or vitamin K as used in the methods provided herein is(are) administered 5 times a day. In certain embodiments, vitamin C and/or vitamin K as used in the methods provided herein is(are) administered 10 times a day. In certain embodiments, vitamin C and/or vitamin K as used in the methods provided herein is(are) administered every 4, 5, or 6 hours.

In certain embodiments, vitamin C as used in the methods provided herein is administered to the subject in an amount ranging from about 1 to about 1,000 mg/kg/day, from about 5 to about 500 mg/kg/day, or from about 10 to about 100 mg/kg/day. In certain embodiments, vitamin C as used in the methods provided herein is administered to the subject in an amount of about 10 mg/kg/day, about 20 mg/kg/day, about 30 mg/kg/day, about 40 mg/kg/day, about 50 mg/kg/day, about 60 mg/kg/day, about 70 mg/kg/day, about 80 mg/kg/day, about 90 mg/kg/day, about 100 mg/kg/day, about 200 mg/kg/day, about 300 mg/kg/day, about 400 mg/kg/day, or about 500 mg/kg/day.

In certain embodiments, vitamin K as used in the methods provided herein is administered to the subject in an amount ranging from about 0.01 to about 50 mg/kg/day, from about 0.015 to about 50 mg/kg/day, from about 0.05 to about 40 mg/kg/day, from about 0.2 to about 30 mg/kg/day, or from about 10 to about 30 mg/kg/day. In certain embodiments, vitamin K as used in the methods provided herein is administered to the subject in an amount of about 0.015 mg/kg/day, about 5 mg/kg/day, about 25 mg/kg/day, or about 30 mg/kg/day.

The administered dose of vitamin C and/or vitamin K can also be expressed in units other than the unit "mg/kg/day" or "g/kg/day." For example, doses for parenteral administration can be expressed as $mg/m^2/day$. One of ordinary skill in the art would readily know how to convert doses from mg/kg/day to mg/m²/day, given either the height or weight of a subject or both (See, e.g., www.fda.gov/cder/cancer/animal-frame.htm).

In certain embodiments, vitamin C as used in the methods provided herein is administered to the subject in an amount ranging from about 0.1 g to about 3 g every four hours. In certain embodiments, vitamin K as used in the methods provided herein is administered to the subject in an amount ranging from about 0.2 mg to about 300 mg every four hours.

In certain embodiments, vitamin C as used in the methods provided herein is administered to the subject in an amount ranging from about 500 mg to about 3,000 mg a day. In certain embodiments, vitamin K as used in the methods provided herein is administered to the subject in an amount ranging from about 3 mg to about 30 mg a day. In certain embodiments, vitamin C as used in the methods provided herein is administered to the subject in an amount ranging from about 500 mg to about 10,000 mg a day. In certain embodiments, vitamin K as used in the methods provided herein is administered to the subject in an amount ranging from about 3 mg to about 100 mg a day. In certain embodiments, vitamin C as used in the methods provided herein is administered to the subject in an amount of greater than about 500 mg a day. In certain embodiments, vitamin K as used in the methods provided herein is administered to the subject in an amount of greater than about 3 mg a day. In certain embodiments, vitamin C as used in the methods provided herein is administered to the subject in an amount up to about 10,000 mg a day. In certain embodiments, vitamin K as used in the methods provided herein is administered to the subject in an amount up to about 100 mg a day. In certain embodiments, vitamin C as used in the methods provided herein is administered to the subject in an amount up to about 20,000 mg a day. In certain embodiments, vitamin K as used in the methods provided herein is administered to the subject in an amount up to about 200 mg a day. In certain embodiments, vitamin C as used in the methods provided herein is administered to the subject in an amount up to about 30,000 mg a day. In certain embodiments, vitamin K as used in the methods provided herein is administered to the subject in an amount up to about 300 mg a day. In certain embodiments, vitamin C as used in the methods provided herein is administered to the subject in an amount up to about 40,000 mg a day. In certain embodiments, vitamin K as used in the methods provided herein is administered to the subject in an amount up to about 400 mg a day. In certain embodiments, vitamin C as used in the methods provided herein is administered to the subject in an amount up to about 50,000 mg a day. In certain embodiments, vitamin K as used in the methods provided herein is administered to the subject in an amount up to about 500 mg a day. In certain embodiments, vitamin C as used in the methods provided herein is administered to the subject in an amount up to about 60,000 mg a day. In certain embodiments, vitamin K as used in the methods provided herein is administered to the subject in an amount up to about 600 mg a day. In certain embodiments, vitamin C as used in the methods provided herein is administered to the subject in an amount up to about 70,000 mg a day. In certain embodiments, vitamin K as used in the methods provided herein is administered to the subject in an amount up to about 700 mg a day. In certain embodiments, vitamin C as used in the methods provided herein is administered to the subject in an amount up to about 80,000 mg a day. In certain embodiments, vitamin K as used in the methods provided herein is administered to the subject in an amount up to about 800 mg a day. In certain embodiments, vitamin C as used in the methods provided herein is administered to the subject in an amount up to about 90,000 mg a day. In certain embodiments, vitamin K as used in the methods provided herein is administered to the subject in an amount up to about 900 mg a day. In certain embodiments, vitamin C as used in the methods provided herein is administered to the subject in an amount up to about 100,000 mg a day. In certain embodiments, vitamin K as used in the methods provided herein is administered to the subject in an amount up to about 1,000 mg a day. In certain embodiments, vitamin C as used in the methods provided herein is administered to the subject in an amount up to about 200,000 mg a day. In certain embodiments, vitamin K as used in the methods provided herein is administered to the subject in an amount up to about 2,000 mg a day.

In certain embodiments, vitamin C as used in the methods provided herein is administered to the subject in an amount ranging from about 2,000 mg to about 3,000 mg a day; and vitamin K is administered to the subject in an amount ranging from about 12 mg to about 19 mg a day. In certain embodiments, vitamin C as used in the methods provided herein is administered to the subject in an amount ranging from about 2,000 mg to about 3,000 mg a day; and vitamin K is administered to the subject in an amount ranging from about 20 mg to about 30 mg a day.

In certain embodiments, vitamin C as used in the methods provided herein is administered to the subject in an amount of about 2,000 mg a day; and vitamin K is administered to the subject in an amount of about 12 mg a day. In certain embodiments, vitamin C as used in the methods provided herein is administered to the subject in an amount of about 3,000 mg a day; and vitamin K is administered to the subject in an amount of about 19 mg a day.

In certain embodiments, vitamin C as used in the methods provided herein is administered to the subject in an amount of about 2,000 mg a day; and vitamin K is administered to the subject in an amount of about 20 mg a day. In certain embodiments, vitamin C as used in the methods provided herein is administered to the subject in an amount of about 3,000 mg a day; and vitamin K is administered to the subject in an amount of about 30 mg a day.

In certain embodiments, vitamins C and K are administered as one or more capsules, each comprising about 500 mg of sodium L-ascorbate and about 3 mg of sodium 1,2,3,4-tetrahydro-2-methyl-1,4-dioxo-2-naphthalenesulfonate. In certain embodiments, vitamins C and K are administered as one or more capsules, each comprising about 500 mg of sodium L-ascorbate and about 5 mg of sodium 1,2,3,4-tetrahydro-2-methyl-1,4-dioxo-2-naphthalenesulfonate.

Depending on the condition, disorder, or disease to be treated and the subject's condition, vitamin C and/or vitamin K in the methods provided herein can be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) route of administration. In some embodiments, vitamin C and/or vitamin K in the methods provided herein is(are) administered by oral, parenteral, or intravenous route of administration. Vitamin C and/or vitamin K in the methods provided herein may be formulated, alone or together, in suitable dosage unit with one or more pharmaceutically acceptable excipient(s), carrier(s), adjuvant(s), or vehicle(s), appropriate for each route of administration.

In one embodiment, vitamin C is administered orally. In another embodiment, vitamin C is administered parenterally. In yet another embodiment, vitamin C is administered intravenously. In still another embodiment, vitamin C is administered topically.

In one embodiment, vitamin K is administered orally. In another embodiment, vitamin K is administered parenterally. In yet another embodiment, vitamin K is administered intravenously. In still another embodiment, vitamin K is administered topically.

In one embodiment, chromium-free vitamin K is administered orally. In another embodiment, chromium-free vitamin K is administered parenterally. In yet another embodiment, chromium-free vitamin K is administered intravenously.

The routes of administration of vitamins C and K can be the same or different. In certain embodiments, both vitamins C and K are administered orally.

In one embodiment, vitamin C is administered concurrently with vitamin K. In another embodiment, vitamin C is administered separately with vitamin K. In yet another embodiment, vitamin C is administered sequentially with vitamin K. In yet another embodiment, vitamin C is administered before vitamin K. In yet another embodiment, vitamin C is administered after vitamin K. Each of the above is encompassed within the term of "in combination with."

In one embodiment, vitamin C and vitamin K are administered together in a single composition comprising vitamin C, or a pharmaceutically acceptable salt, solvate, or hydrate thereof, and vitamin K, or a single enantiomer, a mixture of enantiomers, or a mixture of diastereoisomers thereof, or a pharmaceutically acceptable salt, solvate, or hydrate thereof. In one embodiment, vitamin C and chromium-free vitamin K are administered together in a single composition comprising vitamin C, or a pharmaceutically acceptable salt, solvate, or hydrate thereof, and chromium-free vitamin K, or a single enantiomer, a mixture of enantiomers, or a mixture of diastereoisomers thereof, or a pharmaceutically acceptable salt, solvate, or hydrate thereof.

In certain embodiments, a combination of about 1,000 mg of vitamin C and about 10 mg of vitamin $K_3$ is administered to the subject twice a day (about 2,000 mg of vitamin C and about 20 mg of vitamin $K_3$ per day). In certain embodiments, a combination of about 1,000 mg of vitamin C and about 10 mg of vitamin $K_3$ is administered to the subject twice a day for 13 weeks.

In certain embodiments, a combination of about 1,000 mg of vitamin C and about 6.2 mg of vitamin $K_3$ is administered to the subject twice a day (about 2,000 mg of vitamin C and about 12.4 mg of vitamin $K_3$ per day). In certain embodiments, a combination of about 1,000 mg of vitamin C and about 6.2 mg of vitamin $K_3$ is administered to the subject twice a day for 13 weeks.

In certain embodiments, a daily dose of about 5,000 mg of vitamin C and about 50 mg of vitamin $K_3$ is administered to the subject.

In certain embodiments, vitamin C and vitamin $K_3$ are administered at the levels of about 5 g/m²/day and about 50 mg/m²/day, respectively. In certain embodiments, vitamin C and vitamin $K_3$ are administered at the levels of about 5 g/m²/day and about 50 mg/m²/day, respectively, for 7 days.

In certain embodiments, a combination of vitamin C and vitamin $K_3$ is administered to the subject after mealtime.

In certain embodiments, the subject is a mammal. In certain embodiments, the mammal is a human.

In certain embodiments, the chromium content of the chromium-free vitamin K in a method provided herein is no greater than 10 ppm, no greater than 5 ppm, no greater than 2 ppm, no greater than 1 ppm, or no greater than 100 ppb.

The methods provided herein encompass treating a subject regardless of patient's age, although some conditions, diseases, or disorders are more common in certain age groups. In certain embodiments, the subject is a male. In certain embodiments, the subject is a female. In certain embodiments, the subject is an elderly.

In certain embodiments, the subject is a human with an age of no less than about 20 years, no less than about 30 years, no less than about 40 years, no less than about 45 years, no less than about 50 years, no less than about 55 years, no less than about 60 years, no less than about 65 years, no less than about 70 years, no less than about 75 years, or no less than about 80 years. In certain embodiments, the subject is a human with an age of above about 60, above about 65, above about 70, or above about 75. In certain embodiments, the subject is a human with an age ranging from about 20 to about 30 years, from about 30 to about 40 years, from about 40 to about 50 years, from about 50 to about 60 years, from about 60 to about 70 years, or from about 70 to about 80 years. In certain embodiments, the subject is a human with an age ranging from about 1 to about 110 years, from about 1 to about 100 years, from about 1 to about 90 years, from about 1 to about 80 years, from about 1 to about 70 years, from about 1 to about 60 years, or from about 1 to about 50 years.

In certain embodiments, the subject is a human with an age of no greater than about 20 years, no greater than about 15, no greater than about 10, no greater than about 5, or no greater than about 2.

In certain embodiments, the subject to be treated with one of the methods provided herein has not been treated with any of the methods provided herein. In certain embodiments, the subject to be treated with one of the methods provided herein has been treated with one of the methods provided herein.

The combination regimen can be administered repetitively if necessary, for example, until the patient experiences stable disease or regression, or until the patient experiences disease progression or unacceptable toxicity. Stable disease or lack thereof is determined by methods known in the art such as evaluation of patient symptoms, physical examination, or diagnostic testing.

In certain embodiments, the combination regimen is for acute use or short term use, e.g., during the period of the onset of the condition, disorder, or disease described herein. In certain embodiments, the combination regimen is for chronic use or long term use, e.g., before, after, and during the period of the onset of the condition, disorder, or disease described herein.

In certain embodiments, the combination regimen is administered to the subject over an extended period of time, ranging from about 1 day to about 50 years, from about 10 days to about 25 years, from about 1 month to about 10 years, or from about 6 months to about 5 years. In certain embodiments, the combination regimen is administered to the subject for about 12 weeks. In certain embodiments, the combination regimen is administered to the subject for about 6 months. In certain embodiments, the combination regimen is administered to the subject for about 1 year. In certain embodiments, the combination regimen is administered to the subject for about 2 years.

In certain embodiments, the combination regimen is cyclically administered to the subject. Cycling therapy involves the administration of the combination regimen provided herein for a period of time, followed by a rest for a period of time, and repeating this sequential administration.

As used herein, the term "combination regimen" includes the use of more than one therapies (e.g., one or more prophylactic and/or therapeutic agent(s)). However, the use of the term "combination regimen" does not restrict the order in which therapies (e.g., prophylactic and/or therapeutic agents) are administered to the subject. A first therapy (e.g., a prophylactic or therapeutic agent such as vitamin C provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as vitamin K provided herein) to the subject.

The methods provided herein may further comprise administering an additional therapeutic agent useful in the treatment and/or prevention of a condition, disorder, or disease described herein.

In triple therapy (e.g., combinations of vitamin C and chromium-free vitamin K (e.g., APATONE®) and another agent), effective dosages of therapeutic agents can be administered together, alternatively, or sequentially. The dosages given will depend on absorption, inactivation, and excretion rates of the therapeutic agents as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

Examples of the additional therapeutic agent include, but are not limited to, anti-atherosclerotic agents, such as ACAT inhibitors; antibiotics, such as anthracyclines, bleomycins, mitomycin, dactinomycin, and plicamycin; anticoagulants, such as acenocoumarol, argatroban, bivalirudin, lepirudin, fondaparinux, heparin, phenindione, warfarin, and ximelagatran; antifungal agents, such as amorolfine, amphotericin B, anidulafungin, bifonazole, butenafine, butoconazole, caspofungin, ciclopirox, clotrimazole, econazole, fenticonazole, filipin, fluconazole, isoconazole, itraconazole, ketoconazole, micafungin, miconazole, naftifine, natamycin, nystatin, oxyconazole, ravuconazole, posaconazole, rimocidin, sertaconazole, sulconazole, terbinafine, terconazole, tioconazole, and voriconazole; antiinflammatories, e.g., non-steroidal anti-inflammatory agents, such as aceclofenac, acemetacin, amoxiprin, aspirin, azapropazone, benorilate, bromfenac, carprofen, celecoxib, choline magnesium salicylate, diclofenac, diflunisal, etodolac, etoricoxib, faislamine, fenbufen, fenoprofen, flurbiprofen, ibuprofen, indometacin, indomethacin, ketoprofen, ketorolac, lornoxicam, loxoprofen, lumiracoxib, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinpyrazone, suprofen, tenoxicam, tiaprofenic acid, and tolmetin; anti-platelet agents, such as GPIIb/IIIa blockers (e.g., abciximab, eptifibatide, and tirofiban), P2Y(AC) antagonists (e.g., clopidogrel, ticlopidine and CS-747), cilostazol, dipyridamole, and aspirin; antiproliferatives, such as methotrexate, FK506 (tacrolimus), and mycophenolate mofetil; anti-TNF antibodies or soluble TNF receptor, such as etanercept, rapamycin, and leflunimide; aP2 inhibitors; beta-adrenergic agents, such as carvedilol and metoprolol; bile acid sequestrants, such as questran; calcium channel blockers, such as amlodipine besylate; chemotherapeutic agents; bisphosphonates, such as alendronate, risendronate, ibandtonate, pamidronate, and etidronate; cyclooxygenase-2 (COX-2) inhibitors, such as celecoxib and rofecoxib; cyclosporins; cytotoxic drugs, such as azathioprine and cyclophosphamide; diuretics, such as chlorothiazide, hydrochlorothiazide, flumethiazide, hydroflumethiazide, bendroflumethiazide, methylchlorothiazide, trichloromethiazide, polythiazide, benzothiazide, ethacrynic acid, ticrynafen, chlorthalidone, furosenide, muzolimine, bumetanide, triamterene, amiloride, and spironolactone; endothelin converting enzyme (ECE) inhibitors, such as phosphoramidon; enzymes, such as L-asparaginase; Factor VIIa inhibitors and Factor Xa inhibitors; farnesyl-protein transferase inhibitors; fibrates; growth factor inhibitors, such as modulators of PDGF activity; growth hormone secretagogues; HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, atavastatin, or visastatin); neutral endopeptidase (NEP) inhibitors; hormonal agents, such as glucocorticoids (e.g., hydrocortisone and cortisone), estrogens/antiestrogens, androgens/antiandrogens, progestins, luteinizing hormone-releasing hormone antagonists, and octreotide acetate; immunosuppressants; mineralocorticoid receptor antagonists, such as spironolactone and eplerenone; microtubule-disruptor agents, such as ecteinascidins; microtubule-stabilizing agents, such as pacitaxel, docetaxel, and epothilones A-F; MTP inhibitors; niacin; phosphodiesterase inhibitors, such as PDE III inhibitors (e.g., cilostazol) and PDE V inhibitors (e.g., sildenafil, tadalafil, and vardenafil); plant-derived products, such as vinca alkaloids, epipodophyllotoxins, and taxanes; platelet activating factor (PAF) antagonists; platinum coordination complexes, such as cisplatin, satraplatin, and carboplatin; potassium channel openers; prenyl-protein transferase inhibitors; protein tyrosine kinase inhibitors; protein serine/threonine inhibitors; renin inhibitors; squalene synthetase inhibitors; steroids, such as aldosterone, beclometasone, betamethasone, deoxycorticosterone acetate, fludrocortisone, hydrocortisone (cortisol), prednisolone, prednisone, methylprednisolone, dexamethasone, and triamcinolone; TNF-alpha inhibitors, such as tenidap; thrombin inhibitors, such as hirudin; thrombolytic agents, such as anistreplase, reteplase, tenecteplase, tissue plasminogen activator (tPA), recombinant tPA, streptokinase, urokinase, prourokinase, and anisoylated plasminogen streptokinase activator complex (APSAC); thromboxane receptor antagonists, such as ifetroban; topoisomerase inhibitors; vasopeptidase inhibitors (dual NEP-ACE inhibitors), such as omapatrilat and gemopatrilat; and other miscellaneous agents, such as, hydroxyurea, procarbazine, mitotane, hexamethylmelamine, and gold compounds.

In another embodiment, provided herein is a method of reducing NFκB production in a cell, comprising contacting the cell with an effective amount of vitamin C, or a pharmaceutically acceptable salt, solvate, or hydrate thereof, in combination with chromium-free vitamin K, or a single enantiomer, a mixture of enantiomers, or a mixture of diastereomers thereof, or a pharmaceutically acceptable salt, solvate, or hydrate thereof.

In certain embodiments, the cell is a mammalian cell. In certain embodiments, the mammal is a human cell.

In certain embodiments, the cell is treated by contacting the cell with vitamin C, prior to contacting the cell with vitamin K. In certain embodiments, the cell is treated by contacting the cell with vitamin C, concurrently with vitamin K. In certain embodiments, the cell is treated by contacting the cell with vitamin C, after contacting the cell with vitamin K.

In certain embodiments, provided herein is a method for inhibiting cystogenesis in an organ, comprising contacting the organ with an effective amount of vitamin C, or a pharmaceutically acceptable salt, solvate, or hydrate thereof and vitamin K, or a single enantiomer, a mixture of enantiomers, or a mixture of diastereomers thereof, or a pharmaceutically acceptable salt, solvate, or hydrate thereof.

In certain embodiments, the organ is a kidney. In certain embodiments, the organ is a liver.

The combination regimes provided herein can also be provided as an article of manufacture using packaging materials well known to those of skill in the art. See, e.g., U.S. Pat. Nos. 5,323,907; 5,052,558; and 5,033,252; incorporated herein by reference. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

Provided herein also are kits which, when used by the medical practitioner, can simplify the administration of appropriate amounts of active ingredients to a subject. In certain embodiments, the kit provided herein includes containers and dosage forms of the compounds in the combination regimens provided herein.

In certain embodiments, the kit includes a container comprising dosage forms of the compounds in the combination regimens provided herein, in one or more containers.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The disclosure will be further understood by the following non-limiting examples.

EXAMPLES

Example 1

Effect of Prosthetic Particulate Debris on Human Synovial Fibroblasts

Two different sources of metallic particulate powders, CoCrMo-I and CoCrMo-II, each having a size smaller than 10 µm, were used in this example. These powders were ASTM F75 grade material, which is commonly used in joint replacement prostheses. Energy dispersive spectroscopy (ESD) was used to determine the bulk metallic composition, and X-ray photoelectron spectroscopy (XPS) was used to determine the surface metallic composition of the particles. The results are summarized in Table 1. While multiple EDS area scans identified the bulk metallic compositions of the powders to resemble the ASTM F75 CoCrMo standard, multiple XPS survey scans demonstrated that the surface metallic compositions were different.

TABLE 1

|  | CoCrMo-I | | CoCrMo-II | | F75 CoCrMo[c] |
| --- | --- | --- | --- | --- | --- |
|  | EDS[a] | XPS[b] | EDS[a] | XPS[b] | ASTM Standard |
| Co | 62% | 30% | 62% | 69% | 57.4-65% |
| Cr | 34% | 30% | 32% | 28% | 27-30% |
| Mo | 3% | 5% | 4% | 3% | 5-7% |
| Si | 1% | 27% | 2% | 0% | ≤1% |
| Mn | 0% | 8% | 0% | 0% | ≤1% |

[a]Experimental uncertainty is 2%.
[b]Experimental uncertainty is <5%.
[c]Standards as published by the American Society for testing Materials.

Using an experimental protocol approved by the Institutional Review Board Committee on Human Research, a cell culture study was performed, exposing human synovial fibroblasts to CoCrMo-I and CoCrMo-II, in order to assess any effects the different materials might have on cellular viability. The cells were harvested from tissue of the knee joint of four consented human volunteer donors undergoing a total knee replacement. The harvested tissue was processed as described (Mostardi et al., *J. Biomed. Mater. Res.* 1999, 47, 60; and Mostardi et al., *J. Biomed. Mater. Res.* 2002, 59, 605), passaging each donor cell line once prior to being transferred to multiple 25 $cm^2$ culture flasks. The fibroblasts in each culture flask were then allowed to grow to confluency (a single-cell layer that occupies a give area; $1\times10^6$ cells per flask) before experimental powder exposure.

Prior to their exposure to the confluent fibroblast cultures, the CoCrMo-I and CoCrMo-II powders were sterilized and verified to be endotoxin free by a limulus amebocyte lysate assay. Two mass dosage (0.004 g and 0.04 g) of each metal powder to induce a minimal and a maximal cytotoxic effect, respectively, were individually added to separate culture flasks containing each donor cell line. In addition, culture flasks from each donor cell line, to which no metal powder was added, were used as confluent controls.

Five days after the exposure dosages of each metal powder to the culture flasks, cell viability counts were made from each culture flask using hemocytometer and trypan blue exclusion (counting the number of viable cells which have not taken up the dye color). The resulting viability counts were first normalized by counts from their respective, non-challenged, control flasks and then were averaged over all four donors to create a composite mean and standard deviation for each metal powder sample.

The type of metal powder used exhibited a significant effect on the cellular viability (p<0.0001). Fibroblast exposure to the 0.004 g dosage of CoCrMo-I powder resulted in a nominal 11% reduction in viability, where the same exposure dosage of CoCrMo-II powder resulted in an 86% reduction in viability. Differences in effects on fibroblast viability were even more apparent at the higher 0.04 dosage, with the CoCrMo-I powder resulting in a moderate 30% reduction in viability and the CoCrMo-II powder resulting in a 97% reduction in viability. See, Kovacik et al., *Colloids and Surface B: Biointerfaces* 2008, 65, 269-275.

Example 2

Effect of Vitamins C and $K_3$ on Human Synovial Fibroblasts Exposed to Metal Particles A metal exposure dosage of 0.01 g (CoCrMo-I as described in Example 1) was used for all cell exposure studies in this example. APATONE® was prepared in a 100:1 ratio (75.0 µM of vitamin C (sodium L-ascorbate) and 0.75 µM of chromium-free vitamin $K_3$ (vitamin $K_3$ sodium bisulfite)).

Human synovial fibroblasts were harvested and processed as described in Example 1. The donor cell line was passaged once prior to the seeding of about $1\times10^6$ cells into each of ten 75 $cm^2$ culture flasks. The flasks were then incubated over a 5-day period to render about $5\times10^6$ cells. Five of the flasks were incubated for 24 hrs and consisted of: a) control (cell only), b) cell treated with APATONE® only, c) cells exposed to metal only, d) cells treated with APATONE® for 24 hrs prior to metal exposure, and e) cells exposed to metals 24 hrs prior to APATONE® treatment. The remaining five flasks, prepared in the same manner, were incubated for a 48 hr interval.

Flasks at each of the respective time interval (24 hr or 48 hr) were assessed for cell viability (hemocytometer with trypan blue exclusion) and NFκB levels (EZ-Detect NFκB p65 Transcription Assay, Thermo Fisher Scientific, Rockford, Ill.). The results are summarized in Table 2.

TABLE 2

|  | Cell Viability | | NFκB Level | |
| --- | --- | --- | --- | --- |
|  | 24 hrs | 48 hrs | 24 hrs | 48 hrs |
| APATONE ® | 1.04 | 1.67 | 1.20 | 0.79 |
| F75 CoCrMo | 1.12 | 1.10 | 1.49 | 0.94 |
| APATONE ® then F75 CoCrMo | 1.06 | 1.17 | 0.49 | 0.58 |
| F75 CoCrMo then APATONE ® | 1.06 | 1.08 | 1.09 | 0.31 |

Since fibroblast viability was 104% of the control at 24 hrs and 167% of the control at 48 hrs, APATONE® was not toxic to the fibroblasts at this dose. Fibroblast viability remained relatively constant following exposure to the metal with 112% and 110% viability compared to control fibroblasts after 24 and 48 hrs, respectively. Fibroblast viability was 106% and 117% when the fibroblasts were exposed to APATONE® 24 hrs before the metal. The increase in cell viability at 48 hrs was probably due to APATONE® induced cell division of the fibroblasts. As was the case for metal treatment alone, fibroblast viability remained constant 106% and 108% when APATONE® treatment followed metal treatment.

When synovial fibroblasts were treated with APATONE®, NFκB levels rose to 120% of control by 24 hrs and then decreased to 79% of control by 48 hrs. Exposure of fibroblasts to the metal led to an increase of NFκB levels to 149% of control by 24 hrs. NFκB levels returned to 95% of control by 48 hrs. Pretreatement of fibroblasts with APATONE® before exposure to metal resulted in NFκB levels to 49% of control by 24 hrs. NFκB levels rose to 58% of control by 48 hrs. Administration of APATONE® following metal exposure produced a slight increase in NFκB levels to 109% of control by 24 hrs. NFκB levels then decreased to 31% of control by 48 hrs.

Example 3

Capsule Formulation (1,000 mg Vitamin C and 10 mg Chromium-Free Vitamin $K_3$)

For 100 capsules, sodium ascorbate powder (100 g) and water soluble chromium-free vitamin $K_3$ (menadione sodium bisulfite) powder (1.0 g) are mixed together. The mixture is then placed into capsules in the amount of 1,010 mg each, without any supplementary ingredients or any pharmaceutically acceptable excipients.

Example 4

Capsule Formulation (500 mg Vitamin C and 5 mg Chromium-Free Vitamin $K_3$)

For 100 capsules, sodium ascorbate powder (50 g) and water soluble chromium-free vitamin $K_3$ (menadione sodium bisulfite) powder (0.5 g) are mixed together. The mixture is then placed into capsules in the amount of 505 mg each, without any supplementary ingredients or any pharmaceutically acceptable excipients.

Example 5

Capsule Formulation (500 mg Vitamin C and 3.1 mg Chromium-Free Vitamin $K_3$)

For 100 capsules, sodium ascorbate powder (50 g) and water soluble chromium-free vitamin $K_3$ (menadione sodium bisulfite) powder (0.31 g) are mixed together. The mixture is then placed into capsules in the amount of 503.1 mg each, without any supplementary ingredients or any pharmaceutically acceptable excipients.

Example 6

Capsule Formulation (200 mg Vitamin C and 2 mg Chromium-Free Vitamin $K_3$)

For 100 capsules, sodium ascorbate powder (20 g) and water soluble chromium-free vitamin $K_3$ (menadione sodium bisulfite) powder (0.2 g) are mixed together. The mixture is then placed into capsules in the amount of 202 mg each, without any supplementary ingredients or any pharmaceutically acceptable excipients.

Example 7

Tablet Formulation (500 mg Vitamin C and 5 mg Chromium-Free Vitamin $K_3$)

For 100 tablets, sodium ascorbate powder (50 g) and water soluble chromium-free vitamin $K_3$ (menadione sodium bisulfite) powder (0.5 g) are mixed together with microcrystalline cellulose.

Example 8

Parenteral Dosage Formulation (5 g Vitamin C and 50 mg Chromium-Free Vitamin $K_3$)

A vitamin C solution is prepared by dissolving sodium ascorbate (5 g) and NaCl (1.2 g) in sterile water (300 mL) for injection. A vitamin $K_3$ solution is prepared by dissolving chromium-free menadione sodium bisulfite (50 mg) in sterile water (5 mL) for injection.

These solutions must be oxygen-free (e.g., perfused with gaseous nitrogen); sterilized by filtration (millipore filters of pore diameter approximately 0.22 nm); and introduced into sterile and devoid of oxygen pockets for the vitamin C solution or glass vials for vitamin $K_3$ solution. Each series of prepared pockets or vials must be examined for apyrogenicity and sterility by methods known in the art. Since both vitamins are oxygen, light, and temperature sensitive, the solutions should be stored in anoxic conditions at approximately 4° C. in darkness.

Alternately, the parenteral solution is prepared by mixing sodium ascorbate (5 g) and chromium-free menadione sodium bisulfite (50 mg) in 300 mL of sterile non-pyrogenic normal saline in an IV bag immediately prior to use.

Example 9

Capsule Formulation (1,000 mg Vitamin C and 10 mg Chromium-Free Vitamin $K_3$)

For 100 capsules, sodium ascorbate powder (100 g) and water soluble chromium-free vitamin $K_3$ (menadione sodium bisulfite, with ≤2 ppm Cr) powder (1.0 g) are mixed together. The mixture is then placed into capsules in the amount of 1,010 mg each, without any supplementary ingredients or any pharmaceutically acceptable excipients.

Example 10

Capsule Formulation (500 mg Vitamin C and 5 mg Chromium-Free Vitamin $K_3$)

For 100 capsules, sodium ascorbate powder (50 g) and water soluble chromium-free vitamin $K_3$ (menadione sodium bisulfite, with ≤2 ppm Cr) powder (0.5 g) are mixed together. The mixture is then placed into capsules in the amount of 505 mg each, without any supplementary ingredients or any pharmaceutically acceptable excipients.

Example 11

Capsule Formulation (500 mg Vitamin C and 3.1 mg Chromium-Free Vitamin $K_3$)

For 100 capsules, sodium ascorbate powder (50 g) and water soluble chromium-free vitamin $K_3$ (menadione sodium bisulfite, with ≤2 ppm Cr) powder (0.31 g) are mixed together. The mixture is then placed into capsules in the amount of 503.1 mg each, without any supplementary ingredients or any pharmaceutically acceptable excipients.

Example 12

Capsule Formulation (200 mg Vitamin C and 2 mg Chromium-Free Vitamin $K_3$)

For 100 capsules, sodium ascorbate powder (20 g) and water soluble chromium-free vitamin $K_3$ (menadione sodium bisulfite, with ≤2 ppm Cr) powder (0.2 g) are mixed together. The mixture is then placed into capsules in the amount of 202 mg each, without any supplementary ingredients or any pharmaceutically acceptable excipients.

Example 13

Tablet Formulation (500 mg Vitamin C and 5 mg Chromium-Free Vitamin $K_3$)

For 100 tablets, sodium ascorbate powder (50 g) and water soluble chromium-free vitamin $K_3$ (menadione sodium bisulfite, with ≤2 ppm Cr) powder (0.5 g) are mixed together with microcrystalline cellulose.

Example 14

Parenteral Dosage Formulation (5 g Vitamin C and 50 mg Chromium-Free Vitamin $K_3$)

A vitamin C solution is prepared by dissolving sodium ascorbate (5 g) and NaCl (1.2 g) in sterile water (300 mL) for injection. A vitamin $K_3$ solution is prepared by dissolving chromium-free menadione sodium bisulfite (50 mg, ≤2 ppm Cr) in sterile water (5 mL) for injection.

These solutions must be oxygen-free (e.g., perfused with gaseous nitrogen); sterilized by filtration (millipore filters of pore diameter approximately 0.22 nm); and introduced into sterile and devoid of oxygen pockets for the vitamin C solution or glass vials for vitamin $K_3$ solution. Each series of prepared pockets or vials must be examined for apyrogenicity and sterility by methods known in the art. Since both vitamins are oxygen, light, and temperature sensitive, the solutions should be stored in anoxic conditions at approximately 4° C. in darkness.

Alternately, the parenteral solution is prepared by mixing sodium ascorbate (5 g) and chromium-free menadione sodium bisulfite (50 mg, ≤2 ppm Cr) in 300 mL of sterile non-pyrogenic normal saline in an IV bag immediately prior to use.

Example 15

Effect of Vitamins C and $K_3$ on Tumor Growth

Female immuno-compromised mice (NCI: Hsd:Athymic Nude-n) that were 4-6 weeks old were injected with 10 million K562 human leukemia cells suspended in 0.1 mL of a sterile serum free culture medium/Matrigel mixture (1:1) s.c. (subcutaneously) into the right flank. Tumors were allowed to form for forty-eight hours. The mice were divided into three groups with 10 mice per group. The first group received a single i.p. (intraperitoneal) injection of Vitamin C (sodium ascorbate, Sigma Aldrich) and Vitamin $K_3$ (chromium containing Vitamin $K_3$, Sigma Aldrich) ($CK_3$) at 1 g/kg and 10 mg/kg, respectively. The second group received a single i.p. (intraperitoneal) injection of Vitamin C (sodium ascorbate, Sigma Aldrich) and Vitamin $K_3$ (chromium-free Vitamin $K_3$, Lonza) (chrome-free $CK_3$) at 1 g/kg and 10 mg/kg, respectively. The third group received a single i.p. (intraperitoneal) injection of normal saline as an experimental control. All solutions were filtered through a 0.22 micron filter prior to injection. The tumors were then subsequently measured. Mice were then euthanized by $CO_2$ inhalation and cervical dislocation. Tumors were excised, weighed, and divided for formalin fixation, or frozen in liquid nitrogen for histology and immunohistochemistry.

Figure 1B:
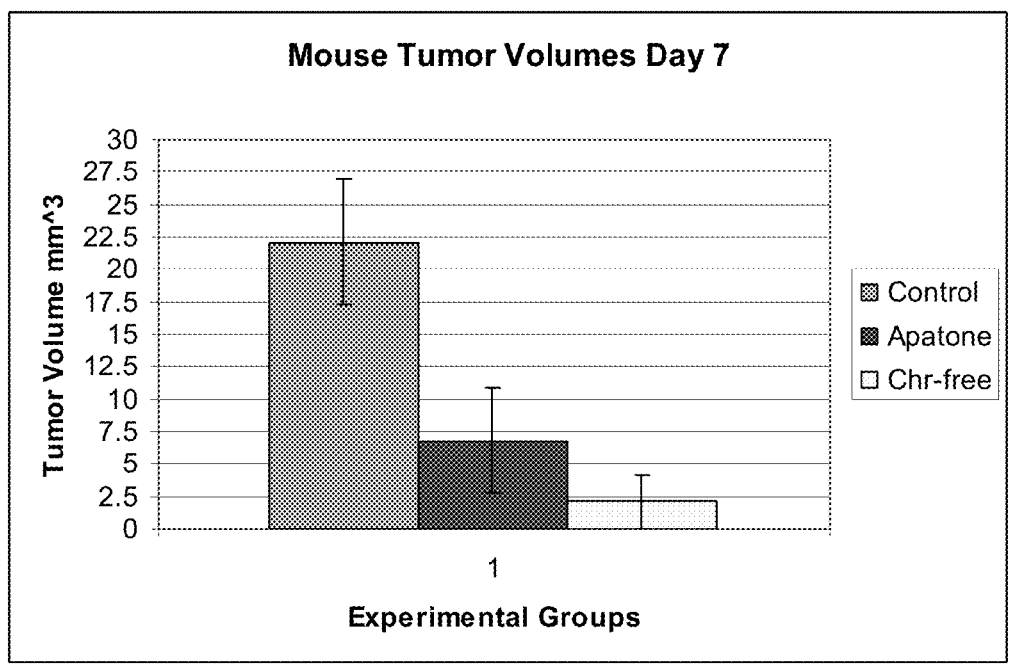

The tumor take rate was 97%. Tumors volume calculated at day 5 ranged between 16.6 and 29.4 mm$^3$ in control animals, between 5.1 and 12.5 mm$^3$ for $CK_3$ treated animals, and between 8.3 and 12.6 mm$^3$ in chromium-free $CK_3$ treated animals. Tumor volume calculated at day 7 ranged between 17.8 and 22.9 mm$^3$ in control animals, between 2.4 and 13.6 mm$^3$ for $CK_3$ treated animals, and between 1.8 and 7.2 mm$^3$ in chromium-free $CK_3$ treated animals. Results are further summarized in Table 3 and FIGS. 1A and 1B.

TABLE 3

Percentage decrease in tumor size in control and treated tumors in vivo, n = 8

|  | Day 5 | Day 7 |
| --- | --- | --- |
| Control | — | — |
| $CK_3$ | −51.7% | −69% |
| Chrome-free $CK_3$ | −49.7% | −74% |

These results show that treatments with chromium-containing $CK_3$ and treatments with chromium-free $CK_3$ significantly decreased K562 leukemia tumor volumes following single i.p. injections. This is a first in vivo data demonstrating that chromium-free $CK_3$ is as effective as chromium-containing $CK_3$. The data also demonstrates the effectiveness of a chromium-free $CK_3$ product to safeguard against the effects of long-term chromium use.

Example 16

Comparison of Cystic Cholangiocytes with Normal Cholangiocytes

Animals and Cell Culture: Animals (rats and mice) were maintained on a standard diet after Mayo Institutional Animal Care and Use Committee approval. They were anesthetized with pentobarbital (50 mg/kg). Blood was collected from PCK rats by cardiac puncture. Liver and kidneys were fixed and embedded in paraffin for histology. For in vitro study, cholangiocytes were isolated from normal and PCK rats and cultured according to the procedures as described in Banales et al., Hepatology 2009, 49, 160-74. Normal and diseased human liver tissue were obtained from Mayo Clinical Core and National Disease Research Interchange.

Flow Cytometry: Normal (n=5) and PCK cholangiocytes (n=6) were fixed in ethanol and suspended in 50 µg/mL propidium iodide containing 0.1 mg/mL RNase. Cell cycle analysis was performed at Mayo Advanced Genomics Technology Center.

Immunofluorescence Confocal Microscopy: Microscopy was performed with Zeiss LSM-510 microscope (Carl Zeiss, Thornwood, N.Y.) using liver tissue of control and PCK rats; control and Pkd2$^{WS25/-}$ mice; healthy human beings and patients with ADPKD, ARPKD and CHF. Liver sections were stained with primary antibodies against PCNA and Cdc25A (Santa Cruz Biotechnology, Santa Cruz, Calif.; 1:100). Respective secondary antibodies (Invitrogen, Carlsbad, Calif.; 1:200) were applied. Apoptosis was assessed by Terminal deoxynucleotidyl transferase dUTP nick-end labeling (TUNEL) assay (Chemicon, Billerica, Mass.). Mitotic and apoptotic indices were calculated, correspondingly, as a percent of PCNA- or TUNEL-positive nuclei out of 500 cells in randomly selected fields of liver and kidney sections.

Western Blot: For western blotting: (i) cholangiocytes isolated from control and PCK rats; control and Pkd2$^{WS25/-}$ mice; healthy human beings and ADPKD patients; and (ii) cultured PCK cholangiocytes were used. The cholangiocytes were resuspended in RIPA Buffer (Santa Cruz). Protein (30 µg) was run in 4-15% Tris-HCl sodium dodecyl sulfate-polyacrylamide gel, transferred to a membrane (BioRad, Hercules, Calif.), and incubated overnight at 4° C. with antibodies against PCN (1:500). Respective secondary antibodies (Invitrogen; 1:5000) were applied for 60 min. Bands were visualized with the ECL Plus Western Blotting Detection Kit (BD Biosciences). Actin staining was normalized for protein loading (Abcam; 1:1000).

Figure 2A:
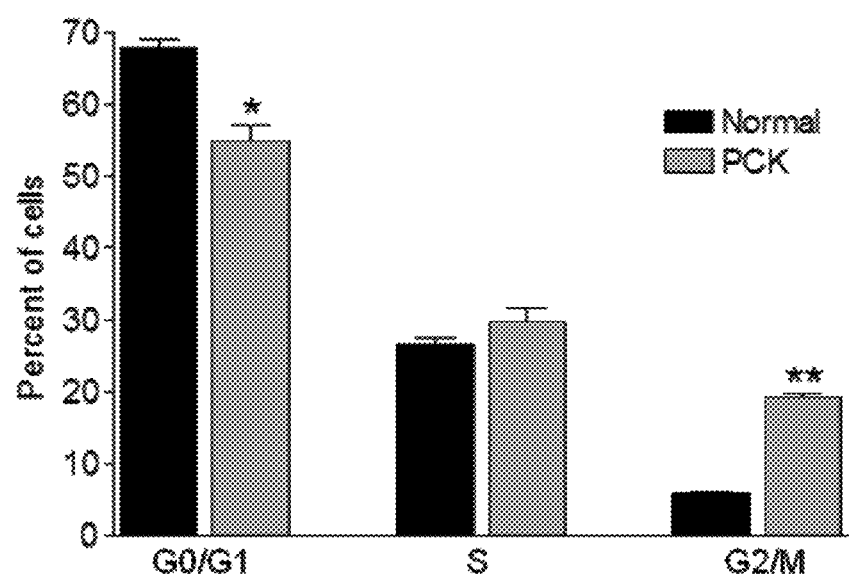
FIGS. 2A to 2C show cell cycle phase distribution in cystic and normal cholangiocytes. *: $p<0.01$ and **: $p<0.0001$.
Figure 2B:
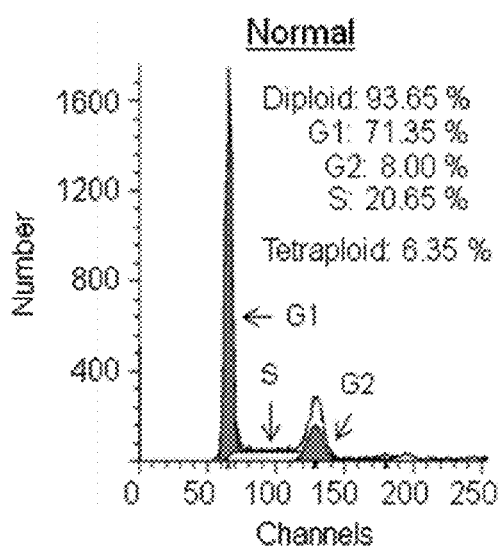
Figure 2C:
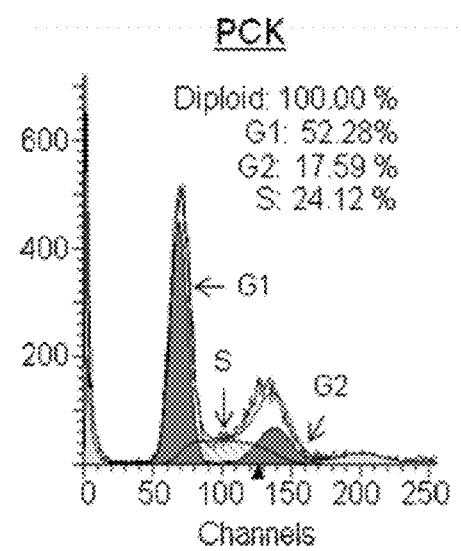

In cystic cholangiocytes isolated from an animal model of PLD/PKD, PCK rats, the percent of cells in G0/G1 phase was reduced, the percent of cells in S phase was not altered, and the percent of cells in G2/M phase was increased, in comparison with normal cholangiocytes (FIGS. 2A and 2B).

As shown in FIG. 2A, the majority of cells in normal rat cholangiocytes (n=5) were present in G0/G1 phase and the percent of cholangiocytes in G2/M phase was relatively low. In PCK cholangiocytes (n=6), the percent of cells in G0/G1 phase was decreased, while the percent of cells in G2/M phase was increased compared to normal. As shown in FIG. 2B, the cultured normal and PCK cholangiocytes were both diploid.

The rate of proliferation in humans and rodents was also examined by determining proliferating cell nuclear antigen (PCNA) expression. PCNA was overexpressed in cystic cholangiocytes. In normal human, rat, and mouse cholangiocytes (n=3 of each), PCNA expression (green) was nearly absent. Cystic cholangiocytes in human patients with ARPKD (n=3), ADPKD (n=5), CHF (n=3); in PCK rats (n=6) and Pkd2$^{WS25/-}$ mice (n=5) showed a rigorous PCNA staining. In other words, cystic cholangiocytes in patients with PLD/PKD, in PCK rats, and Pkd2$^{WS25/-}$ mice were PCNA immunoreactive, whereas normal cholangiocytes were not PCNA immunoreactive.

Figure 3:
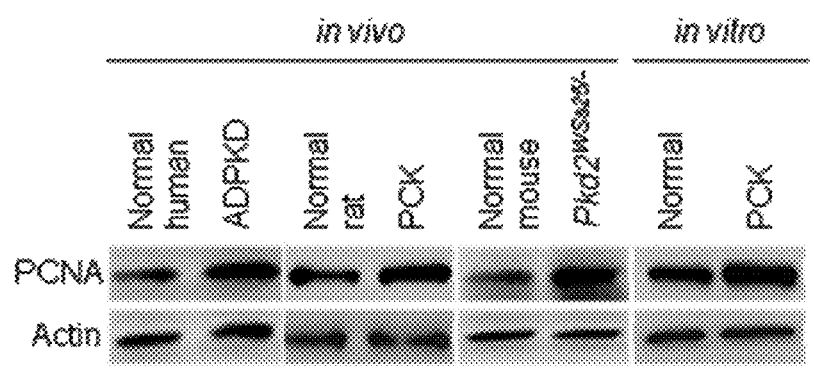
FIG. 3 shows PCNA expression levels in cystic and normal cholangiocytes.

Western blots (n=3 for each) further confirmed that PCNA levels were increased in vivo in cholangiocytes isolated from ADPKD patients, PCK rats, and Pkd2$^{WS25/-}$ mice, and in vitro in PCK-derived cholangiocytes compared to respective normal controls (FIG. 3).

Figure 4:
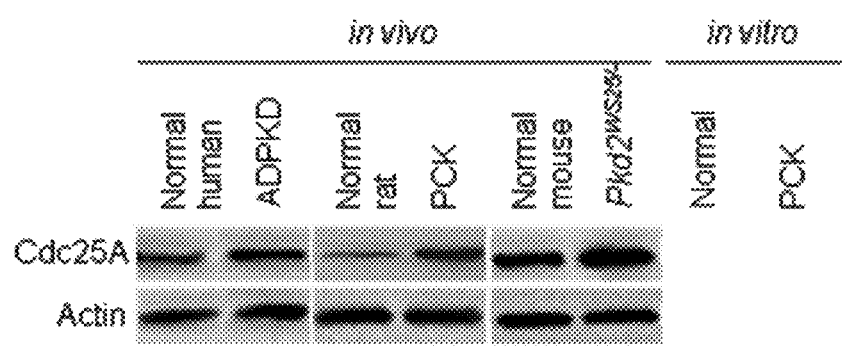
FIG. 4 shows Cdc25A expression levels in cystic and normal cholangiocytes.
Figures 5A, 5B, 5C, 5D:
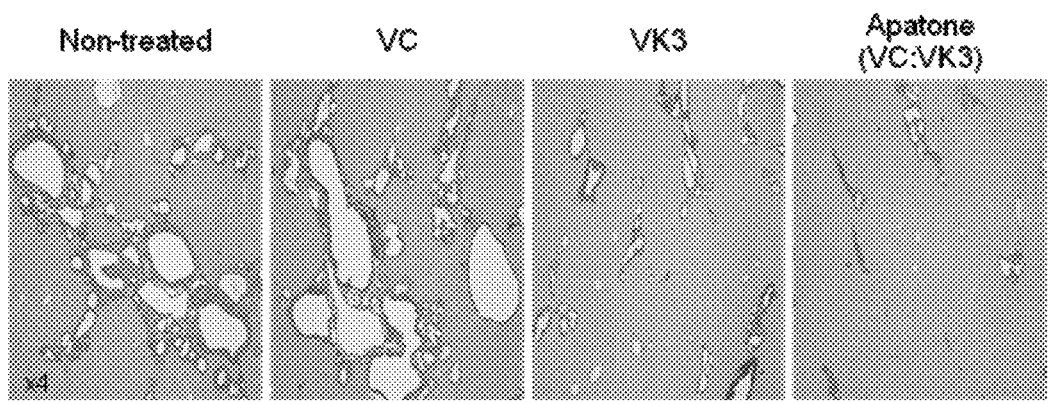
FIGS. 5A to 5D show images of picrosirius red-stained liver sections of PCK rats untreated or treated with vitamin C, vitamin $K_3$, or APATONE®.
Figure 5E:
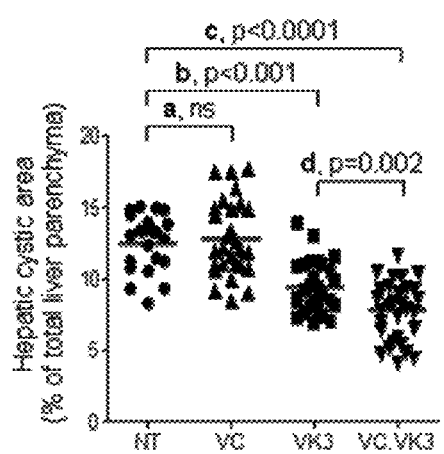
FIGS. 5E and 5F show effects of vitamin C, vitamin $K_3$, and APATONE® on hepatic cystogenesis in PCK rats. NT: non-treated; VC: vitamin C-treated; VK3: vitamin $K_3$-treated; and VC:CK3: APATONE®-treated.
Figure 5F:
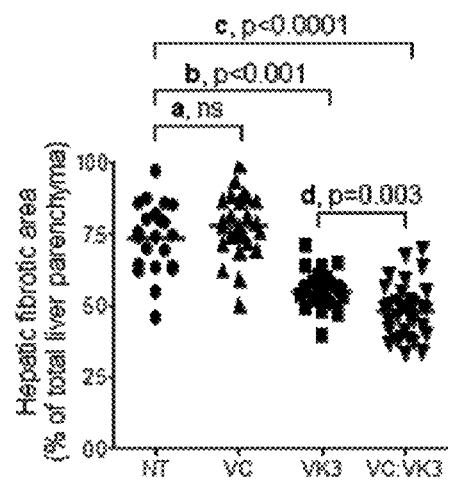
Figures 7A, 7B, 7C, 7D:
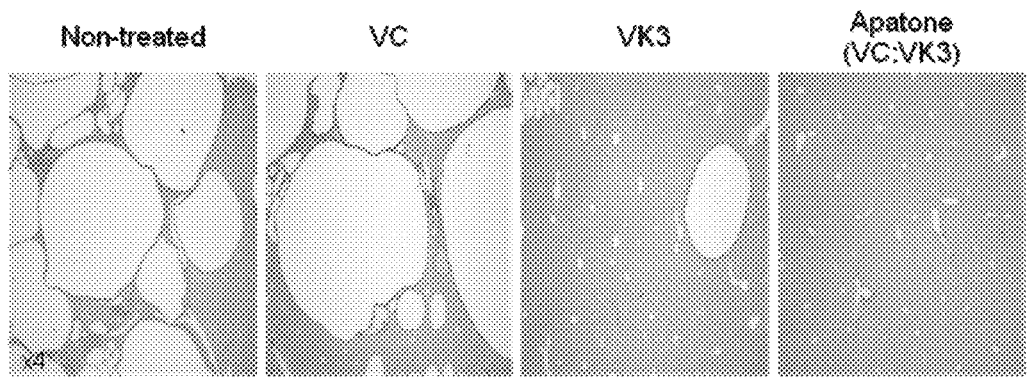
FIGS. 7A to 7D show images of picrosirius red-stained liver sections of Pkd2$^{WS25/-}$ mice untreated or treated with vitamin C, vitamin $K_3$, or APATONE®.
Figure 7E:
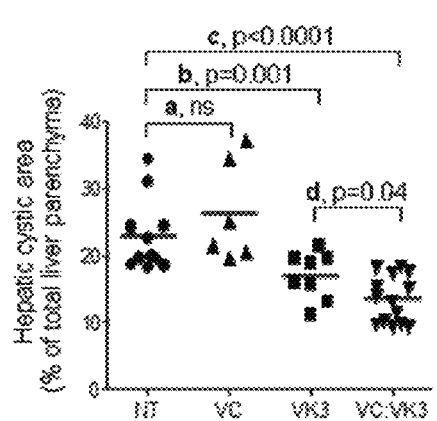
FIGS. 7E and 7F show effects of vitamin C, vitamin $K_3$, and APATONE® on hepatic cystogenesis in Pkd2$^{WS25/-}$ mice. NT: non-treated; VC: vitamin C-treated; VK3: vitamin $K_3$-treated; and VC:CK3: APATONE®-treated.
Figure 7F:
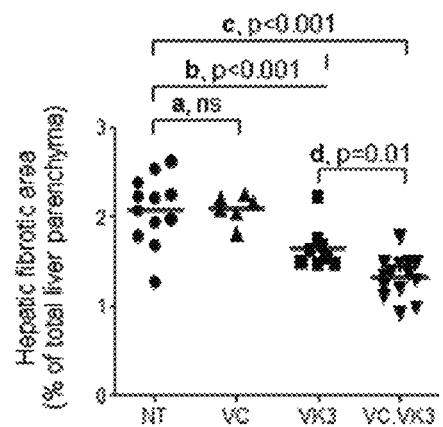
Figures 8A, 8B, 8C, 8D:
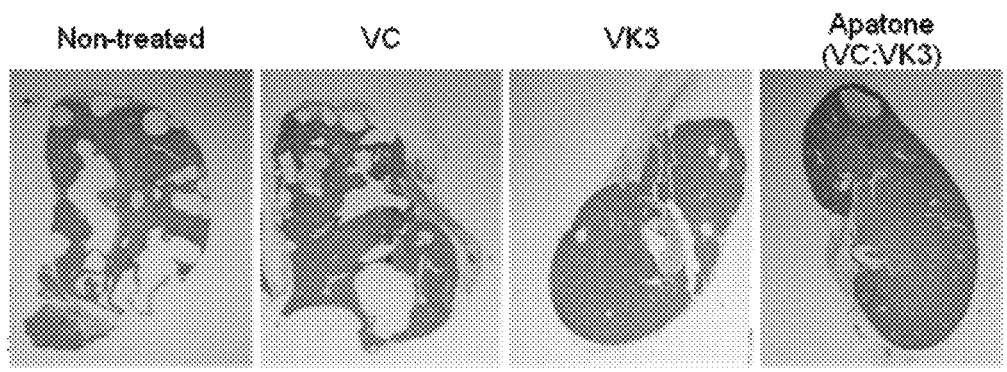
FIGS. 8A to 8D show images of picrosirius red-stained kidney sections of Pkd2$^{WS25/-}$ mice untreated or treated with vitamin C, vitamin $K_3$, or APATONE®.
Figure 8E:
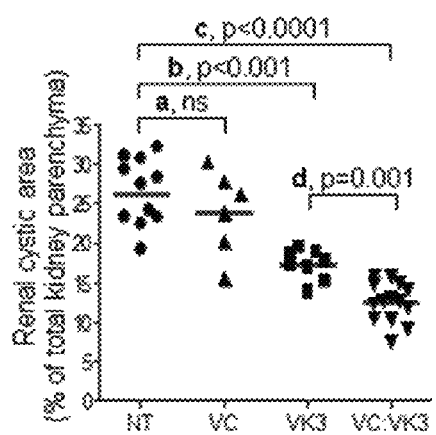
FIGS. 8E and 8F show effects of vitamin C, vitamin $K_3$, and APATONE® on renal cystogenesis in Pkd2$^{WS25/-}$ mice. NT: non-treated; VC: vitamin C-treated; VK3: vitamin $K_3$-treated; and VC:CK3: APATONE®-treated.
Figure 8F:
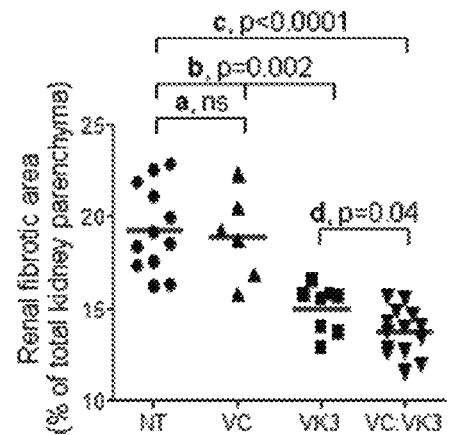

Cell division cycle 25 homolog A (Cdc25A) was found to be over-expressed in cystic cholangiocytes. Relatively low expression of Cdc25A was found in normal human (n=5), rat (n=5), and mouse (n=4) cholangiocytes as measured using confocal microscopy (×40). Cdc25A was found to be increased in cystic cholangiocytes of patients with ARPKD, ADPKD, CHF, in PCK rats, and Pkd2$^{WS25/-}$ mice (n=5 of each). As shown in FIG. 4, western blots (n=3 for each set of data) demonstrated that Cdc25A levels were elevated in vivo and in vitro compared to normal controls, respectively.

Example 17

Treatment of Polycystic Diseases with APATONE®

Thirty seven PCK rats (20 females and 17 males) at age of 3 weeks were divided into four groups: (i) vitamin C (VC) treatment group: 5 females and 4 males; (ii) vitamin $K_3$ (VK3) treatment group: 5 females and 4 males; (iii) APATONE® treatment group: 6 females and 5 males; and (iv) control group: 4 females and 4 males. Similarly, twenty Pkd2$^{WS25/-}$ mice (12 females and 8 males) at age of 5 months were divided into four groups: (i) vitamin C (VC) treatment group: 3 females; (ii) vitamin $K_3$ (VK3) treatment group: 2 females and 2 males; (iii) APATONE® treatment group: 4 females and 3 males; and (iv) control group: 3 females and 3 males.

The VC treatment groups were given vitamin C at a concentration of 15 g/L in drinking water. The VK3 treatment groups were given vitamin $K_3$ at a concentration of 0.15 g/L in drinking water. The APATONE® treatment groups were given vitamins C and K3 at concentrations of 15 g/L and 0.15 g/L, respectively, in drinking water. The control groups were given drinking water only. Rats or mice in each group were allowed to drink freely.

The rats and mice were sacrificed after 6 weeks of treatment. The following parameters were analyzed: body weights, liver and kidney weights, serum biochemistry, renal and hepatic cystic and fibrotic areas, apoptotic and proliferation indices, expression of Cdc25A and its down-stream targets.

Since no differences was observed in liver and kidney weights between male and female PCK rats and $Pkd2^{WS25/-}$ mice, male and female data were combined for statistical analysis. Cystic and fibrotic areas were analyzed according to the procedures as described in Masyuk et al., *Gastroenterology* 2007, 132, 1104-1116. Briefly, livers and kidney sections were stained with H&E or picrosirius red collagen to assess, respectively, cystic or fibrotic areas. Measurements were done by Meta-Morph software (Universal Imaging, West Chester, Pa.), following image acquisition using a light microscope and color digital camera (Nikon DXM 1200). Hepatic and renal cystic and fibrotic areas were expressed as a percent of total hepatic or renal parenchyma, respectively.

The effect of APATONE® on liver and kidney weights was evaluated in vivo using PCK rats, an animal model of one of PLD/PKD, ARPKD. As summarized in Tables 4 and 5, no visible defects were observed in treated animals. Treatment with APATONE® decreased liver and kidney weights in PCK rats, with APATONE® being more effective than VK3 alone.

The effect of APATONE® on hepatic cystogenesis was evaluated in vivo using PCK rats. As shown in FIGS. 5A to 5F and 6A to 6F, APATONE® decreased hepatic cystic and fibrotic areas of PCK rats compared to non-treated counterparts. APATONE® suppressed hepatic and renal cystogenesis more effectively than VK3 alone.

The effect of APATONE® on liver and kidney weights was evaluated in vivo using $Pkd2^{WS25/-}$ mice, which is an animal model of ARPKD. As summarized in Tables 6 and 7, treatment with APATONE® decreased liver and kidney weights in $Pkd2^{WS25/-}$ mice with APATONE® being more effective than VK3 alone.

TABLE 4

|  | Control | VC | VK3 | APATONE® |
|---|---|---|---|---|
| Body Weight (g) | | | | |
| Male | 412 ± 15 | 416 ± 13 | 408 ± 16 | 423 ± 13 |
| Female | 270 ± 7 | 261 ± 10 | 276 ± 9 | 281 ± 15 |
| Liver Weight (g) | | | | |
| Male | 23.4 ± 0.9 | 23.3 ± 1.8 | 20.8 ± 0.5 | 19.6 ± 0.8 |
| Female | 17.0 ± 1.0 | 16.6 ± 1.3 | 15.5 ± 0.6 | 14.7 ± 0.6 |
| Liver Weight (% bw) | | | | |
| Male | 5.68 ± 0.17 | 5.61 ± 0.14 | 5.12 ± 0.09 | 4.63 ± 0.14 |
| Female | 6.31 ± 0.15 | 6.36 ± 0.23 | 5.60 ± 0.13 | 5.12 ± 0.11 |
| Kidney Weight (g) | | | | |
| Male | 4.89 ± 0.12 | 4.95 ± 0.18 | 4.57 ± 0.13 | 4.28 ± 0.14 |
| Female | 3.99 ± 0.14 | 3.88 ± 0.19 | 3.78 ± 0.09 | 3.46 ± 0.12 |
| Kidney Weight (% bw) | | | | |
| Male | 1.19 ± 0.09 | 1.19 ± 0.13 | 1.11 ± 0.11 | 1.04 ± 0.06 |
| Female | 1.48 ± 0.18 | 1.47 ± 0.11 | 1.36 ± 0.13 | 1.21 ± 0.09 |

TABLE 5

|  | VC vs Ctrl | VK3 vs Ctrl | APATONE® vs Ctrl | APATONE® vs VK3 |
|---|---|---|---|---|
| Body Weight (g) Change | | | | |
| Male | 0.8% | −1.1% | 2.6% | 3.8% |
| Female | −3.3% | 2.2% | 3.6% | 1.8% |
| Liver Weight (g) Change | | | | |
| Male | −0.4% | −10.9%* | −16.4%* | −6.2% |
| Female | −2.8% | −9.2%* | −14.0%* | −5.3% |
| Liver Weight (% bw) Change | | | | |
| Male | −1.2% | −9.8%* | −18.5%* | −9.8%* |
| Female | 0.8% | −11.3%* | −18.7%* | −8.6%* |
| Kidney Weight (g) Change | | | | |
| Male | 1.2% | −6.5%* | −12.5%* | −6.4%* |
| Female | −2.8% | −5.2%* | −13.3%* | −8.5%* |
| Kidney Weight (% bw) Change | | | | |
| Male | 0 | −6.7%* | −12.6%* | −6.5%* |
| Female | −0.7% | −8.1%* | −18.2%* | −11.0%* |

*p ≤ 0.05

TABLE 6

|  | Control | VC | VK3 | APATONE® |
|---|---|---|---|---|
| Body Weight (g) | 26.3 ± 1.2 | 26.7 ± 2.0 | 27.9 ± 1.9 | 26.6 ± 0.9 |
| Liver Weight (g) | 2.12 ± 0.11 | 2.29 ± 0.43 | 1.64 ± 0.15 | 1.05 ± 0.13 |
| Liver Weight (%) | 8.05 ± 0.16 | 9.29 ± 2.01 | 5.87 ± 0.36 | 4.45 ± 0.21 |
| Kidney Weight (g) | 0.49 ± 0.02 | 0.46 ± 0.04 | 0.42 ± 0.01 | 0.32 ± 0.02 |
| Kidney Weight (%) | 1.89 ± 0.11 | 1.76 ± 0.16 | 1.53 ± 0.05 | 1.38 ± 0.06 |

TABLE 7

|  | VC vs Ctrl | VK3 vs Ctrl | APATONE® vs Ctrl | APATONE® vs VK3 |
|---|---|---|---|---|
| Body Weight (g) Change | 1.5% | 5.8% | −3.0% | −8.3% |
| Liver Weight (g) Change | 8.0% | −22.6%* | −50.5%* | −36.0%* |

TABLE 7-continued

|  | VC vs Ctrl | VK3 vs Ctrl | APATONE® vs Ctrl | APATONE® vs VK3 |
|---|---|---|---|---|
| Liver Weight (% bw) Change | 15.4% | −27.1%* | −44.7%* | −24.2%* |
| Kidney Weight (g) Change | −6.1% | −14.3%* | −34.7%* | −2.38%* |
| Kidney Weight (% bw) Change | −6.7% | −19.0%* | −27.0%* | −9.8%* |

*$p \leq 0.05$

The effect of APATONE® on hepatic cystogenesis was evaluated in vivo using Pkd2$^{WS25/-}$ mice. As shown in FIGS. 7A to 7F and 8A to 8F, APATONE® decreased hepatic cystic and fibrotic areas of Pkd2$^{WS25/-}$ mice compared to non-treated counterparts. APATONE® suppressed hepatic and renal cystogenesis more effectively than VK3 alone.

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A method of treating, a polycystic disease in a subject, comprising administering to the subject a therapeutically effective amount of vitamin C, or a pharmaceutically acceptable salt, solvate, or hydrate thereof, in combination with chromium-free vitamin K, or a single enantiomer, a mixture of enantiomers, or a mixture of diastereomers thereof, or a pharmaceutically acceptable salt, solvate, or hydrate thereof wherein the polycystic disease is a polycystic kidney disease or a polycystic liver disease.

2. The method of claim 1, wherein the polycystic disease is a polycystic kidney disease.

3. The method of claim 1, wherein the polycystic disease is a polycystic liver disease.

4. The method of claim 1, wherein the chromium content of the chromium-free vitamin K is no greater than 10 ppm, no greater than 5 ppm, no greater than 2 ppm, no greater than 1 ppm, or no greater than 100 ppb.

5. The method of claim 1, wherein the subject is a human.

6. The method of claim 1, wherein vitamin C is administered orally.

7. The method of claim 1, wherein chromium-free vitamin K is administered orally.

8. The method of claim 1, wherein vitamin C and chromium-free vitamin K are administered together in a single composition comprising vitamin C, or a pharmaceutically acceptable salt, solvate, or hydrate thereof, and chromium-free vitamin K, or a single enantiomer, a mixture of enantiomers, or a mixture of diastereomers thereof, or a pharmaceutically acceptable salt, solvate, or hydrate thereof.

9. The method of claim 1, wherein vitamin C and chromium-free vitamin K are formulated together in a single oral dosage form.

10. The method of claim 9, wherein the single oral dosage form is provided as a tablet.

11. The method of claim 9, wherein the single oral dosage form is provided as a capsule.

12. The method of claim 11, wherein the capsule contains about 500 mg of vitamin C, or a pharmaceutically acceptable salt, solvate, or hydrate thereof; and about 5 mg of chromium-free vitamin K, or a single enantiomer, a mixture of enantiomers, or a mixture of diastereomers thereof, or a pharmaceutically acceptable salt, solvate, or hydrate thereof.

13. The method of claim 11, wherein the capsule consists essentially of vitamin C, or a pharmaceutically acceptable salt, solvate, or hydrate thereof, in combination with chromium-free vitamin K, or a single enantiomer, a mixture of enantiomers, or a mixture of diastereomers thereof, or a pharmaceutically acceptable salt, solvate, or hydrate thereof.

14. The method of claim 1, wherein chromium-free vitamin K is chromium-free vitamin $K_3$.

15. The method of claim 14, wherein chromium-free vitamin $K_3$ is 1,2,3,4-tetrahydro-2-methyl-1,4-dioxo-2-naphthalenesulfonic acid or a pharmaceutically acceptable salt thereof or a pharmaceutically acceptable solvate or hydrate thereof.

16. The method of claim 14, wherein chromium-free vitamin $K_3$ is an alkali or alkaline earth metal salt of 1,2,3,4-tetrahydro-2-methyl-1,4-dioxo-2-naphthalenesulfonic acid, or a pharmaceutically acceptable solvate or hydrate thereof.

17. The method of claim 14, wherein chromium-free vitamin $K_3$ is sodium or magnesium 1,2,3,4-tetrahydro-2-methyl-1,4-dioxo-2-naphthalenesulfonate, or a pharmaceutically acceptable solvate or hydrate thereof.

18. The method of claim 14, wherein chromium-free vitamin $K_3$ is anhydrous sodium 1,2,3,4-tetrahydro-2-methyl-1,4-dioxo-2-naphthalenesulfonate.

19. The method of claim 1, wherein vitamin C is L-ascorbic acid or a pharmaceutically acceptable salt thereof, or a pharmaceutically acceptable solvate or hydrate thereof.

20. The method of claim 19, wherein vitamin C is an alkali or alkaline earth metal salt of L-ascorbic acid, or a pharmaceutically acceptable solvate or hydrate thereof.

21. The method of claim 19, wherein vitamin C is sodium L-ascorbate, or a pharmaceutically acceptable solvate or hydrate thereof.

22. The method of claim 19, wherein vitamin C is magnesium L-ascorbate, or a pharmaceutically acceptable solvate or hydrate thereof.

23. The method of claim 1, wherein the molar ratio of vitamin C to chromium-free vitamin K is ranging from about 50 to about 500.

24. The method of claim 23, wherein the molar ratio of vitamin C to chromium-free vitamin K is about 100.

25. The method of claim 1, wherein vitamin C is administered once, twice, three times, four times, five times, or six times a day.

26. The method of claim 1, wherein vitamin C is administered every 4 to 6 hours a day.

27. The method of claim 1, wherein chromium-free vitamin K is administered once, twice, three times, four times, five times, or six times a day.

28. The method of claim 1, wherein chromium-free vitamin K is administered every 4 to 6 hours a day.

29. The method of claim 1, wherein vitamin C is administered in an amount ranging from about 500 mg to about 10,000 mg per day, and vitamin K is administered in an amount ranging from about 3 mg to about 100 mg per day.

30. The method of claim 29, wherein vitamin C is administered in an amount of about 2,000 mg or about 3,000 mg per day, and vitamin K is administered in an amount of about 12 mg to about 19 mg per day.

31. The method of claim 29, wherein vitamins C and K are each administered twice a day.

32. The method of claim 1, wherein vitamins C and K are administered as one or more capsules, each comprising about 500 mg of sodium L-ascorbate and about 3 mg of sodium 1,2,3,4-tetrahydro-2-methyl-1,4-dioxo-2-naphthalenesulfonate.

33. The method of claim 1, wherein vitamin K is 2-methyl-1,4-naphthalenedione, or a pharmaceutically acceptable solvate or hydrate thereof.

* * * * *